(12) United States Patent
Yam et al.

(10) Patent No.: US 10,190,145 B2
(45) Date of Patent: Jan. 29, 2019

(54) EXPRESSION OF BIOLOGICALLY ACTIVE PROTEINS IN A BACTERIAL CELL-FREE SYNTHESIS SYSTEM USING BACTERIAL CELLS TRANSFORMED TO EXHIBIT ELEVATED LEVELS OF CHAPERONE EXPRESSION

(71) Applicant: Sutro Biopharma, Inc., South San Francisco, CA (US)

(72) Inventors: Alice Yam, Fremont, CA (US); Dan Groff, Oakland, CA (US); Patrick Rivers, Oakland, CA (US); Christopher D. Thanos, Tiburon, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 0 days.

(21) Appl. No.: 14/256,324

(22) Filed: Apr. 18, 2014

(65) Prior Publication Data
US 2014/0315245 A1 Oct. 23, 2014

Related U.S. Application Data

(60) Provisional application No. 61/937,069, filed on Feb. 7, 2014, provisional application No. 61/813,914, filed on Apr. 19, 2013.

(51) Int. Cl.
*C12P 21/00* (2006.01)
*C12N 9/90* (2006.01)
*C12P 21/02* (2006.01)

(52) U.S. Cl.
CPC ............... *C12P 21/00* (2013.01); *C12N 9/90* (2013.01); *C12P 21/02* (2013.01)

(58) Field of Classification Search
None
See application file for complete search history.

(56) References Cited

U.S. PATENT DOCUMENTS

| 7,871,794 B2 * | 1/2011 | Knapp et al. ............... 435/68.1 |
| 2004/0248238 A1 | 12/2004 | Watzele et al. |

FOREIGN PATENT DOCUMENTS

| CN | 102348807 A | 2/2012 |
| CN | 102732548 A | 10/2012 |
| JP | 2005253432 A | 9/2005 |
| JP | 2006061080 A | 3/2006 |
| WO | 03/025116 A2 | 3/2003 |
| WO | 2008/066583 A2 | 6/2008 |

OTHER PUBLICATIONS

Kang et al., Biotechnol. Prog. 2005, vol. 21, pp. 1412-1419.*
Oh et al. (Cell-free production of functional antibody fragments; Bioprocess Biosyst Eng (2010) 33:127-132 (Year: 2010).*
Kang et al., "Cell-Free Production of Aggregation-Prone Proteins in Soluble and Active Forms", *Biotechnol. Prog.*, vol. 21, pp. 1412-1419.
Levy et al., "Improved Panning Output and Antibody Fragment Production by Co-expression with the Peptidyl Prolyl Isomerase, FkpA, in the Cytoplasm of *Escherichia coli*", (XOMA) at IBC Antibody Engineering, Dec. 3-6, 2012, in San Diego.
Wang, "Protein Disulfide Isomerase Assists Protein Folding as Both an Isomerase and a Chaperone*", *Annals New York Academy of Sciences*, pp. 9-13 (1998).
Wang, "Protein Disulfide Isomerase as an Enzyme and a Chaperone in Protein Folding", *Methods in Enzymology*, vol. 348, pp. 66-75 (2002).
International Search Report and Written Opinion dated Nov. 3, 2014 of International Patent Application No. PCT/US2014/034643.
Database Biosis, Biosciences Information Service; Feb. 11, 2014, Groff et al., "Engineering toward a bacterial "endoplasmic reticulum" for the rapid expression of immunoglobulin proteins", XP002731141.
Kang et al., "Cell-Free Production of Aggregation-Prone Proteins in Soluble and Active Forms", Biotechnology Progress, vol. 21, No. 4, pp. 1412-1419 (2005).
Oh et al., "Cell-free production of functional antibody fragments", Bioprocess and Biosystems Engineering, vol. 33, No. 1, pp. (2009).
Oh et al., "Providing an Oxidizing Environment for the Cell-Free Expression of Disulfide-Containing Proteins by Exhuasting the Reducing Acitivty of *Escherichia coli* S30 Extract", Biotechnology Progress, vol. 22, No. 4, pp. 1225-1228 (2006).
Xu et al., "Effect of folding factors in rescuing unstable heterologous lipase B to enhance its overexpression in the periplasm of *Escherichia coli*", Applied Microbiology and Biotechnology, vol. 79, No. 6, pp. 1035-1044 (2008).
International Preliminary Report on Patentability dated Oct. 29, 2015 of International Patent Application No. PCT/US2014/034643, 20 pages.
SG11201508642W, "Written Opinion", dated Dec. 8, 2016, 8 pages.
SG11201508642W, "Written Opinion", dated Oct. 30, 2017, 7 pages.

(Continued)

*Primary Examiner* — Antonio Galisteo Gonzalez
(74) *Attorney, Agent, or Firm* — Kilpatrick Townsend & Stockton LLP

(57) ABSTRACT

The present disclosure describes methods and systems for improving the expression of a properly folded, biologically active protein of interest in a cell free synthesis system. The methods and systems use a bacterial cell free extract having an active oxidative phosphorylation system, and include an exogenous protein chaperone. The exogenous protein chaperone can be expressed by the bacteria used to prepare the cell free extract. The exogenous protein chaperone can be a protein disulfide isomerase and/or a peptidyl-prolyl cis-trans isomerase. The inventors discovered that the combination of a protein disulfide isomerase and a peptidyl-prolyl cis-trans isomerase produces a synergistic increase in the amount of properly folded, biologically active protein of interest.

20 Claims, 14 Drawing Sheets
Specification includes a Sequence Listing.

(56) References Cited

OTHER PUBLICATIONS

Schlapschy et al., "A System for Concomitant Overexpression of Four Periplasmic Folding Catalysts to Improve Secretory Protein Production in *Escherichia coli*", Protein Engineering, Design & Selection, 2006, 19(8):385-390.
Tang et al., "SnapShot: Molecular Chaperones, Part II", Department of Cellular Biochemistry, Max Planck Institute of Biochemistry, Martinsried, Germany, Cell, vol. 128, Jan. 26, 2007, 412-412.e1.

* cited by examiner

| Redox proteins | | MW (kDa) | uM |
|---|---|---|---|
| | DsbC | 23.6 | 26 |
| | DsbG | 29.8 | 11 |
| | yPDI | 55.8 | 3 |
| | hPDI | 55.3 | 3 |
| | yTrr1 | 34.2 | 18 |
| | yGlr1 | 53.4 | 3 |

| Prolyl isomerases | | MW (kDa) | uM |
|---|---|---|---|
| | SlyD | 20.9 | 43 |
| | tig | 48.2 | 15 |
| | SurA | 45.1 | 8 |
| | FkpA | 28.9 | 48 |
| | hPPIB | 20.3 | 23 |
| | Cpr1 | 17.4 | 23 |
| | Cpr6 | 42.1 | 12 |
| | Fpr1 | 12.2 | 63 |

| Deaggre-gases | | MW (kDa) | uM |
|---|---|---|---|
| | hERdj3 | 38.2 | 12 |
| | hBiP | 70.5 | 3 |
| | yHsc82 | 80.9 | 7 |
| | IbpA | 15.8 | 52 |
| | IbpB | 16.1 | 69 |
| | Skp | 17.7 | 71 |

Concentration at which chaperones were expressed:

Growth Rates

| Strain | SBHS16 | +1xDsbC | +2X ver 1 | +2X ver 2 |
|---|---|---|---|---|
| Doubling time (h) | .65 | .64 | .70 | .73 |

SEQUENCE LISTING

<160> NUMBER OF SEQ ID NOS: 29

<210> SEQ ID NO 1
<211> LENGTH: 236
<212> TYPE: PRT
<213> ORGANISM: Escherichia coli
<220> FEATURE:
<223> OTHER INFORMATION: E. coli strain K-12 substrain MG1655 protein disulfide isomerase II, thiol:disulfide interchange protein DsbC, locus b2893, JW2861, xprA

<400> SEQUENCE: 1

Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45

Thr Val Leu Thr Asn Ser Gly Val Leu Tyr Ile Thr Asp Asp Gly Lys
    50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

```
Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys
225                 230                 235
```

<210> SEQ ID NO 2
<211> LENGTH: 208
<212> TYPE: PRT
<213> ORGANISM: Escherichia coli
<220> FEATURE:
<223> OTHER INFORMATION: E. coli strain K-12 substrain MG1655
      periplasmic protein disulfide isomerase I, thiol:disulfide
      interchange protein DsbA, locus b3860, JW3832, dsf, ppfA

<400> SEQUENCE: 2

```
Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
    50                  55                  60

Val Lys Lys Lys Leu Pro Glu Gly Val Lys Met Thr Lys Tyr His Val
65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
        115                 120                 125

Asp Val Phe Ile Asn Ala Gly Ile Lys Gly Glu Glu Tyr Asp Ala Ala
    130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
        195                 200                 205
```

<210> SEQ ID NO 3
<211> LENGTH: 176
<212> TYPE: PRT
<213> ORGANISM: Escherichia coli
<220> FEATURE:
<223> OTHER INFORMATION: E. coli strain K-12 substrain MG1655
      oxidoreductase that catalyzes reoxidation of DsbA protein
      disulfide isomerase I, disulfide bond formation protein B (DsbB),
      locus b1185, JW5182, roxB, ycgA

<400> SEQUENCE: 3

```
Met Leu Arg Phe Leu Asn Gln Cys Ser Gln Gly Arg Gly Ala Trp Leu
1               5                   10                  15

Leu Met Ala Phe Thr Ala Leu Ala Leu Glu Leu Thr Ala Leu Trp Phe
            20                  25                  30

Gln His Val Met Leu Leu Lys Pro Cys Val Leu Cys Ile Tyr Glu Arg
        35                  40                  45
```

```
Cys Ala Leu Phe Gly Val Leu Gly Ala Leu Ile Gly Ala Ile Ala
    50                  55                  60

Pro Lys Thr Pro Leu Arg Tyr Val Ala Met Val Ile Trp Leu Tyr Ser
65                  70                  75                  80

Ala Phe Arg Gly Val Gln Leu Thr Tyr Glu His Thr Met Leu Gln Leu
                85                  90                  95

Tyr Pro Ser Pro Phe Ala Thr Cys Asp Phe Met Val Arg Phe Pro Glu
                100                 105                 110

Trp Leu Pro Leu Asp Lys Trp Val Pro Gln Val Phe Val Ala Ser Gly
            115                 120                 125

Asp Cys Ala Glu Arg Gln Trp Asp Phe Leu Gly Leu Glu Met Pro Gln
            130                 135                 140

Trp Leu Leu Gly Ile Phe Ile Ala Tyr Leu Ile Val Ala Val Leu Val
145                 150                 155                 160

Val Ile Ser Gln Pro Phe Lys Ala Lys Lys Arg Asp Leu Phe Gly Arg
                165                 170                 175

<210> SEQ ID NO 4
<211> LENGTH: 565
<212> TYPE: PRT
<213> ORGANISM: Escherichia coli
<220> FEATURE:
<223> OTHER INFORMATION: E. coli strain K-12 substrain MG1655 fused
      thiol:disulfide interchange protein DsbD, activator of DsbC/
      conserved protein, C-type cytochrome biogenesis protein CycZ,
      copper tolerance protein, protein-disulfide reductase, locus
      b4136, JW5734, cutA2

<400> SEQUENCE: 4

Met Ala Gln Arg Ile Phe Thr Leu Ile Leu Leu Leu Cys Ser Thr Ser
1               5                   10                  15

Val Phe Ala Gly Leu Phe Asp Ala Pro Gly Arg Ser Gln Phe Val Pro
                20                  25                  30

Ala Asp Gln Ala Phe Ala Phe Asp Phe Gln Gln Asn Gln His Asp Leu
            35                  40                  45

Asn Leu Thr Trp Gln Ile Lys Asp Gly Tyr Tyr Leu Tyr Arg Lys Gln
50                  55                  60

Ile Arg Ile Thr Pro Glu His Ala Lys Ile Ala Asp Val Gln Leu Pro
65                  70                  75                  80

Gln Gly Val Trp His Glu Asp Glu Phe Tyr Gly Lys Ser Glu Ile Tyr
                85                  90                  95

Arg Asp Arg Leu Thr Leu Pro Val Thr Ile Asn Gln Ala Ser Ala Gly
            100                 105                 110

Ala Thr Leu Thr Val Thr Tyr Gln Gly Cys Ala Asp Ala Gly Phe Cys
            115                 120                 125

Tyr Pro Pro Glu Thr Lys Thr Val Pro Leu Ser Glu Val Val Ala Asn
            130                 135                 140

Asn Ala Ala Pro Gln Pro Val Ser Val Pro Gln Gln Glu Gln Pro Thr
145                 150                 155                 160

Ala Gln Leu Pro Phe Ser Ala Leu Trp Ala Leu Leu Ile Gly Ile Gly
                165                 170                 175

Ile Ala Phe Thr Pro Cys Val Leu Pro Met Tyr Pro Leu Ile Ser Gly
            180                 185                 190

Ile Val Leu Gly Gly Lys Gln Arg Leu Ser Thr Ala Arg Ala Leu Leu
            195                 200                 205

Leu Thr Phe Ile Tyr Val Gln Gly Met Ala Leu Thr Tyr Thr Ala Leu
```

```
        210                 215                 220
Gly Leu Val Val Ala Ala Gly Leu Gln Phe Gln Ala Ala Leu Gln
225                 230                 235                 240

His Pro Tyr Val Leu Ile Gly Leu Ala Ile Val Phe Thr Leu Ala
                245                 250                 255

Met Ser Met Phe Gly Leu Phe Thr Leu Gln Leu Pro Ser Ser Leu Gln
            260                 265                 270

Thr Arg Leu Thr Leu Met Ser Asn Arg Gln Gln Gly Gly Ser Pro Gly
                275                 280                 285

Gly Val Phe Val Met Gly Ala Ile Ala Gly Leu Ile Cys Ser Pro Cys
290                 295                 300

Thr Thr Ala Pro Leu Ser Ala Ile Leu Leu Tyr Ile Ala Gln Ser Gly
305                 310                 315                 320

Asn Met Trp Leu Gly Gly Thr Leu Tyr Leu Tyr Ala Leu Gly Met
                325                 330                 335

Gly Leu Pro Leu Met Leu Ile Thr Val Phe Gly Asn Arg Leu Leu Pro
                340                 345                 350

Lys Ser Gly Pro Trp Met Glu Gln Val Lys Thr Ala Phe Gly Phe Val
                355                 360                 365

Ile Leu Ala Leu Pro Val Phe Leu Leu Glu Arg Val Ile Gly Asp Val
                370                 375                 380

Trp Gly Leu Arg Leu Trp Ser Ala Leu Gly Val Ala Phe Phe Gly Trp
385                 390                 395                 400

Ala Phe Ile Thr Ser Leu Gln Ala Lys Arg Gly Trp Met Arg Ile Val
                405                 410                 415

Gln Ile Ile Leu Leu Ala Ala Ala Leu Val Ser Val Arg Pro Leu Gln
                420                 425                 430

Asp Trp Ala Phe Gly Ala Thr His Thr Ala Gln Thr Gln Thr His Leu
                435                 440                 445

Asn Phe Thr Gln Ile Lys Thr Val Asp Glu Leu Asn Gln Ala Leu Val
                450                 455                 460

Glu Ala Lys Gly Lys Pro Val Met Leu Asp Leu Tyr Ala Asp Trp Cys
465                 470                 475                 480

Val Ala Cys Lys Glu Phe Glu Lys Tyr Thr Phe Ser Asp Pro Gln Val
                485                 490                 495

Gln Lys Ala Leu Ala Asp Thr Val Leu Leu Gln Ala Asn Val Thr Ala
                500                 505                 510

Asn Asp Ala Gln Asp Val Ala Leu Leu Lys His Leu Asn Val Leu Gly
                515                 520                 525

Leu Pro Thr Ile Leu Phe Phe Asp Gly Gln Gly Gln Glu His Pro Gln
                530                 535                 540

Ala Arg Val Thr Gly Phe Met Asp Ala Glu Thr Phe Ser Ala His Leu
545                 550                 555                 560

Arg Asp Arg Gln Pro
                565

<210> SEQ ID NO 5
<211> LENGTH: 248
<212> TYPE: PRT
<213> ORGANISM: Escherichia coli
<220> FEATURE:
<223> OTHER INFORMATION: E. coli strain K-12 substrain MG1655
      periplasmic thiol:disulfide interchange protein DsbG, locus
      b0604, JW00597, ybdP

<400> SEQUENCE: 5
```

```
Met Leu Lys Lys Ile Leu Leu Ala Leu Leu Pro Ala Ile Ala Phe
  1               5                  10                  15

Ala Glu Glu Leu Pro Ala Pro Val Lys Ala Ile Glu Lys Gln Gly Ile
             20                  25                  30

Thr Ile Ile Lys Thr Phe Asp Ala Pro Gly Gly Met Lys Gly Tyr Leu
             35                  40                  45

Gly Lys Tyr Gln Asp Met Gly Val Thr Ile Tyr Leu Thr Pro Asp Gly
 50                  55                  60

Lys His Ala Ile Ser Gly Tyr Met Tyr Asn Glu Lys Gly Glu Asn Leu
 65                  70                  75                  80

Ser Asn Thr Leu Ile Glu Lys Glu Ile Tyr Ala Pro Ala Gly Arg Glu
                 85                  90                  95

Met Trp Gln Arg Met Glu Gln Ser His Trp Leu Leu Asp Gly Lys Lys
                100                 105                 110

Asp Ala Pro Val Ile Val Tyr Val Phe Ala Asp Pro Phe Cys Pro Tyr
            115                 120                 125

Cys Lys Gln Phe Trp Gln Gln Ala Arg Pro Trp Val Asp Ser Gly Lys
        130                 135                 140

Val Gln Leu Arg Thr Leu Leu Val Gly Val Ile Lys Pro Glu Ser Pro
145                 150                 155                 160

Ala Thr Ala Ala Ala Ile Leu Ala Ser Lys Asp Pro Ala Lys Thr Trp
                165                 170                 175

Gln Gln Tyr Glu Ala Ser Gly Gly Lys Leu Lys Leu Asn Val Pro Ala
            180                 185                 190

Asn Val Ser Thr Glu Gln Met Lys Val Leu Ser Asp Asn Glu Lys Leu
        195                 200                 205

Met Asp Asp Leu Gly Ala Asn Val Thr Pro Ala Ile Tyr Tyr Met Ser
210                 215                 220

Lys Glu Asn Thr Leu Gln Gln Ala Val Gly Leu Pro Asp Gln Lys Thr
225                 230                 235                 240

Leu Asn Ile Ile Met Gly Asn Lys
                245
```

<210> SEQ ID NO 6
<211> LENGTH: 270
<212> TYPE: PRT
<213> ORGANISM: Escherichia coli
<220> FEATURE:
<223> OTHER INFORMATION: E. coli strain K-12 substrain MG1655 FKBP
      (FK506 binding protein)-type peptidyl-prolyl cis-trans
      isomerase (PPIase) (rotamase) FkpA, locus b3347,
      JW3309, yzzS

<400> SEQUENCE: 6

```
Met Lys Ser Leu Phe Lys Val Thr Leu Leu Ala Thr Thr Met Ala Val
  1               5                  10                  15

Ala Leu His Ala Pro Ile Thr Phe Ala Ala Glu Ala Lys Pro Ala
             20                  25                  30

Thr Ala Ala Asp Ser Lys Ala Ala Phe Lys Asn Asp Asp Gln Lys Ser
             35                  40                  45

Ala Tyr Ala Leu Gly Ala Ser Leu Gly Arg Tyr Met Glu Asn Ser Leu
 50                  55                  60

Lys Glu Gln Glu Lys Leu Gly Ile Lys Leu Asp Lys Asp Gln Leu Ile
 65                  70                  75                  80

Ala Gly Val Gln Asp Ala Phe Ala Asp Lys Ser Lys Leu Ser Asp Gln
                 85                  90                  95
```

```
Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
            115                 120                 125

Lys Glu Tyr Arg Glu Lys Phe Ala Lys Glu Lys Gly Val Lys Thr Ser
        130                 135                 140

Ser Thr Gly Leu Val Tyr Gln Val Val Glu Ala Gly Lys Gly Glu Ala
145                 150                 155                 160

Pro Lys Asp Ser Asp Thr Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
        210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270

<210> SEQ ID NO 7
<211> LENGTH: 196
<212> TYPE: PRT
<213> ORGANISM: Escherichia coli
<220> FEATURE:
<223> OTHER INFORMATION: E. coli strain K-12 substrain MG1655 FKBP
      (FK506 binding protein)-type peptidyl-prolyl cis-trans isomerase
      (PPIase) (rotamase), histidine-rich protein, sensitivity to lysis
      protein D (SlyD), metallochaperone SlyD, locus b3349, JW3311

<400> SEQUENCE: 7

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Cys Cys Gly Gly His Gly His Asp His Gly
                165                 170                 175
```

His Glu His Gly Gly Glu Gly Cys Cys Gly Lys Gly Asn Gly Gly
                180                 185                 190

Cys Gly Cys His
        195

<210> SEQ ID NO 8
<211> LENGTH: 428
<212> TYPE: PRT
<213> ORGANISM: Escherichia coli
<220> FEATURE:
<223> OTHER INFORMATION: E. coli strain K-12 substrain MG1655
      peptidyl-prolyl cis-trans isomerase (PPIase)
      (rotamase), survival protein A (SurA), chaperone
      SurA, locus b0053, JW0052

<400> SEQUENCE: 8

Met Lys Asn Trp Lys Thr Leu Leu Leu Gly Ile Ala Met Ile Ala Asn
 1               5                  10                  15

Thr Ser Phe Ala Ala Pro Gln Val Val Asp Lys Val Ala Ala Val Val
            20                  25                  30

Asn Asn Gly Val Val Leu Glu Ser Asp Val Asp Gly Leu Met Gln Ser
        35                  40                  45

Val Lys Leu Asn Ala Ala Gln Ala Arg Gln Gln Leu Pro Asp Asp Ala
 50                  55                  60

Thr Leu Arg His Gln Ile Met Glu Arg Leu Ile Met Asp Gln Ile Ile
65                  70                  75                  80

Leu Gln Met Gly Gln Lys Met Gly Val Lys Ile Ser Asp Glu Gln Leu
                85                  90                  95

Asp Gln Ala Ile Ala Asn Ile Ala Lys Gln Asn Asn Met Thr Leu Asp
            100                 105                 110

Gln Met Arg Ser Arg Leu Ala Tyr Asp Gly Leu Asn Tyr Asn Thr Tyr
        115                 120                 125

Arg Asn Gln Ile Arg Lys Glu Met Ile Ile Ser Glu Val Arg Asn Asn
130                 135                 140

Glu Val Arg Arg Arg Ile Thr Ile Leu Pro Gln Glu Val Glu Ser Leu
145                 150                 155                 160

Ala Gln Gln Val Gly Asn Gln Asn Asp Ala Ser Thr Glu Leu Asn Leu
                165                 170                 175

Ser His Ile Leu Ile Pro Leu Pro Glu Asn Pro Thr Ser Asp Gln Val
            180                 185                 190

Asn Glu Ala Glu Ser Gln Ala Arg Ala Ile Val Asp Gln Ala Arg Asn
        195                 200                 205

Gly Ala Asp Phe Gly Lys Leu Ala Ile Ala His Ser Ala Asp Gln Gln
210                 215                 220

Ala Leu Asn Gly Gly Gln Met Gly Trp Gly Arg Ile Gln Glu Leu Pro
225                 230                 235                 240

Gly Ile Phe Ala Gln Ala Leu Ser Thr Ala Lys Lys Gly Asp Ile Val
                245                 250                 255

Gly Pro Ile Arg Ser Gly Val Gly Phe His Ile Leu Lys Val Asn Asp
            260                 265                 270

Leu Arg Gly Glu Ser Lys Asn Ile Ser Val Thr Glu Val His Ala Arg
        275                 280                 285

His Ile Leu Leu Lys Pro Ser Pro Ile Met Thr Asp Glu Gln Ala Arg
290                 295                 300

Val Lys Leu Glu Gln Ile Ala Ala Asp Ile Lys Ser Gly Lys Thr Thr
305                 310                 315                 320

```
Phe Ala Ala Ala Ala Lys Glu Phe Ser Gln Asp Pro Gly Ser Ala Asn
                325                 330                 335

Gln Gly Gly Asp Leu Gly Trp Ala Thr Pro Asp Ile Phe Asp Pro Ala
            340                 345                 350

Phe Arg Asp Ala Leu Thr Arg Leu Asn Lys Gly Gln Met Ser Ala Pro
        355                 360                 365

Val His Ser Ser Phe Gly Trp His Leu Ile Glu Leu Leu Asp Thr Arg
    370                 375                 380

Asn Val Asp Lys Thr Asp Ala Ala Gln Lys Asp Arg Ala Tyr Arg Met
385                 390                 395                 400

Leu Met Asn Arg Lys Phe Ser Glu Glu Ala Ala Ser Trp Met Gln Glu
                405                 410                 415

Gln Arg Ala Ser Ala Tyr Val Lys Ile Leu Ser Asn
            420                 425

<210> SEQ ID NO 9
<211> LENGTH: 161
<212> TYPE: PRT
<213> ORGANISM: Escherichia coli
<220> FEATURE:
<223> OTHER INFORMATION: E. coli strain K-12 substrain MG1655
      periplasmic molecular chaperone for outer membrane proteins
      Skp, DNA-binding 17 kDa protein, histone-like
      protein HLP-1 (hlpA), locus b0178, JW0173, ompH

<400> SEQUENCE: 9

Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
            20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Glu Lys Asp Val Met Ala Gln Arg Gln Thr Phe Ala Gln
                85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys

<210> SEQ ID NO 10
<211> LENGTH: 522
<212> TYPE: PRT
<213> ORGANISM: Saccharomyces cerevisiae
<220> FEATURE:
<223> OTHER INFORMATION: S. cerevisiae strain S288c protein disulfide
      isomerase PDI1 (yPDI), thioredoxin-related
      glycoprotein 1 (TRG1), locus YCL043C

<400> SEQUENCE: 10
```

-continued

```
Met Lys Phe Ser Ala Gly Ala Val Leu Ser Trp Ser Ser Leu Leu Leu
 1               5                  10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
         35                  40                  45

His Asp Leu Val Leu Ala Glu Phe Phe Ala Pro Trp Cys Gly His Cys
     50                  55                  60

Lys Asn Met Ala Pro Glu Tyr Val Lys Ala Ala Glu Thr Leu Val Glu
 65                  70                  75                  80

Lys Asn Ile Thr Leu Ala Gln Ile Asp Cys Thr Glu Asn Gln Asp Leu
                 85                  90                  95

Cys Met Glu His Asn Ile Pro Gly Phe Pro Ser Leu Lys Ile Phe Lys
                100                 105                 110

Asn Ser Asp Val Asn Asn Ser Ile Asp Tyr Glu Gly Pro Arg Thr Ala
            115                 120                 125

Glu Ala Ile Val Gln Phe Met Ile Lys Gln Ser Gln Pro Ala Val Ala
        130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Glu Leu Glu Glu
            260                 265                 270

Tyr Lys Pro Leu Phe Thr Glu Leu Ala Lys Lys Asn Arg Gly Leu Met
        275                 280                 285

Asn Phe Val Ser Ile Asp Ala Arg Lys Phe Gly Arg His Ala Gly Asn
290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
        355                 360                 365

Glu Ile Phe Glu Asn Gln Asp Ser Ser Val Phe Gln Leu Val Gly Lys
370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
```

```
                    420                 425                 430
Ala Lys Leu Asp His Thr Glu Asn Asp Val Arg Gly Val Val Ile Glu
                435                 440                 445

Gly Tyr Pro Thr Ile Val Leu Tyr Pro Gly Gly Lys Lys Ser Glu Ser
                450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Glu Ala Asp Ala Asp Ala Glu Leu Ala
                500                 505                 510

Asp Glu Glu Asp Ala Ile His Asp Glu Leu
                515                 520

<210> SEQ ID NO 11
<211> LENGTH: 508
<212> TYPE: PRT
<213> ORGANISM: Homo sapiens
<220> FEATURE:
<223> OTHER INFORMATION: protein disulfide isomerase family A member 1
      (PDIA1, PDI) precursor. collagen prolyl 4-hydroxylase subunit beta
      (P4HB, P4Hbeta), procollagen-proline 2-oxoglutarate 4-dioxygenase
      beta, thyroid hormone-binding protein p55, GIT, ERBA2L, DSI

<400> SEQUENCE: 11

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
                20                  25                  30

Asn Phe Ala Glu Ala Leu Ala Ala His Lys Tyr Leu Leu Val Glu Phe
            35                  40                  45

Tyr Ala Pro Trp Cys Gly His Cys Lys Ala Leu Ala Pro Glu Tyr Ala
        50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
                100                 105                 110

Pro Lys Glu Tyr Thr Ala Gly Arg Glu Ala Asp Asp Ile Val Asn Trp
            115                 120                 125

Leu Lys Lys Arg Thr Gly Pro Ala Ala Thr Thr Leu Pro Asp Gly Ala
        130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
                180                 185                 190

Phe Ser Lys Tyr Gln Leu Asp Lys Asp Gly Val Val Leu Phe Lys Lys
            195                 200                 205

Phe Asp Glu Gly Arg Asn Asn Phe Glu Gly Glu Val Thr Lys Glu Asn
        210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
```

```
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
            275                 280                 285

Ile Phe Ile Asp Ser Asp His Thr Asp Asn Gln Arg Ile Leu Glu Phe
            290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
                340                 345                 350

Pro His Leu Met Ser Gln Glu Leu Pro Glu Asp Trp Asp Lys Gln Pro
                355                 360                 365

Val Lys Val Leu Val Gly Lys Asn Phe Glu Asp Val Ala Phe Asp Glu
                370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
                420                 425                 430

Glu Ala Val Lys Val His Ser Phe Pro Thr Leu Lys Phe Phe Pro Ala
                435                 440                 445

Ser Ala Asp Arg Thr Val Ile Asp Tyr Asn Gly Glu Arg Thr Leu Asp
            450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
                500                 505

<210> SEQ ID NO 12
<211> LENGTH: 319
<212> TYPE: PRT
<213> ORGANISM: Saccharomyces cerevisiae
<220> FEATURE:
<223> OTHER INFORMATION: S. cerevisiae strain S288c thioredoxin-
      disulfide reductase TRR1 (yTrr1)cytoplasmic thioredoxin
      reductase 1, locus YDR353W

<400> SEQUENCE: 12

Met Val His Asn Lys Val Thr Ile Ile Gly Ser Gly Pro Ala Ala His
1               5                   10                  15

Thr Ala Ala Ile Tyr Leu Ala Arg Ala Glu Ile Lys Pro Ile Leu Tyr
                20                  25                  30

Glu Gly Met Met Ala Asn Gly Ile Ala Ala Gly Gly Gln Leu Thr Thr
            35                  40                  45

Thr Thr Glu Ile Glu Asn Phe Pro Gly Phe Pro Asp Gly Leu Thr Gly
        50                  55                  60

Ser Glu Leu Met Asp Arg Met Arg Glu Gln Ser Thr Lys Phe Gly Thr
65                  70                  75                  80

Glu Ile Ile Thr Glu Thr Val Ser Lys Val Asp Leu Ser Ser Lys Pro
                85                  90                  95
```

```
Phe Lys Leu Trp Thr Glu Phe Asn Glu Asp Ala Glu Pro Val Thr Thr
                100                 105                 110

Asp Ala Ile Ile Leu Ala Thr Gly Ala Ser Ala Lys Arg Met His Leu
            115                 120                 125

Pro Gly Glu Thr Tyr Trp Gln Lys Gly Ile Ser Ala Cys Ala Val
        130                 135                 140

Cys Asp Gly Ala Val Pro Ile Phe Arg Asn Lys Pro Leu Ala Val Ile
145                 150                 155                 160

Gly Gly Gly Asp Ser Ala Cys Glu Glu Ala Gln Phe Leu Thr Lys Tyr
                165                 170                 175

Gly Ser Lys Val Phe Met Leu Val Arg Lys Asp His Leu Arg Ala Ser
            180                 185                 190

Thr Ile Met Gln Lys Arg Ala Glu Lys Asn Glu Lys Ile Glu Ile Leu
        195                 200                 205

Tyr Asn Thr Val Ala Leu Glu Ala Lys Gly Asp Gly Lys Leu Leu Asn
210                 215                 220

Ala Leu Arg Ile Lys Asn Thr Lys Lys Asn Glu Glu Thr Asp Leu Pro
225                 230                 235                 240

Val Ser Gly Leu Phe Tyr Ala Ile Gly His Thr Pro Ala Thr Lys Ile
                245                 250                 255

Val Ala Gly Gln Val Asp Thr Asp Glu Ala Gly Tyr Ile Lys Thr Val
            260                 265                 270

Pro Gly Ser Ser Leu Thr Ser Val Pro Gly Phe Phe Ala Ala Gly Asp
        275                 280                 285

Val Gln Asp Ser Lys Tyr Arg Gln Ala Ile Thr Ser Ala Gly Ser Gly
            290                 295                 300

Cys Met Ala Ala Leu Asp Ala Glu Lys Tyr Leu Thr Ser Leu Glu
305                 310                 315

<210> SEQ ID NO 13
<211> LENGTH: 483
<212> TYPE: PRT
<213> ORGANISM: Saccharomyces cerevisiae
<220> FEATURE:
<223> OTHER INFORMATION: S. cerevisiae strain S288c glutathione-
      disulfide reductase GLR1 (yGl1, GR, GRase), cytosolic and
      mitochondrial glutathione oxidoreductase,
      cytosolic Glr1p, locus YPL091W, LPG17

<400> SEQUENCE: 13

Met Leu Ser Ala Thr Lys Gln Thr Phe Arg Ser Leu Gln Ile Arg Thr
1               5                   10                  15

Met Ser Thr Asn Thr Lys His Tyr Asp Tyr Leu Val Ile Gly Gly Gly
            20                  25                  30

Ser Gly Gly Val Ala Ser Ala Arg Arg Ala Ala Ser Tyr Gly Ala Lys
        35                  40                  45

Thr Leu Leu Val Glu Ala Lys Ala Leu Gly Gly Thr Cys Val Asn Val
    50                  55                  60

Gly Cys Val Pro Lys Lys Val Met Trp Tyr Ala Ser Asp Leu Ala Thr
65                  70                  75                  80

Arg Val Ser His Ala Asn Glu Tyr Gly Leu Tyr Gln Asn Leu Pro Leu
                85                  90                  95

Asp Lys Glu His Leu Thr Phe Asn Trp Pro Glu Phe Lys Gln Lys Arg
            100                 105                 110

Asp Ala Tyr Val His Arg Leu Asn Gly Ile Tyr Gln Lys Asn Leu Glu
        115                 120                 125
```

```
Lys Glu Lys Val Asp Val Val Phe Gly Trp Ala Arg Phe Asn Lys Asp
            130                 135                 140
Gly Asn Val Glu Val Gln Lys Arg Asp Asn Thr Thr Glu Val Tyr Ser
145                 150                 155                 160
Ala Asn His Ile Leu Val Ala Thr Gly Gly Lys Ala Ile Phe Pro Glu
                165                 170                 175
Asn Ile Pro Gly Phe Glu Leu Gly Thr Asp Ser Asp Gly Phe Phe Arg
            180                 185                 190
Leu Glu Glu Gln Pro Lys Lys Val Val Val Gly Ala Gly Tyr Ile
        195                 200                 205
Gly Ile Glu Leu Ala Gly Val Phe His Gly Leu Gly Ser Glu Thr His
210                 215                 220
Leu Val Ile Arg Gly Glu Thr Val Leu Arg Lys Phe Asp Glu Cys Ile
225                 230                 235                 240
Gln Asn Thr Ile Thr Asp His Tyr Val Lys Glu Gly Ile Asn Val His
                245                 250                 255
Lys Leu Ser Lys Ile Val Lys Val Glu Lys Asn Val Glu Thr Asp Lys
            260                 265                 270
Leu Lys Ile His Met Asn Asp Ser Lys Ser Ile Asp Asp Val Asp Glu
        275                 280                 285
Leu Ile Trp Thr Ile Gly Arg Lys Ser His Leu Gly Met Gly Ser Glu
290                 295                 300
Asn Val Gly Ile Lys Leu Asn Ser His Asp Gln Ile Ile Ala Asp Glu
305                 310                 315                 320
Tyr Gln Asn Thr Asn Val Pro Asn Ile Tyr Ser Leu Gly Asp Val Val
                325                 330                 335
Gly Lys Val Glu Leu Thr Pro Val Ala Ile Ala Ala Gly Arg Lys Leu
            340                 345                 350
Ser Asn Arg Leu Phe Gly Pro Glu Lys Phe Arg Asn Asp Lys Leu Asp
        355                 360                 365
Tyr Glu Asn Val Pro Ser Val Ile Phe Ser His Pro Glu Ala Gly Ser
370                 375                 380
Ile Gly Ile Ser Glu Lys Glu Ala Ile Glu Lys Tyr Gly Lys Glu Asn
385                 390                 395                 400
Ile Lys Val Tyr Asn Ser Lys Phe Thr Ala Met Tyr Tyr Ala Met Leu
                405                 410                 415
Ser Glu Lys Ser Pro Thr Arg Tyr Lys Ile Val Cys Ala Gly Pro Asn
            420                 425                 430
Glu Lys Val Val Gly Leu His Ile Val Gly Asp Ser Ser Ala Glu Ile
        435                 440                 445
Leu Gln Gly Phe Gly Val Ala Ile Lys Met Gly Ala Thr Lys Ala Asp
    450                 455                 460
Phe Asp Asn Cys Val Ala Ile His Pro Thr Ser Ala Glu Glu Leu Val
465                 470                 475                 480
Thr Met Arg

<210> SEQ ID NO 14
<211> LENGTH: 432
<212> TYPE: PRT
<213> ORGANISM: Escherichia coli
<220> FEATURE:
<223> OTHER INFORMATION: E. coli strain K-12 substrain MG1655 peptidyl-
      prolyl cis-trans isomerase (PPIase), trigger factor (tig, TF),
      locus b0436, JW0426, ECK0430
```

<400> SEQUENCE: 14

```
Met Gln Val Ser Val Glu Thr Thr Gln Gly Leu Gly Arg Arg Val Thr
 1               5                  10                  15

Ile Thr Ile Ala Ala Asp Ser Ile Glu Thr Ala Val Lys Ser Glu Leu
             20                  25                  30

Val Asn Val Ala Lys Lys Val Arg Ile Asp Gly Phe Arg Lys Gly Lys
         35                  40                  45

Val Pro Met Asn Ile Val Ala Gln Arg Tyr Gly Ala Ser Val Arg Gln
     50                  55                  60

Asp Val Leu Gly Asp Leu Met Ser Arg Asn Phe Ile Asp Ala Ile Ile
 65                  70                  75                  80

Lys Glu Lys Ile Asn Pro Ala Gly Ala Pro Thr Tyr Val Pro Gly Glu
                 85                  90                  95

Tyr Lys Leu Gly Glu Asp Phe Thr Tyr Ser Val Glu Phe Glu Val Tyr
            100                 105                 110

Pro Glu Val Glu Leu Gln Gly Leu Glu Ala Ile Glu Val Glu Lys Pro
        115                 120                 125

Ile Val Glu Val Thr Asp Ala Asp Val Asp Gly Met Leu Asp Thr Leu
130                 135                 140

Arg Lys Gln Gln Ala Thr Trp Lys Glu Lys Asp Gly Ala Val Glu Ala
145                 150                 155                 160

Glu Asp Arg Val Thr Ile Asp Phe Thr Gly Ser Val Asp Gly Glu Glu
                165                 170                 175

Phe Glu Gly Gly Lys Ala Ser Asp Phe Val Leu Ala Met Gly Gln Gly
            180                 185                 190

Arg Met Ile Pro Gly Phe Glu Asp Gly Ile Lys Gly His Lys Ala Gly
        195                 200                 205

Glu Glu Phe Thr Ile Asp Val Thr Phe Pro Glu Glu Tyr His Ala Glu
210                 215                 220

Asn Leu Lys Gly Lys Ala Ala Lys Phe Ala Ile Asn Leu Lys Lys Val
225                 230                 235                 240

Glu Glu Arg Glu Leu Pro Glu Leu Thr Ala Glu Phe Ile Lys Arg Phe
                245                 250                 255

Gly Val Glu Asp Gly Ser Val Glu Gly Leu Arg Ala Glu Val Arg Lys
            260                 265                 270

Asn Met Glu Arg Glu Leu Lys Ser Ala Ile Arg Asn Arg Val Lys Ser
        275                 280                 285

Gln Ala Ile Glu Gly Leu Val Lys Ala Asn Asp Ile Asp Val Pro Ala
    290                 295                 300

Ala Leu Ile Asp Ser Glu Ile Asp Val Leu Arg Arg Gln Ala Ala Gln
305                 310                 315                 320

Arg Phe Gly Gly Asn Glu Lys Gln Ala Leu Glu Leu Pro Arg Glu Leu
                325                 330                 335

Phe Glu Glu Gln Ala Lys Arg Arg Val Val Gly Leu Leu Leu Gly
            340                 345                 350

Glu Val Ile Arg Thr Asn Glu Leu Lys Ala Asp Glu Glu Arg Val Lys
        355                 360                 365

Gly Leu Ile Glu Glu Met Ala Ser Ala Tyr Glu Asp Pro Lys Glu Val
    370                 375                 380

Ile Glu Phe Tyr Ser Lys Asn Lys Glu Leu Met Asp Asn Met Arg Asn
385                 390                 395                 400

Val Ala Leu Glu Glu Gln Ala Val Glu Ala Val Leu Ala Lys Ala Lys
                405                 410                 415
```

```
Val Thr Glu Lys Glu Thr Thr Phe Asn Glu Leu Met Asn Gln Gln Ala
            420                 425                 430
```

<210> SEQ ID NO 15
<211> LENGTH: 216
<212> TYPE: PRT
<213> ORGANISM: Homo sapiens
<220> FEATURE:
<223> OTHER INFORMATION: peptidyl-prolyl cis-trans isomerase B precursor
      (PPIase B, PPIB), rotamase B, cyclophilin B, cyclophilin-like
      protein, S-cyclophilin, epididymis secretory protein Li 39
      (HEL-S-39), SCYLP, CYP-S1, CYPB, OI9

<400> SEQUENCE: 15

```
Met Leu Arg Leu Ser Glu Arg Asn Met Lys Val Leu Ala Ala Ala
 1               5                  10                  15

Leu Ile Ala Gly Ser Val Phe Phe Leu Leu Pro Gly Pro Ser Ala
                20                  25                  30

Ala Asp Glu Lys Lys Lys Gly Pro Lys Val Thr Val Lys Val Tyr Phe
                35                  40                  45

Asp Leu Arg Ile Gly Asp Glu Asp Val Gly Arg Val Ile Phe Gly Leu
 50                  55                  60

Phe Gly Lys Thr Val Pro Lys Thr Val Asp Asn Phe Val Ala Leu Ala
 65                  70                  75                  80

Thr Gly Glu Lys Gly Phe Gly Tyr Lys Asn Ser Lys Phe His Arg Val
                85                  90                  95

Ile Lys Asp Phe Met Ile Gln Gly Gly Asp Phe Thr Arg Gly Asp Gly
                100                 105                 110

Thr Gly Gly Lys Ser Ile Tyr Gly Glu Arg Phe Pro Asp Glu Asn Phe
                115                 120                 125

Lys Leu Lys His Tyr Gly Pro Gly Trp Val Ser Met Ala Asn Ala Gly
            130                 135                 140

Lys Asp Thr Asn Gly Ser Gln Phe Phe Ile Thr Thr Val Lys Thr Ala
145                 150                 155                 160

Trp Leu Asp Gly Lys His Val Val Phe Gly Lys Val Leu Glu Gly Met
                165                 170                 175

Glu Val Val Arg Lys Val Glu Ser Thr Lys Thr Asp Ser Arg Asp Lys
                180                 185                 190

Pro Leu Lys Asp Val Ile Ile Ala Asp Cys Gly Lys Ile Glu Val Glu
            195                 200                 205

Lys Pro Phe Ala Ile Ala Lys Glu
        210                 215
```

<210> SEQ ID NO 16
<211> LENGTH: 162
<212> TYPE: PRT
<213> ORGANISM: Saccharomyces cerevisiae
<220> FEATURE:
<223> OTHER INFORMATION: S. cerevisiae strain S288c peptidyl-prolyl cis-
      trans isomerase (PPIase) CPR1 (Cpr1), rotamase, cyclophilin (CPH,
      CPH1, CYP1), cyclosporin A-binding protein, locusYDR155C,
      PPI-II, SCC1

<400> SEQUENCE: 16

```
Met Ser Gln Val Tyr Phe Asp Val Glu Ala Asp Gly Gln Pro Ile Gly
 1               5                  10                  15

Arg Val Val Phe Lys Leu Tyr Asn Asp Ile Val Pro Lys Thr Ala Glu
                20                  25                  30

Asn Phe Arg Ala Leu Cys Thr Gly Glu Lys Gly Phe Gly Tyr Ala Gly
```

```
                35                  40                  45
Ser Pro Phe His Arg Val Ile Pro Asp Phe Met Leu Gln Gly Gly Asp
 50                  55                  60

Phe Thr Ala Gly Asn Gly Thr Gly Gly Lys Ser Ile Tyr Gly Gly Lys
 65                  70                  75                  80

Phe Pro Asp Glu Asn Phe Lys Lys His His Asp Arg Pro Gly Leu Leu
                 85                  90                  95

Ser Met Ala Asn Ala Gly Pro Asn Thr Asn Gly Ser Gln Phe Phe Ile
                100                 105                 110

Thr Thr Val Pro Cys Pro Trp Leu Asp Gly Lys His Val Val Phe Gly
                115                 120                 125

Glu Val Val Asp Gly Tyr Asp Ile Val Lys Lys Val Glu Ser Leu Gly
            130                 135                 140

Ser Pro Ser Gly Ala Thr Lys Ala Arg Ile Val Val Ala Lys Ser Gly
145                 150                 155                 160

Glu Leu

<210> SEQ ID NO 17
<211> LENGTH: 371
<212> TYPE: PRT
<213> ORGANISM: Saccharomyces cerevisiae
<220> FEATURE:
<223> OTHER INFORMATION: S. cerevisiae strain S288c peptidyl-prolyl
      isomerase (PPIase) CPR6 (Cpr6), rotamase,
      cyclophilin, locusYLR216C, CYP40

<400> SEQUENCE: 17

Met Thr Arg Pro Lys Thr Phe Phe Asp Ile Ser Ile Gly Gly Lys Pro
  1               5                  10                  15

Gln Gly Arg Ile Val Phe Glu Leu Tyr Asn Asp Ile Val Pro Lys Thr
                 20                  25                  30

Ala Glu Asn Phe Leu Lys Leu Cys Glu Gly Asn Ala Gly Met Ala Lys
             35                  40                  45

Thr Lys Pro Asp Val Pro Leu Ser Tyr Lys Gly Ser Ile Phe His Arg
 50                  55                  60

Val Ile Lys Asp Phe Met Cys Gln Phe Gly Asp Phe Thr Asn Phe Asn
 65                  70                  75                  80

Gly Thr Gly Gly Glu Ser Ile Tyr Asp Glu Lys Phe Glu Asp Glu Asn
                 85                  90                  95

Phe Thr Val Lys His Asp Lys Pro Phe Leu Leu Ser Met Ala Asn Ala
                100                 105                 110

Gly Pro Asn Thr Asn Gly Ser Gln Ala Phe Ile Thr Cys Val Pro Thr
            115                 120                 125

Pro His Leu Asp Gly Lys His Val Val Phe Gly Glu Val Ile Gln Gly
            130                 135                 140

Lys Arg Ile Val Arg Leu Ile Glu Asn Gln Gln Cys Asp Gln Glu Asn
145                 150                 155                 160

Asn Lys Pro Leu Arg Asp Val Lys Ile Asp Asp Cys Gly Val Leu Pro
                165                 170                 175

Asp Asp Tyr Gln Val Pro Glu Asn Ala Glu Ala Thr Pro Thr Asp Glu
            180                 185                 190

Tyr Gly Asp Asn Tyr Glu Asp Val Leu Lys Gln Asp Glu Lys Val Asp
            195                 200                 205

Leu Lys Asn Phe Asp Thr Val Leu Lys Ala Ile Glu Thr Val Lys Asn
            210                 215                 220
```

```
Ile Gly Thr Glu Gln Phe Lys Lys Gln Asn Tyr Ser Val Ala Leu Glu
225                 230                 235                 240

Lys Tyr Val Lys Cys Asp Lys Phe Leu Lys Glu Tyr Phe Pro Glu Asp
                245                 250                 255

Leu Glu Lys Glu Gln Ile Glu Lys Ile Asn Gln Leu Lys Val Ser Ile
            260                 265                 270

Pro Leu Asn Ile Ala Ile Cys Ala Leu Lys Leu Lys Asp Tyr Lys Gln
        275                 280                 285

Val Leu Val Ala Ser Ser Glu Val Leu Tyr Ala Gly Ala Ala Asp Glu
    290                 295                 300

Lys Ala Lys Ala Lys Ala Leu Tyr Arg Arg Gly Leu Ala Tyr Tyr His
305                 310                 315                 320

Val Asn Asp Thr Asp Met Ala Leu Asn Asp Leu Glu Met Ala Thr Thr
                325                 330                 335

Phe Gln Pro Asn Asp Ala Ala Ile Leu Lys Ala Ile His Asn Thr Lys
                340                 345                 350

Leu Lys Arg Lys Gln Asn Glu Lys Ala Lys Lys Ser Leu Ser Lys
            355                 360                 365

Met Phe Ser
    370

<210> SEQ ID NO 18
<211> LENGTH: 114
<212> TYPE: PRT
<213> ORGANISM: Saccharomyces cerevisiae
<220> FEATURE:
<223> OTHER INFORMATION: S. cerevisiae strain S288c peptidyl-prolyl
      isomerase (PPIase) FPR1 (Fpr1), FK506-binding protein 1 (FKBP,
      FKB1), nonhistone chromatin binding protein Hmo1p binding protein,
      rapamycin-binding protein (RBP1), locus YNL135C

<400> SEQUENCE: 18

Met Ser Glu Val Ile Glu Gly Asn Val Lys Ile Asp Arg Ile Ser Pro
1               5                   10                  15

Gly Asp Gly Ala Thr Phe Pro Lys Thr Gly Asp Leu Val Thr Ile His
            20                  25                  30

Tyr Thr Gly Thr Leu Glu Asn Gly Gln Lys Phe Asp Ser Ser Val Asp
        35                  40                  45

Arg Gly Ser Pro Phe Gln Cys Asn Ile Gly Val Gly Gln Val Ile Lys
    50                  55                  60

Gly Trp Asp Val Gly Ile Pro Lys Leu Ser Val Gly Glu Lys Ala Arg
65                  70                  75                  80

Leu Thr Ile Pro Gly Pro Tyr Ala Tyr Gly Pro Arg Gly Phe Pro Gly
                85                  90                  95

Leu Ile Pro Pro Asn Ser Thr Leu Val Phe Asp Val Glu Leu Leu Lys
            100                 105                 110

Val Asn

<210> SEQ ID NO 19
<211> LENGTH: 358
<212> TYPE: PRT
<213> ORGANISM: Homo sapiens
<220> FEATURE:
<223> OTHER INFORMATION: DnaJ (Hsp40) homolog subfamily B member 11
      (DNAJB11) precursor, ER-associated dnaJ protein 3 (ERdj3, ERj3p,
      EDJ, ERJ3, ERj3, HEDJ), human DnaJ protein 9 (9HDJ9, DJ9, Dj-9),
      APOBEC1-binding protein 2 (ABBP-2), locus PSEC0121, PRO1080

<400> SEQUENCE: 19
```

```
Met Ala Pro Gln Asn Leu Ser Thr Phe Cys Leu Leu Leu Leu Tyr Leu
 1               5                  10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
50                  55                  60

Glu Lys Phe Gln Asp Leu Gly Ala Ala Tyr Glu Val Leu Ser Asp Ser
65                  70                  75                  80

Glu Lys Arg Lys Gln Tyr Asp Thr Tyr Gly Glu Glu Gly Leu Lys Asp
                85                  90                  95

Gly His Gln Ser Ser His Gly Asp Ile Phe Ser His Phe Phe Gly Asp
                100                 105                 110

Phe Gly Phe Met Phe Gly Gly Thr Pro Arg Gln Gln Asp Arg Asn Ile
            115                 120                 125

Pro Arg Gly Ser Asp Ile Ile Val Asp Leu Glu Val Thr Leu Glu Glu
        130                 135                 140

Val Tyr Ala Gly Asn Phe Val Glu Val Val Arg Asn Lys Pro Val Ala
145                 150                 155                 160

Arg Gln Ala Pro Gly Lys Arg Lys Cys Asn Cys Arg Gln Glu Met Arg
                165                 170                 175

Thr Thr Gln Leu Gly Pro Gly Arg Phe Gln Met Thr Gln Glu Val Val
            180                 185                 190

Cys Asp Glu Cys Pro Asn Val Lys Leu Val Asn Glu Glu Arg Thr Leu
        195                 200                 205

Glu Val Glu Ile Glu Pro Gly Val Arg Asp Gly Met Glu Tyr Pro Phe
210                 215                 220

Ile Gly Glu Gly Glu Pro His Val Asp Gly Glu Pro Gly Asp Leu Arg
225                 230                 235                 240

Phe Arg Ile Lys Val Val Lys His Pro Ile Phe Glu Arg Arg Gly Asp
                245                 250                 255

Asp Leu Tyr Thr Asn Val Thr Ile Ser Leu Val Glu Ser Leu Val Gly
            260                 265                 270

Phe Glu Met Asp Ile Thr His Leu Asp Gly His Lys Val His Ile Ser
        275                 280                 285

Arg Asp Lys Ile Thr Arg Pro Gly Ala Lys Leu Trp Lys Lys Gly Glu
290                 295                 300

Gly Leu Pro Asn Phe Asp Asn Asn Ile Lys Gly Ser Leu Ile Ile
305                 310                 315                 320

Thr Phe Asp Val Asp Phe Pro Lys Glu Gln Leu Thr Glu Glu Ala Arg
                325                 330                 335

Glu Gly Ile Lys Gln Leu Leu Lys Gln Gly Ser Val Gln Lys Val Tyr
            340                 345                 350

Asn Gly Leu Gln Gly Tyr
            355
```

<210> SEQ ID NO 20
<211> LENGTH: 654
<212> TYPE: PRT
<213> ORGANISM: Homo sapiens
<220> FEATURE:
<223> OTHER INFORMATION: 78 kDa glucose-regulated protein (BiP, BIP)
      precursor, ER lumenal Ca(2+)-bindintg protein grp78 (GRP-78), heat
      shock 70 kDa protein 5 (HSPA5), immunoglobulin heavy chain-binding
      protein, epididymis secretory sperm binding protein Li 89n

<400> SEQUENCE: 20

| | | | | | | | | | | | | | | |
|---|---|---|---|---|---|---|---|---|---|---|---|---|---|---|
| Met | Lys | Leu | Ser | Leu | Val | Ala | Ala | Met | Leu | Leu | Leu | Ser | Ala | Ala |
| 1 | | | | 5 | | | | | 10 | | | | | 15 |

| | | | | | | | | | | | | | | |
|---|---|---|---|---|---|---|---|---|---|---|---|---|---|---|
| Arg | Ala | Glu | Glu | Glu | Asp | Lys | Lys | Glu | Asp | Val | Gly | Thr | Val | Gly |
| | | | | 20 | | | | | 25 | | | | | 30 |

| | | | | | | | | | | | | | | |
|---|---|---|---|---|---|---|---|---|---|---|---|---|---|---|
| Ile | Asp | Leu | Gly | Thr | Thr | Tyr | Ser | Cys | Val | Gly | Val | Phe | Lys | Asn | Gly |
| | | | | 35 | | | | | 40 | | | | | 45 |

Arg Val Glu Ile Ile Ala Asn Asp Gln Gly Asn Arg Ile Thr Pro Ser
     50                  55                  60

Tyr Val Ala Phe Thr Pro Glu Gly Glu Arg Leu Ile Gly Asp Ala Ala
 65                  70                  75                  80

Lys Asn Gln Leu Thr Ser Asn Pro Glu Asn Thr Val Phe Asp Ala Lys
                 85                  90                  95

Arg Leu Ile Gly Arg Thr Trp Asn Asp Pro Ser Val Gln Gln Asp Ile
                100                 105                 110

Lys Phe Leu Pro Phe Lys Val Val Glu Lys Thr Lys Pro Tyr Ile
            115                 120                 125

Gln Val Asp Ile Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
                180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu

```
                    405                 410                 415
Leu Asp Val Cys Pro Leu Thr Leu Gly Ile Glu Thr Val Gly Gly Val
            420                 425                 430

Met Thr Lys Leu Ile Pro Arg Asn Thr Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
        500                 505                 510

Ala Glu Asp Lys Gly Thr Gly Asn Lys Asn Lys Ile Thr Ile Thr Asn
    515                 520                 525

Asp Gln Asn Arg Leu Thr Pro Glu Glu Ile Glu Arg Met Val Asn Asp
530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575

Gly Asp Lys Glu Lys Leu Gly Gly Lys Leu Ser Ser Glu Asp Lys Glu
        580                 585                 590

Thr Met Glu Lys Ala Val Glu Glu Lys Ile Glu Trp Leu Glu Ser His
    595                 600                 605

Gln Asp Ala Asp Ile Glu Asp Phe Lys Ala Lys Lys Lys Glu Leu Glu
610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
            645                 650
```

<210> SEQ ID NO 21
<211> LENGTH: 705
<212> TYPE: PRT
<213> ORGANISM: Saccharomyces cerevisiae
<220> FEATURE:
<223> OTHER INFORMATION: S. cerevisiae strain S288c 82 kDa heat shock cognate protein, heat shock protein Hsp90 constitutive isoform (HSP90), Hsp90 family chaperone HSC82, ATP-dependent molecular chaperone HSC82, cytoplasmic chaperone of the Hsp90 family, locus YMR186W

<400> SEQUENCE: 21

```
Met Ala Gly Glu Thr Phe Glu Phe Gln Ala Glu Ile Thr Gln Leu Met
1               5                   10                  15

Ser Leu Ile Ile Asn Thr Val Tyr Ser Asn Lys Glu Ile Phe Leu Arg
            20                  25                  30

Glu Leu Ile Ser Asn Ala Ser Asp Ala Leu Asp Lys Ile Arg Tyr Gln
        35                  40                  45

Ala Leu Ser Asp Pro Lys Gln Leu Glu Thr Glu Pro Asp Leu Phe Ile
    50                  55                  60

Arg Ile Thr Pro Lys Pro Glu Glu Lys Val Leu Glu Ile Arg Asp Ser
65                  70                  75                  80

Gly Ile Gly Met Thr Lys Ala Glu Leu Ile Asn Asn Leu Gly Thr Ile
            85                  90                  95
```

-continued

```
Ala Lys Ser Gly Thr Lys Ala Phe Met Glu Ala Leu Ser Ala Gly Ala
            100                 105                 110

Asp Val Ser Met Ile Gly Gln Phe Gly Val Gly Phe Tyr Ser Leu Phe
            115                 120                 125

Leu Val Ala Asp Arg Val Gln Val Ile Ser Lys Asn Asn Glu Asp Glu
        130                 135                 140

Gln Tyr Ile Trp Glu Ser Asn Ala Gly Gly Ser Phe Thr Val Thr Leu
145                 150                 155                 160

Asp Glu Val Asn Glu Arg Ile Gly Arg Gly Thr Val Leu Arg Leu Phe
                165                 170                 175

Leu Lys Asp Asp Gln Leu Glu Tyr Leu Glu Glu Lys Arg Ile Lys Glu
            180                 185                 190

Val Ile Lys Arg His Ser Glu Phe Val Ala Tyr Pro Ile Gln Leu Leu
        195                 200                 205

Val Thr Lys Glu Val Glu Lys Glu Val Pro Ile Pro Glu Glu Glu Lys
        210                 215                 220

Lys Asp Glu Glu Lys Lys Asp Glu Asp Lys Lys Pro Lys Leu Glu
225                 230                 235                 240

Glu Val Asp Glu Glu Glu Glu Glu Lys Lys Pro Lys Thr Lys Lys Val
                245                 250                 255

Lys Glu Glu Val Gln Glu Leu Glu Glu Leu Asn Lys Thr Lys Pro Leu
            260                 265                 270

Trp Thr Arg Asn Pro Ser Asp Ile Thr Gln Glu Glu Tyr Asn Ala Phe
                275                 280                 285

Tyr Lys Ser Ile Ser Asn Asp Trp Glu Asp Pro Leu Tyr Val Lys His
            290                 295                 300

Phe Ser Val Glu Gly Gln Leu Glu Phe Arg Ala Ile Leu Phe Ile Pro
305                 310                 315                 320

Lys Arg Ala Pro Phe Asp Leu Phe Glu Ser Lys Lys Lys Asn Asn
                325                 330                 335

Ile Lys Leu Tyr Val Arg Arg Val Phe Ile Thr Asp Glu Ala Glu Asp
            340                 345                 350

Leu Ile Pro Glu Trp Leu Ser Phe Val Lys Gly Val Val Asp Ser Glu
        355                 360                 365

Asp Leu Pro Leu Asn Leu Ser Arg Glu Met Leu Gln Gln Asn Lys Ile
        370                 375                 380

Met Lys Val Ile Arg Lys Asn Ile Val Lys Lys Leu Ile Glu Ala Phe
385                 390                 395                 400

Asn Glu Ile Ala Glu Asp Ser Glu Gln Phe Asp Lys Phe Tyr Ser Ala
                405                 410                 415

Phe Ala Lys Asn Ile Lys Leu Gly Val His Glu Asp Thr Gln Asn Arg
            420                 425                 430

Ala Ala Leu Ala Lys Leu Leu Arg Tyr Asn Ser Thr Lys Ser Val Asp
        435                 440                 445

Glu Leu Thr Ser Leu Thr Asp Tyr Val Thr Arg Met Pro Glu His Gln
        450                 455                 460

Lys Asn Ile Tyr Tyr Ile Thr Gly Glu Ser Leu Lys Ala Val Glu Lys
465                 470                 475                 480

Ser Pro Phe Leu Asp Ala Leu Lys Ala Lys Asn Phe Glu Val Leu Phe
                485                 490                 495

Leu Thr Asp Pro Ile Asp Glu Tyr Ala Phe Thr Gln Leu Lys Glu Phe
            500                 505                 510

Glu Gly Lys Thr Leu Val Asp Ile Thr Lys Asp Phe Glu Leu Glu Glu
```

```
                515                 520                 525
Thr Asp Glu Glu Lys Ala Glu Arg Glu Lys Glu Ile Lys Glu Tyr Glu
530                 535                 540

Pro Leu Thr Lys Ala Leu Lys Asp Ile Leu Gly Asp Gln Val Glu Lys
545                 550                 555                 560

Val Val Val Ser Tyr Lys Leu Leu Asp Ala Pro Ala Ala Ile Arg Thr
                565                 570                 575

Gly Gln Phe Gly Trp Ser Ala Asn Met Glu Arg Ile Met Lys Ala Gln
                580                 585                 590

Ala Leu Arg Asp Ser Ser Met Ser Ser Tyr Met Ser Ser Lys Lys Thr
                595                 600                 605

Phe Glu Ile Ser Pro Lys Ser Pro Ile Ile Lys Glu Leu Lys Lys Arg
                610                 615                 620

Val Asp Glu Gly Gly Ala Gln Asp Lys Thr Val Lys Asp Leu Thr Asn
625                 630                 635                 640

Leu Leu Phe Glu Thr Ala Leu Leu Thr Ser Gly Phe Ser Leu Glu Glu
                645                 650                 655

Pro Thr Ser Phe Ala Ser Arg Ile Asn Arg Leu Ile Ser Leu Gly Leu
                660                 665                 670

Asn Ile Asp Glu Asp Glu Glu Thr Glu Thr Ala Pro Glu Ala Ser Thr
                675                 680                 685

Glu Ala Pro Val Glu Glu Val Pro Ala Asp Thr Glu Met Glu Glu Val
690                 695                 700

Asp
705

<210> SEQ ID NO 22
<211> LENGTH: 137
<212> TYPE: PRT
<213> ORGANISM: Escherichia coli
<220> FEATURE:
<223> OTHER INFORMATION: E. coli strain K-12 substrain MG1655 heat shock
      chaperone, small heat shock protein IbpA, 16 kDa
      heat shock protein A, locus b3687, JW3664, hsIT,
      htpN, ECK3679

<400> SEQUENCE: 22

Met Arg Asn Phe Asp Leu Ser Pro Leu Tyr Arg Ser Ala Ile Gly Phe
1               5                   10                  15

Asp Arg Leu Phe Asn His Leu Glu Asn Asn Gln Ser Gln Ser Asn Gly
                20                  25                  30

Gly Tyr Pro Pro Tyr Asn Val Glu Leu Val Asp Glu Asn His Tyr Arg
                35                  40                  45

Ile Ala Ile Ala Val Ala Gly Phe Ala Glu Ser Glu Leu Glu Ile Thr
50                  55                  60

Ala Gln Asp Asn Leu Leu Val Val Lys Gly Ala His Ala Asp Glu Gln
65                  70                  75                  80

Lys Glu Arg Thr Tyr Leu Tyr Gln Gly Ile Ala Glu Arg Asn Phe Glu
                85                  90                  95

Arg Lys Phe Gln Leu Ala Glu Asn Ile His Val Arg Gly Ala Asn Leu
                100                 105                 110

Val Asn Gly Leu Leu Tyr Ile Asp Leu Glu Arg Val Ile Pro Glu Ala
                115                 120                 125

Lys Lys Pro Arg Arg Ile Glu Ile Asn
130                 135
```

```
<210> SEQ ID NO 23
<211> LENGTH: 142
<212> TYPE: PRT
<213> ORGANISM: Escherichia coli
<220> FEATURE:
<223> OTHER INFORMATION: E. coli strain K-12 substrain MG1655 heat shock
      chaperone, small heat shock protein IbpB, 16 kDa
      heat shock protein B, locus b3686, JW3663, hsIS,
      htpE, ECK3678

<400> SEQUENCE: 23

Met Arg Asn Phe Asp Leu Ser Pro Leu Met Arg Gln Trp Ile Gly Phe
1               5                   10                  15

Asp Lys Leu Ala Asn Ala Leu Gln Asn Ala Gly Glu Ser Gln Ser Phe
            20                  25                  30

Pro Pro Tyr Asn Ile Glu Lys Ser Asp Asp Asn His Tyr Arg Ile Thr
        35                  40                  45

Leu Ala Leu Ala Gly Phe Arg Gln Glu Asp Leu Glu Ile Gln Leu Glu
    50                  55                  60

Gly Thr Arg Leu Ser Val Lys Gly Thr Pro Glu Gln Pro Lys Glu Glu
65                  70                  75                  80

Lys Lys Trp Leu His Gln Gly Leu Met Asn Gln Pro Phe Ser Leu Ser
                85                  90                  95

Phe Thr Leu Ala Glu Asn Met Glu Val Ser Gly Ala Thr Phe Val Asn
            100                 105                 110

Gly Leu Leu His Ile Asp Leu Ile Arg Asn Glu Pro Glu Pro Ile Ala
        115                 120                 125

Ala Gln Arg Ile Ala Ile Ser Glu Arg Pro Ala Leu Asn Ser
    130                 135                 140

<210> SEQ ID NO 24
<211> LENGTH: 6
<212> TYPE: PRT
<213> ORGANISM: Artificial Sequence
<220> FEATURE:
<223> OTHER INFORMATION: synthetic polyhistidine, His-6, 6xHis tag,
      poly-amino acid tag

<400> SEQUENCE: 24

His His His His His His
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic poly-amino acid tag

<400> SEQUENCE: 25

Ser Arg Ser Arg Ser Arg Ser Arg
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic poly-amino acid tag

<400> SEQUENCE: 26

Ser Lys Ser Lys Ser Lys Ser Lys
1               5
```

```
<210> SEQ ID NO 27
<211> LENGTH: 6
<212> TYPE: PRT
<213> ORGANISM: Artificial Sequence
<220> FEATURE:
<223> OTHER INFORMATION: synthetic poly-amino acid tag

<400> SEQUENCE: 27

Asp Asp Asp Asp Asp Asp
1               5

<210> SEQ ID NO 28
<211> LENGTH: 6
<212> TYPE: PRT
<213> ORGANISM: Artificial Sequence
<220> FEATURE:
<223> OTHER INFORMATION: synthetic poly-amino acid tag

<400> SEQUENCE: 28

Glu Glu Glu Glu Glu Glu
1               5

<210> SEQ ID NO 29
<211> LENGTH: 4
<212> TYPE: PRT
<213> ORGANISM: Artificial Sequence
<220> FEATURE:
<223> OTHER INFORMATION: synthetic DsbC active site

<400> SEQUENCE: 29

Cys Gly Tyr Cys
1
```

EXPRESSION OF BIOLOGICALLY ACTIVE PROTEINS IN A BACTERIAL CELL-FREE SYNTHESIS SYSTEM USING BACTERIAL CELLS TRANSFORMED TO EXHIBIT ELEVATED LEVELS OF CHAPERONE EXPRESSION

CROSS-REFERENCES TO RELATED APPLICATIONS

This application claims benefit of priority to U.S. Patent Application No. 61/813,914, filed Apr. 19, 2013, and U.S. Patent Application No. 61/937,069, filed Feb. 7, 2014, the disclosure of each of which is incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-58-2.TXT, created on Apr. 3, 2014, 73,728 bytes, machine format IBM-PC, MS-Windows operating system, is hereby incorporated by reference in its entirety for all purposes.

BACKGROUND OF THE INVENTION

The expression of proteins in bacterial cell free synthesis systems is a well established technique for expressing recombinant target proteins. Extracts can be made from bacteria expressing or overexpressing proteins of interest to provide bacterial cell free synthesis systems having altered properties depending on the protein. However, overexpression of proteins during bacterial growth frequently results in slower growth rates for the bacteria and lower protein synthetic activity in extracts prepared from the bacteria.

Further, expression of recombinant proteins from such extracts often leads to improper folding and loss of biological activity. The use of protein chaperones can improve the proper folding and biological activity of proteins Thus, there remains a need for improved bacterial cell extracts for expressing recombinant proteins that are prepared from bacteria overexpressing chaperones where such extracts can synthesize large amounts of properly folded protein. These and other needs are provided by the present invention, as set forth below.

BRIEF SUMMARY OF THE INVENTION

The present disclosure provides methods and systems for improving the expression of biologically active and/or properly folded proteins of interest in a cell free synthesis system. The cell free synthesis system comprises a bacterial extract having an active oxidative phosphorylation system and the components necessary for cell free protein synthesis. The cell free synthesis system further comprises an exogenous protein chaperone. In some embodiments, the exogenous protein chaperone is expressed by the bacteria used to prepare the bacterial extract.

Thus, in one aspect, a method of improving the expression levels of biologically active proteins in a bacterial cell free synthesis system is described, the method comprising the steps of:
i) preparing a bacterial extract having an active oxidative phosphorylation system and comprising biologically functioning tRNA, amino acids and ribosomes necessary for cell free protein synthesis, wherein the bacteria from which the extract is prepared expresses an exogenous protein chaperone at a concentration of at least about 1 gm/liter of extract;
ii) combining the bacterial extract with a nucleic acid encoding a protein of interest to yield a bacterial cell free synthesis system; and,
iii) incubating the bacterial cell free synthesis system under conditions permitting the expression of the protein of interest to a concentration of at least about 100 mg/L.

In a second aspect, a bacterial cell free synthesis system for expressing biologically active proteins is described, the system comprising:
i) a cell free extract of bacteria having an active oxidative phosphorylation system, containing biologically functioning tRNA, amino acids and ribosomes necessary for cell free protein synthesis and wherein an exogenous protein chaperone was expressed in the bacteria at a level of at least 1 gm/liter of extract; and,
ii) a nucleic acid encoding a protein of interest,
where said bacterial cell free synthesis system expresses a protein of interest to a concentration of at least about 100 mg/L.

In a third aspect, a method of expressing properly folded, biologically active proteins in a bacterial cell free synthesis system is described, the method comprising the steps of:
i) preparing a bacterial extract comprising biologically functioning tRNA, amino acids, ribosomes necessary for cell free protein synthesis, a protein disulfide isomerase and a peptidyl-prolyl cis/trans isomerase, wherein the protein disulfide isomerase and the peptidyl-prolyl cis/trans isomerase are present at a concentration sufficient to improve the expression of properly folded biologically active proteins;
ii) combining the bacterial extract with a nucleic acid encoding a protein of interest; and
iii) incubating the bacterial extract with the nucleic acid under conditions permitting the expression and proper folding of the protein of interest.

In a fourth aspect, a bacterial cell free synthesis system for expressing biologically active proteins is described, the system comprising:
i) a cell free extract of bacteria having an active oxidative phosphorylation system, containing biologically functioning tRNA, amino acids and ribosomes necessary for cell free protein synthesis and further including protein disulfide isomerase and a peptidyl-prolyl cis/trans isomerase,
wherein the protein disulfide isomerase and the peptidyl-prolyl cis/trans isomerase are present at a concentration sufficient to improve the expression of properly folded biologically active proteins; and
ii) a nucleic acid encoding a protein of interest,
wherein said bacterial cell free synthesis system expresses a protein of interest to a concentration of at least about 100 mg/L.

In a fifth aspect, a method of improving the vitality and/or growth rate of an *E coli* cell culture is described, the method comprising the steps of:
i) transforming an *E. coli* cell with a nucleic acid expressing the protein DsbC operably linked to a constitutive promoter; and
ii) culturing the transformed *E. coli* cell under conditions that permit the overexpression of the DsbC protein to an intracellular concentration of at least 1 mg/ml.

DEFINITIONS

Figure 1:
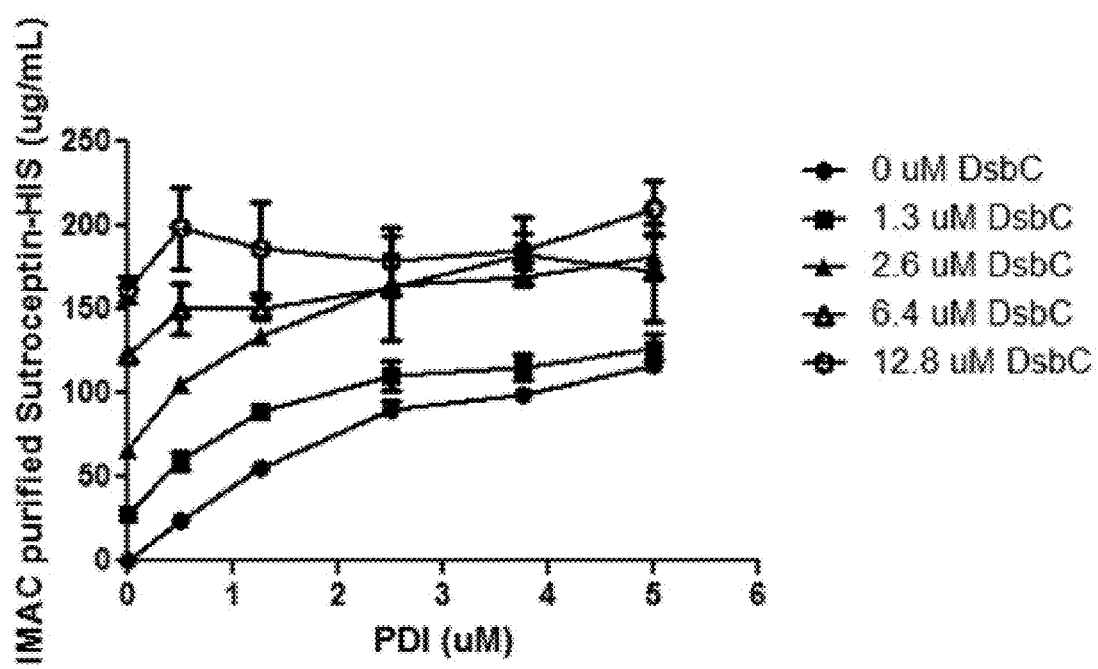
FIG. 1 shows that eukaryotic PDI and bacterial DsbC are functionally interchangeable.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989); Ausubel et al., CURRENT PROTOCOLS IN MOLECULAR BIOLOGY, John Wiley and Sons (Hoboken, N.Y. 1995). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "active oxidative phosphorylation system" refers to a bacterial lysate that exhibits active oxidative phosphorylation during protein synthesis. For example, the bacterial lysate can generate ATP using ATP synthase enzymes and reduction of oxygen. It will be understood that other translation systems known in the art can also use an active oxidative phosphorylation during protein synthesis. The activation of oxidative phosphorylation can be demonstrated by inhibition of the pathway using specific inhibitors, such as electron transport chain inhibitors.

The term "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab)$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), and single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) *Proc. Nat. Acad. Sci. USA*, 85: 5879-5883. While the VH and VL are connected to each as a single polypeptide chain, the VH and VL domains associate non-covalently. The first functional antibody molecules to be expressed on the surface of filamentous phage were single-chain Fv's (scFv); however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see, e.g., U.S. Pat. Nos. 5,091,513, 5,132,405, and 4,956,778). Antibodies also includes all those that have been displayed on phage (e.g., scFv, Fv, Fab and disulfide linked Fv (Reiter et al. (1995) Protein Eng. 8: 1323-1331). Antibodies can also include diantibodies, miniantibodies and scFv-Fc fusions.

The term "bacterial derived cell free extract" refers to preparation of in vitro reaction mixtures able to transcribe DNA into mRNA and/or translate mRNA into polypeptides. The mixtures include ribosomes, ATP, amino acids, and tRNAs. They may be derived directly from lysed bacteria, from purified components or combinations of both.

The term "bacterial cell free synthesis system" refers to the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with unnatural amino acids, polymerases, transcriptional factors, tRNA synthetases, etc.

The term "biologically active protein" refers to a protein that retains at least some of the biological activity of the protein of interest. The biological activity can be determined by comparing the activity, function and/or structure of the protein of interest expressed by the methods described herein to the activity of a reference protein of interest. For example, if the reference protein of interest is an IgG, a biologically active protein will comprise a properly folded and assembled IgG molecule. In some embodiments, the reference protein can be a protein expressed by a bacterial cell free synthesis system that does not contain an exogenous protein chaperone. The biological activity can also be determined using an in vitro or in vivo assay that is appropriate for the protein of interest. The biological activity of the protein of interest can be expressed as the biological activity per unit volume of the cell-free protein synthesis reaction mixture. In some embodiments, the biological activity of a protein produced by the methods described herein is at least 30%, 40%, 50%, 60%, 70%, 80%, 90%, 95% or 99% of the activity of a reference protein.

The term "constitutive promoter" refers to a nucleic acid sequence that, under appropriate conditions, allows for continual transcription of a nucleic acid sequence or gene that is operably connected or linked to the promoter sequence. The appropriate conditions include transcription factors, such as RNA polymerase, that bind to the promoter sequence, and ribonucleotides that are incorporated into the transcribed RNA. Constitutive promoters are typically unregulated promoters in that they promote continual transcription under normal cellular conditions.

The term "disulfide isomerase" or "protein disulfide isomerase" (PDI) refers to a family of proteins comprising multiple domains, each having a typical thioredoxin (Trx) fold. The PDI molecule has two or more active sites comprising a COX motif that are the sites for isomerase activity. In vitro, PDI catalyzes the oxidative formation, reduction, or isomerization of disulfide bonds depending on the redox potential of the environment. PDIs are members of a class of folding catalysts, also called foldases. Folding catalysts assist folding by accelerating certain rate-limiting steps in the protein folding process, thereby reducing the concentration of aggregated protein folding intermediates. In addition to the isomerase function of catalyzing the formation of disulfide bonds, PDI also promotes the folding of polypeptides into their native configuration, and thus acts as a chaperone. The C-terminal region of PDI comprises the polypeptide binding region, and is believed to be responsible for the chaperone activity. The isomerase and chaperone activities of PDI are separate and independent activities, and both activities appear to be required for reactivation of reduced and denatured proteins containing disulfide bonds.

In gram-negative bacteria, disulfide bond formation, reduction and isomerization are catalyzed by the Dsb (disulfide bond formation) family of proteins, including DsbA, DsbB, DsbC, and DsbD. DsbA catalyzes the oxidative formation of disulfide bonds by transferring its active site disulfide to the target protein, which leaves DsbA in a reduced form. DsbB re-oxidizes DsbA, and passes its electrons to the respiratory chain to regenerate oxidized DsbB. DsbC catalyzes the rearrangement of disulfide bonds and is recognized as a counterpart of eukaryotic PDI. DsbC is maintained in its reduced form by DsbD. DsbC is a homodimer having four thiol groups is each 23 kDa subunit monomer, two in the active site-$Cys^{98}$-Gly-Tyr-$Cys^{101}$ (SEQ ID NO:29), and the other two a $Cys^{141}$ and $Cys^{163}$. Similar to PDI, DsbC has chaperone activity that is independent from its isomerase activity. (See, e.g., Chen et al., *J. Biol. Chem.* 274:19601-19605, 1999; and Kolag, O., et al., *Microbial Cell Factories*, 2009, 8:9). Each monomer consists of an N-terminal dimerization domain with a cystatin fold and a C-terminal catalytic domain with a thioredoxin fold (McCarthy A. A., et al., *Nat. Struct. Biol.* 7:196-199, 2000). Other Dsb proteins include DsbE abd DsbG.

The term "exogenous protein chaperone" generally refers to a protein chaperone (e.g., a recombinant protein chaperone) that is not normally expressed by the bacterial strain used to prepare the bacterial extract, or a recombinant protein chaperone that is expressed by a nucleic acid construct that is not present in the native bacterial strain. For example, if the native bacterial strain used to prepare the bacterial extract naturally expresses low levels of the endogenous protein chaperone (e.g., at levels not sufficient to improve the expression levels of a biologically active protein of interest), the exogenous protein chaperone can be expressed from a non-native nucleic acid construct, such that the nucleic acid sequences encoding the exogenous protein chaperone are under the control of different regulatory sequences than the endogenous sequences encoding the chaperone. For example, the protein chaperones DsbC and FkpA are naturally occurring *E. coli* proteins, but their expression levels are below the limit of detection using the ELISA assays described herein to detect proteins in bacterial extracts. Thus, the term "exogenous" is synonymous with "heterologous," which refers to a protein chaperone not normally expressed by the bacterial strain used to prepare the bacterial extract, or a nucleic acid encoding the protein chaperone that is not present in the native bacterial strain. In some embodiments, the term refers to recombinant protein chaperones that are added to a bacterial cell free extract, and thus are not expressed by the bacteria from which the extract was made.

The terms "identical," "essentially identical" or percent "identity," in the context of two or more nucleic acids or polypeptide sequences, refer to two or more sequences or subsequences that are the same or have a specified percentage of nucleotides or amino acid residues that are the same (e.g., 60%, 65%, 70%, 75%, 80%, 85%, 90%, 95%, 96%, 97%, 98% or 99% identity over a specified region), when compared and aligned for maximum correspondence over a comparison window, or designated region, as measured using the BLAST and PSI-BLAST algorithms, which are described in Altschul et al. (*J. Mol. Biol.* 215:403-10, 1990), and Altschul et al. (*Nucleic Acids Res.*, 25:3389-3402, 1997), respectively. Software for performing BLAST analyses is publicly available through the National Center for Biotechnology Information (see the internet at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, an expectation (E) of 10, and the BLOSUM62 scoring matrix (see Henikoff and Henikoff, *Proc. Natl. Acad. Sci. USA* 89:10915-10919, 1992).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well-known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using the algorithm described in Pearson et al. (*Meth. Mol. Biol.* 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical (e.g., at least 80%, 85%, 90%, 95%, 96%, 97%, 98% or 99% identity over a specified region) amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein.

Furthermore, it will be recognized that individual substitutions, deletions or additions that alter, add or delete a single amino acid or a small percentage of amino acids (typically less than 10%, and generally less than 1%) in an encoded sequence can be considered conservatively modified variations, provided the alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K)
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially similar" if the amino acid sequences or the nucleotide sequences share at least 60%, 65%, 70%, 75%, 80%, 85%, 90%, 95%, 96%, 97%, 98% or 99% sequence identity with each other, or with a reference sequence over a given comparison window. Two or more proteins are also considered substantially similar if they incorporate conservative amino acid substitutions providing functionally similar amino acids into the amino acid sequence.

The term "incubation conditions are otherwise the same" refers to experimental conditions that, for comparison purposes, are the same except that the control or reference extract does not contain or express an exogenous protein chaperone. The term also includes a comparison between a control extract that expresses or contains one class of exogenous protein chaperone (e.g., a PDI) and an extract that expresses or contains two different classes of exogenous protein chaperones (e.g., a PDI and a PPIase). For example, the extract can be prepared from a bacterial strain that expresses or overexpresses one class of protein chaperone (e.g., a PDI or DsbC) and a purified protein from the other class of protein chaperone (e.g., a purified PPIase such as FkpA) can be added to the extract. The conditions can also include adjusting the total concentration of the exogenous protein chaperones (e.g., the total concentration of one chaperone such as PDI, or the total concentration of the combination of two different chaperones, such as PDI and PPI) in the bacterial extract to be the same. Otherwise, the components of the bacterial extract and the nucleic acid encoding the protein of interest are the same. Exemplary conditions that permit the expression and proper folding of a protein of interest are described in the Examples.

The terms "peptidyl prolyl isomerase," "peptidyl prolyl cis-trans isomerase" and "prolyl isomerase" (PPI or PPIase) are used interchangeably, and refer to a class of chaperones known as protein folding catalysts. PPI catalyzes the conversion of trans peptidyl prolyl bonds in the amino acid proline to the cis configuration in the native or functional protein. PPIs can have different subunits or modules having different functions, for example, a module having catalytic activity and a module having chaperone or protein binding activity. Three families of PPIs are recognized: cyclophilins (whose isomerase activity is inhibited by cyclosporin A); FKBPs (FK506 binding proteins), which are inhibited by FK506 and rapamycin; and parvulins. Non-limiting examples of cyclophilins include PpiA (RotA). Non-limiting examples of FKBPs include FkpA, SlyD, and trigger factor (TF or tig). Non-limiting examples of parvulins include SurA and PpiD. Additional examples of PPIs include CypA, PpiB, Cpr1, Cpr6, and Fpr1. FkpA, SlyD, and trigger factor are related based on sequence alignments. For FkpA, the chaperone and catalytic activities reside in the N-terminal and C-terminal domains, respectively (Saul F. A., *J. Mol. Biol.* 335:595-608, 2004).

The term "deaggregase" refers to a protein chaperone that aids in deaggregating and/or solubilizing proteins of interest that are produced, for example, in a bacterial free translation system. Such chaperones are particularly helpful at high concentrations because their mechanism of action is stoichiometric rather than catalytic and is believed to work by stabilizing hydrophobic patches of the newly synthesized protein while the protein is folding. Examples of deaggregases include IbpA, IbpB, and Skp.

The term "peptide," "protein," and "polypeptide" are used herein interchangeably and refer to a to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins and truncated proteins, wherein the amino acid residues are linked by covalent peptide bonds.

The term "properly folded protein" refers to the native conformation of a protein or polypeptide that is biologically active or functional. Thus, the term refers to a protein or polypeptide having a tertiary structure that in the folded state possesses a minimum of free energy. When used in reference to a recombinant protein expressed in bacteria, the term generally refers to proteins that are soluble when overexpressed in the cytosol, such that the properly folded recombinant protein does not form insoluble aggregates and/or is not denatured or unfolded.

The term "synergistic" or "synergy" interchangeably refers to the interaction of two or more agents so that their combined effect is greater than the sum of their individual effects. Synergistic drug interactions can be determined using the median effect principle (see, Chou and Talalay (1984) *Adv Enzyme Regul* 22:27 and *Synergism and Antagonism in Chemotherapy*, Chou and Rideout, eds., 1996, Academic, pp. 61-102) and quantitatively determined by combination indices using the computer program Calcusyn (Chou and Hayball, 1996, Biosoft, Cambridge, Mass.). See also, Reynolds and Maurer, Chapter 14 in *Methods in Molecular in Medicine*, vol. 110: *Chemosensitivity*, Vol. 1: *In vitro Assays*, Blumenthal, ed., 2005, Humana Press. Combination indices (CI) quantify synergy, summation and antagonism as follows: CI<1 (synergy); CI=1 (summation);

CI>1 (antagonism). A CI value of 0.7-0.9 indicates moderate to slight synergism. A CI value of 0.3-0.7 indicates synergism. A CI value of 0.1-0.3 indicates strong synergism. A CI value of <0.1 indicates very strong synergism.

DETAILED DESCRIPTION OF THE INVENTION

Introduction

The methods and systems described herein are useful for improving and/or increasing the expression levels of biologically active proteins in a cell free synthesis system, for example a bacterial cell free synthesis system. The increased expression levels of a biologically active protein of interest are achieved by using a bacterial extract having an active oxidative phosphorylation system that comprises an exogenous protein chaperone. The exogenous protein chaperone can be expressed by the bacteria used to prepare the extract. The inventors have surprisingly discovered that by expressing relatively large amounts of an exogenous protein chaperone in the bacteria used to prepare the extract, increased amounts of the biologically active protein of interest are expressed by the cell free synthesis system. Thus, the ability of the extract to express large amounts of protein is surprisingly not adversely affected by the relatively high concentration levels of the protein chaperone, such that the total amount of properly folded and biologically active protein produced in the cell free protein synthesis reaction is substantially higher than the amount of properly folded and biologically active protein expressed by a cell free synthesis system that does not contain an exogenous protein chaperone. Thus, while the total amount of the protein of interest produced by the cell free protein synthesis system is substantially similar to the total amount of protein produced by a cell free protein synthesis system that does not express an exogenous chaperone, the increased concentration levels of protein chaperone in the extract results in increased amounts of properly folded, assembled, and biologically active protein of interest. The inventors have also surprisingly discovered that by expressing two different classes of protein chaperones (e.g., a protein disulfide isomerase and a peptidyl prolyl cis-trans isomerase), a synergistic improvement in the expression levels of properly folded, biologically active proteins is obtained. The methods and systems will now be described.

To produce a biologically active protein of interest, the methods and systems described herein use a bacterial extract having an active oxidative phosphorylation system, and other components necessary for cell free protein synthesis, such as biologically functioning tRNA, amino acids and ribosomes. The components of the bacterial extract are described in more detail below. In one aspect, the bacterial extract is prepared from a recombinant bacteria that expresses an exogenous protein chaperone. In some embodiments, the bacteria from which the extract is prepared express the exogenous protein chaperone at a concentration of at least about 1 gram (g)/liter (L) of extract. For example, the bacteria from which the extract is prepared can express the exogenous protein chaperone at a concentration of at least about 1 g/liter, 2 g/liter, 3 g/liter, 4 g/liter, 5 g/liter, 6 g/liter, 7 g/liter, 8 g/liter, 9 g/liter, 10 g/liter or more of extract. In some embodiments, the total concentration of exogenous protein chaperone is between about 1 g/L and 20 g/L, between about 1 g/L and 15 g/L, between about 1 g/L and 10 g/L, or between about 1 g/L and 5 g/L of extract. In some embodiments, the bacteria express the exogenous protein chaperone at an intracellular concentration of at least 1 mg/ml, at least 2 mg/ml, at least 3 mg/ml, at least 4 mg/ml, at least 5 mg/ml, at least 10 mg/ml, at least 15 mg/ml, at least 20 mg/ml, at least 30 mg/ml, or at least 40 mg/ml. In some embodiments, the bacteria express the exogenous protein chaperone at an intracellular concentration in the range of about 1 mg/ml to about 40 mg/ml, about 1 mg/ml to about 20 mg/ml, about 1 mg/ml to about 15 mg/ml, about 1 mg/ml to about 10 mg/ml, or about 1 mg/ml to about 5 mg/ml.

The exogenous protein chaperone can be any protein chaperone that results in increased production of properly folded and/or biologically functional proteins of interest. As described in more detail herein, the protein chaperone can be a protein that interacts with the target protein of interest to assist in proper folding and/or prevent aggregation of the protein of interest into nonfunctional aggregates. While not being bound by theory, molecular chaperones are thought to prevent aggregation by binding exposed hydrophobic moieties in unfolded, partially folded, or misfolded polypetides. Thus, any protein chaperone that binds exposed hydrophobic moieties and prevents aggregation of a protein of interest can be used in the methods described herein.

The exogenous protein chaperone can also be an enzyme that catalyzes covalent changes important for the formation of native and functional conformations of the protein of interest. For example, in some embodiments, the exogenous protein chaperone is a protein disulfide isomerase (PDI) or a peptidyl-prolyl cis-trans isomerase (PPI). Examples of PDI's include, but are not limited to, a mammalian PDI, a yeast PDI, or a bacterial PDI. In some embodiments, the PDI is a member of the Dsb (disulfide bond formation) family of *E. coli*, for example, DsbA or DsbC. In one embodiment, the exogenous protein chaperone is thioredoxin (Trx). Examples of PPI's include, but are not limited to, cyclophilins (whose isomerase activity is inhibited by cyclosporin A); FKBPs (FK506 binding proteins), which are inhibited by FK506 and rapamycin; and parvulins. The three families of PPIases in *E. coli* exhibit limited sequence and structural similarity but share a high catalytic activity and a relatively low affinity for nonstructured peptides. As will be understood by those of skill in the art, the PDI and PPI chaperones can have a modular structure that includes both a chaperone (protein binding) and catalytic domains. See, e.g., Kolag, O., et al., *Microbial Cell Factories*, 2009, 8:9; Wang, C-C., *Methods in Enzymology*, 2002, 348:66-75. Other protein chaperones useful in the methods and systems described herein are referred to as deaggregases, including, for example, Skp.

In another aspect, the disclosure also provides method and systems for expressing properly folded, biologically active proteins in a bacterial cell free synthesis system using a bacterial extract comprising a PDI and a PPIase. The method comprises preparing a bacterial extract comprising components necessary for cell free protein synthesis, such as biologically functioning tRNA, amino acids, ribosomes. The bacterial extract further includes a protein disulfide isomerase and a peptidyl-prolyl cis-trans isomerase, wherein the protein disulfide isomerase and the peptidyl-prolyl cis-trans isomerase are present at a concentration sufficient to improve (e.g., increase) the expression of properly folded biologically active proteins. In this embodiment, the expression of a protein disulfide isomerase and a peptidyl-prolyl cis-trans isomerase provides a synergistic improvement in the expression of properly folded biologically active proteins of interest. For example, the expression of the protein of interest is improved to a concentration above that concentration where one but not both of the protein disulfide isomerase and the peptidyl-prolyl cis-trans isomerase are present, and wherein the incubation conditions are otherwise the same. In embodiments where the expression of a protein disulfide isomerase and a peptidyl-prolyl cis-trans isomerase provides a synergistic improvement in protein expression, the total concentration of the protein disulfide isomerase and the peptidyl-prolyl cis-trans isomerase is at least about 1 gm/liter (g/L) of extract. For example, in some embodiments, the total concentration of the protein disulfide isomerase and the peptidyl-prolyl cis-trans isomerase is at least about 1 g/L, 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L or more of extract. In some embodiments, the total concentration of the protein disulfide isomerase and the peptidyl-prolyl cis-trans isomerase is between about 1 g/L and 20 g/L, between about 1 g/L and 15 g/L, between about 1 g/L and 14 g/L, between about 1 g/L and 10 g/L, or between about 1 g/L and 5 g/L of extract. In some embodiments, the PDI is selected from the group consisting of a Dsb family protein, such as DsbA, DsbC, and DsbG, and the PPI is selected from the group consisting of FkpA, SlyD, tig, SurA, and Cpr6.

The bacterial extracts described herein can be prepared from a bacteria that was co-transformed with genes encoding disulfide isomerases and prolyl isomerases. The bacteria (e.g., E. coli) from which the extract is prepared can express the exogenous protein chaperone from a gene operably linked to a constitutive promoter. In some embodiments, the exogenous protein chaperone is DsbA, DsbC, FkpA, SlyD, and/or Skp, or a combination thereof. In some embodiments, the bacterial extract is an S30 extract from E. coli.

The bacterial cell free synthesis systems described herein can have a volume between about 20 microliters and 500 liters, and the incubation time is a time period lasting from about 1 hour to about 36 hours. For example, the incubation time can be between about 1 to 36 hours, about 1 to 24 hours, about 1 to 18 hours, or about 1 to 12 hours.

In order to produce the protein of interest, the bacterial extract is combined with a nucleic acid that encodes the protein of interest to yield a bacterial cell free synthesis system. The nucleic acid that encodes the protein of interest is typically a DNA or an mRNA. Methods for expressing the protein of interest from a nucleic acid are described in more detail below. The bacterial cell free synthesis system is incubated under conditions that permit the expression and/or proper folding of the protein of interest. In some embodiments, the protein of interest is expressed at a concentration of at least about 100 mg/L, 200 mg/L, 300 mg/L, 400 mg/L, 500 mg/L, 600 mg/L, 700 mg/L, 800 mg/L, 900 mg/L, or 1000 mg or more per L. Conditions for the expression of the protein of interest are described in more detail below.

In some embodiments, the protein of interest has at least one disulfide bond in its biologically active conformation. In one embodiment, the protein of interest has at least two proline residues. The protein of interest can also be an antibody or antibody fragment. In some embodiments, the protein of interest is expressed as a fusion protein with a chaperon protein described herein.

In another aspect, the disclosure provides a method for improving the vitality and/or growth rate of an E. coli cell culture. The method comprises transforming an E coli cell with a Dsb protein operably linked to a constitutive promoter; and culturing the transformed E coli cell under conditions that permit the overexpression of the Dsb protein. In some embodiments, the Dsb protein is expressed at an intracellular concentration of at least about 1 mg/ml. For example, in some embodiments, the Dsb protein is expressed at an intracellular concentration of about 1 mg/ml to about 40 mg/ml.

In some embodiments, the protein chaperone can include a poly-amino acid tag, for example a polyhistidine (e.g., $His_6$; SEQ ID NO:24) tag or a poly(Ser-Arg) tag, at the N-terminus or C-terminus. In some embodiments, the poly-amino acid tag comprises charged amino acids. In some embodiments, the charged amino acids are positively charged. In some embodiments, the charged amino acids are negatively charged. In some embodiments, the poly-amino acid tag comprises polar amino acids. In some embodiments, the poly-amino acid tag comprises alternating charged and polar amino acids. In some embodiments, the poly-amino acid tag comprises Ser-Arg-Ser-Arg-Ser-Arg-Ser-Arg (SEQ ID NO:25). In some embodiments, the poly-amino acid tag comprises Ser-Lys-Ser-Lys-Ser-Lys-Ser-Lys (SEQ ID NO:26). In some embodiments, the poly-amino acid tag comprises Asp-Asp-Asp-Asp-Asp-Asp (SEQ ID NO:27). In some embodiments, the poly-amino acid tag comprises Glu-Glu-Glu-Glu-Glu-Glu (SEQ ID NO:28). While not being bound by any particular theory or mechanism of action, it is believed that the C-terminal tag increases the solubility of the chaperone, which results in an increase in the amount of the chaperone in extracts prepared from bacteria that express the tagged chaperone. In some embodiments, the presence of a poly-amino acid tag resulted in an increase in the total amount of protein of interest produced. In some embodiments, centrifuging the activated extract containing a poly-amino acid tagged chaperone increases the amount of properly assembled protein of interest.

General Methods

Unless defined otherwise, all technical and scientific terms used herein have the meaning commonly understood by one of ordinary skill in the art to which this invention belongs. Practitioners are particularly directed to Green, M. R. and Sambrook, J., eds., *Molecular Cloning: A Laboratory Manual*, 4th ed., Cold Spring Harbor Laboratory Press, Cold Spring Harbor, N.Y. (2012), and Ausubel, F. M., et al. *Current Protocols in Molecular Biology* (Supplement 99), John Wiley & Sons, New York (2012), which are incorporated herein by reference, for definitions and terms of the art. Standard methods also appear in Bindereif, Schón, & Westhof (2005) *Handbook of RNA Biochemistry*, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al. (Id.); Berger and Kimmel, *Guide to Molecular Cloning Techniques, Methods in Enzymology* (Volume 152 Academic Press, Inc., San Diego, Calif. 1987); and *PCR Protocols: A Guide to Methods and Applications* (Academic Press, San Diego, Calif. 1990), which are incorporated by reference herein.

Methods for protein purification, chromatography, electrophoresis, centrifugation, and crystallization are described in Coligan et al. (2000) *Current Protocols in Protein Science*, Vol. 1, John Wiley and Sons, Inc., New York. Methods for cell-free synthesis are described in Spirin & Swartz (2008) *Cell-free Protein Synthesis*, Wiley-VCH, Weinheim, Germany. Methods for incorporation of non-native amino acids into proteins using cell-free synthesis are described in Shimizu et al. (2006) *FEBS Journal*, 273, 4133-4140.

PCR amplification methods are well known in the art and are described, for example, in Innis et al. *PCR Protocols: A Guide to Methods and Applications*, Academic Press Inc.

San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al. *Short Protocols in Molecular Biology*, 5$^{th}$ Edition, Wiley, 2002, and Innis et al. *PCR Protocols*, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al. *Proc. Natl. Acad. Sci. U.S.A.* 87:1663-1667, 1990; Eberwine et al. *Proc. Natl. Acad. Sci. U.S.A.* 89:3010-3014, 1992).

When the proteins described herein are referred to by name, it is understood that this includes proteins with similar functions and similar amino acid sequences. Thus, the proteins described herein include the wild-type prototype protein, as well as homologs, polymorphic variations and recombinantly created muteins. For example, the name "DsbC protein" includes the wild-type prototype protein from *E. coli* (e.g., SEQ ID NO:1), as well as homologs from other species, polymorphic variations and recombinantly created muteins. Proteins such as DsbC and FkpA are defined as having similar functions if they have substantially the same biological activity or functional capacity as the wild type protein (e.g., at least 80% of either). Proteins such as DsbC and FkpA are defined as having similar amino acid sequences if they have at least 80%, 85%, 90%, 95%, 96%, 97%, 98%, or 99% sequence identity to the prototype protein. The sequence identity of a protein is determined using the BLASTP program with the defaults wordlength of 3, an expectation (E) of 10, and the BLOSUM62 scoring matrix (see Henikoff and Henikoff, *Proc. Natl. Acad. Sci. USA* 89:10915-10919, 1992).

A readily conventional test to determine if a protein homolog, polymorphic variant or recombinant mutein is inclusive of a protein chaperone described herein is by specific binding to polyclonal antibodies generated against the prototype protein. For example, a DsbC protein includes proteins that bind to polyclonal antibodies generated against the prototype protein of SEQ ID NO:1, and an FkpA protein includes proteins that bind to polyclonal antibodies generated against the prototype protein of SEQ ID NO:6.

With regard to the reaction of a protein chaperone described herein to polyclonal antibodies, the test protein will bind under designated immunoassay conditions to the specified antibodies at least two times the background, and the specified antibodies do not substantially bind in a significant amount to other proteins present in the sample. For example, polyclonal antibodies raised to DsbC, encoded in SEQ ID NO:1, splice variants, or portions thereof, can be selected to obtain only those polyclonal antibodies that are specifically immunoreactive with DsbC and not with other proteins, except for polymorphic variants of DsbC. This selection may be achieved by subtracting out antibodies that cross-react with other members of the Dsb family. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically, a specific or selective reaction will be at least twice background signal or noise and more typically more than 10 to 100 times background.

It will be understood that at least some of the chaperone proteins described herein are members of large families of related proteins with similar functions and various degrees of sequence homology. Thus, the protein chaperones described herein include homologs of family members having similar function, for example, homologs of PDI and PPIases, homologs of Dsb proteins, homologs of FkpA proteins, etc. Thus, in some embodiments, the chaperones can have at least about 60%, 65%, 70%, 75%, 80%, 85%, 90%, 95%, 96%, 97%, 98%, or 99% sequence identity to the chaperones described herein. Further, the data provided in the Examples show that eukaryotic PDI and bacterial DsbC are functionally interchangeable regarding their ability to produce properly assembled IgG, which provides evidence that homologs of the chaperones described herein can be used in the methods and systems described herein.

1. Cell Free Protein Synthesis (CFPS) Technology

In order to express the biologically active proteins of interest described herein, a cell free protein synthesis system can be used. Cell extracts have been developed that support the synthesis of proteins in vitro from purified mRNA transcripts or from mRNA transcribed from DNA during the in vitro synthesis reaction.

CFPS of polypeptides in a reaction mix comprises bacterial extracts and/or defined reagents. The reaction mix comprises at least ATP or an energy source; a template for production of the macromolecule, e.g., DNA, mRNA, etc.; amino acids, and such co-factors, enzymes and other reagents that are necessary for polypeptide synthesis, e.g., ribosomes, tRNA, polymerases, transcriptional factors, aminoacyl synthetases, elongation factors, initiation factors, etc. In one embodiment of the invention, the energy source is a homeostatic energy source. Also included may be enzyme(s) that catalyze the regeneration of ATP from high-energy phosphate bonds, e.g., acetate kinase, creatine kinase, etc. Such enzymes may be present in the extracts used for translation, or may be added to the reaction mix. Such synthetic reaction systems are well-known in the art, and have been described in the literature.

The term "reaction mix" as used herein, refers to a reaction mixture capable of catalyzing the synthesis of polypeptides from a nucleic acid template. The reaction mixture comprises extracts from bacterial cells, e.g, *E. coli* S30 extracts. S30 extracts are well known in the art, and are described in, e.g., Lesley, S. A., et al. (1991), *J. Biol. Chem.* 266, 2632-8. The synthesis can be performed under either aerobic or anaerobic conditions.

In some embodiments, the bacterial extract is dried. The dried bacterial extract can be reconstituted in milli-Q water (e.g., reverse osmosis water) at 110% of the original solids as determined by measuring the percent solids of the starting material. In one embodiment, an accurately weighed aliquot of dried extract, representing 110% of the original solids of 10 mL of extract, is added to 10 mL of Milli-Q water in a glass beaker with a stir bar on a magnetic stirrer. The resulting mixture is stirred until the powder is dissolved. Once dissolved, the material is transferred to a 15 mL Falcon tube and stored at −80 C unless used immediately.

The volume percent of extract in the reaction mix will vary, where the extract is usually at least about 10% of the total volume; more usually at least about 20%; and in some instances may provide for additional benefit when provided at at least about 50%; or at least about 60%; and usually not more than about 75% of the total volume.

The general system includes a nucleic acid template that encodes a protein of interest. The nucleic acid template is an RNA molecule (e.g., mRNA) or a nucleic acid that encodes an mRNA (e.g., RNA, DNA) and be in any form (e.g., linear, circular, supercoiled, single stranded, double stranded, etc.). Nucleic acid templates guide production of the desired protein.

To maintain the template, cells that are used to produce the extract can be selected for reduction, substantial reduction or elimination of activities of detrimental enzymes or for enzymes with modified activity. Bacterial cells with modified nuclease or phosphatase activity (e.g., with at least one mutated phosphatase or nuclease gene or combinations thereof) can be used for synthesis of cell extracts to increase synthesis efficiency. For example, an *E. coli* strain used to make an S30 extract for CFPS can be RNase E or RNase A deficient (for example, by mutation).

CFPS systems can also be engineered to guide the incorporation of detectably labeled amino acids, or unconventional or unnatural amino acids, into a desired protein. The amino acids can be synthetic or derived from another biological source. Various kinds of unnatural amino acids, including without limitation detectably labeled amino acids, can be added to CFPS reactions and efficiently incorporated into proteins for specific purposes. See, for example, Albayrak, C. and Swartz, J R., *Biochem. Biophys Res. Commun.*, 431(2):291-5; Yang W C et al. *Biotechnol. Prog.* (2012), 28(2):413-20; Kuechenreuther et al. *PLoS One*, (2012), 7(9):e45850; and Swartz J R., *AIChE Journal*, 58(1):5-13.

In a generic CFPS reaction, a gene encoding a protein of interest is expressed in a transcription buffer, resulting in mRNA that is translated into the protein of interest in a CFPS extract and a translation buffer. The transcription buffer, cell-free extract and translation buffer can be added separately, or two or more of these solutions can be combined before their addition, or added contemporaneously.

To synthesize a protein of interest in vitro, a CFPS extract at some point comprises a mRNA molecule that encodes the protein of interest. In some CFPS systems, mRNA is added exogenously after being purified from natural sources or prepared synthetically in vitro from cloned DNA using RNA polymerases such as RNA polymerase II, SP6 RNA polymerase, T3 RNA polymerase, T7 RNA polymerase, RNA polymerase III and/or phage derived RNA polymerases. In other systems, the mRNA is produced in vitro from a template DNA; both transcription and translation occur in this type of CFPS reaction. In some embodiments, the transcription and translation systems are coupled or comprise complementary transcription and translation systems, which carry out the synthesis of both RNA and protein in the same reaction. In such in vitro transcription and translation systems, the CFPS extracts contain all the components (exogenous or endogenous) necessary both for transcription (to produce mRNA) and for translation (to synthesize protein) in a single system. The coupled transcription and translation systems described herein are sometimes referred to as Open-Cell Free Synthesis (OCFS) systems, and are capable of achieving high titers of properly folded proteins of interest, e.g., high titers of antibody expression.

A cell free protein synthesis reaction mixture comprises the following components: a template nucleic acid, such as DNA, that comprises a gene of interest operably linked to at least one promoter and, optionally, one or more other regulatory sequences (e.g., a cloning or expression vector containing the gene of interest) or a PCR fragment; an RNA polymerase that recognizes the promoter(s) to which the gene of interest is operably linked (e.g. T7 RNA polymerase) and, optionally, one or more transcription factors directed to an optional regulatory sequence to which the template nucleic acid is operably linked; ribonucleotide triphosphates (rNTPs); optionally, other transcription factors and co-factors therefor; ribosomes; transfer RNA (tRNA); other or optional translation factors (e.g., translation initiation, elongation and termination factors) and co-factors therefore; one or more energy sources, (e.g., ATP, GTP); optionally, one or more energy regenerating components (e.g., PEP/pyruvate kinase, AP/acetate kinase or creatine phosphate/creatine kinase); optionally factors that enhance yield and/or efficiency (e.g., nucleases, nuclease inhibitors, protein stabilizers, chaperones) and co-factors therefore; and; optionally, solubilizing agents. The reaction mix further comprises amino acids and other materials specifically required for protein synthesis, including salts (e.g., potassium, magnesium, ammonium, and manganese salts of acetic acid, glutamic acid, or sulfuric acids), polymeric compounds (e.g., polyethylene glycol, dextran, diethyl aminoethyl dextran, quaternary aminoethyl and aminoethyl dextran, etc.), cyclic AMP, inhibitors of protein or nucleic acid degrading enzymes, inhibitors or regulators of protein synthesis, oxidation/reduction adjuster (e.g., DTT, ascorbic acid, glutathione, and/or their oxides), non-denaturing surfactants (e.g., Triton X-100), buffer components, spermine, spermidine, putrescine, etc. Components of CFPS reactions are discussed in more detail in U.S. Pat. Nos. 7,338,789 and 7,351,563, and U.S. App. Pub. Nos. 2010/0184135 and US 2010/0093024, the disclosures of each of which is incorporated by reference in its entirety for all purposes.

Depending on the specific enzymes present in the extract, for example, one or more of the many known nuclease, polymerase or phosphatase inhibitors can be selected and advantageously used to improve synthesis efficiency.

Protein and nucleic acid synthesis typically requires an energy source. Energy is required for initiation of transcription to produce mRNA (e.g., when a DNA template is used and for initiation of translation high energy phosphate for example in the form of GTP is used). Each subsequent step of one codon by the ribosome (three nucleotides; one amino acid) requires hydrolysis of an additional GTP to GDP. ATP is also typically required. For an amino acid to be polymerized during protein synthesis, it must first be activated. Significant quantities of energy from high energy phosphate bonds are thus required for protein and/or nucleic acid synthesis to proceed.

An energy source is a chemical substrate that can be enzymatically processed to provide energy to achieve desired chemical reactions. Energy sources that allow release of energy for synthesis by cleavage of high-energy phosphate bonds such as those found in nucleoside triphosphates, e.g., ATP, are commonly used. Any source convertible to high energy phosphate bonds is especially suitable. ATP, GTP, and other triphosphates can normally be considered as equivalent energy sources for supporting protein synthesis.

To provide energy for the synthesis reaction, the system can include added energy sources, such as glucose, pyruvate, phosphoenolpyruvate (PEP), carbamoyl phosphate, acetyl phosphate, creatine phosphate, phosphopyruvate, glyceraldehyde-3-phosphate, 3-Phosphoglycerate and glucose-6-phosphate, that can generate or regenerate high-energy triphosphate compounds such as ATP, GTP, other NTPs, etc.

When sufficient energy is not initially present in the synthesis system, an additional source of energy is preferably supplemented. Energy sources can also be added or supplemented during the in vitro synthesis reaction.

In some embodiments, the cell-free protein synthesis reaction is performed using the PANOx-SP system comprising NTPs, E. coli tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, phosphoenol pyruvate (PEP), NAD, CoA, $Na^+$ oxalate, putrescine, spermidine, and S30 extract.

In some embodiments, proteins containing a non-natural amino acid (nnAA) may be synthesized. In such embodiments, the reaction mix may comprise the non-natural amino acid, a tRNA orthogonal to the 20 naturally occurring amino acids, and a tRNA synthetase that can link the nnAA with the orthogonal tRNA. See, e.g., US Pat. App. Pub. No. US 2010/0093024. Alternately, the reaction mix may comprise a nnAA conjugated to a tRNA for which the naturally occurring tRNA synthetase has been depleted. See, e.g., PCT Pub. No. WO2010/081111.

In some instances, the cell-free synthesis reaction does not require the addition of commonly secondary energy sources, yet uses co-activation of oxidative phosphorylation and protein synthesis. In some instances, CFPS is performed in a reaction such as the Cytomim (cytoplasm mimic) system. The Cytomim system is defined as a reaction condition performed in the absence of polyethylene glycol with optimized magnesium concentration. This system does not accumulate phosphate, which is known to inhibit protein synthesis.

The presence of an active oxidative phosphorylation pathway can be tested using inhibitors that specifically inhibit the steps in the pathway, such as electron transport chain inhibitors. Examples of inhibitors of the oxidative phosphorylation pathway include toxins such as cyanide, carbon monoxide, azide, carbonyl cyanide m-chlorophenyl hydrazone (CCCP), and 2,4-dinitrophenol, antibiotics such as oligomycin, pesticides such as rotenone, and competitive inhibitors of succinate dehydrogenase such as malonate and oxaloacetate.

In some embodiments, the cell-free protein synthesis reaction is performed using the Cytomim system comprising NTPs, E. coli tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, sodium pyruvate, NAD, CoA, $Na^+$ oxalate, putrescine, spermidine, and S30 extract. In some embodiments, the energy surbstrate for the Cytomim system is pyruvate, glutamic acid, and/or glucose. In some embodiments of the system, the nucleoside triphosphates (NTPs) are replaced with nucleoside monophosphates (NMPs).

The cell extract can be treated with iodoacetamide in order to inactivate enzymes that can reduce disulfide bonds and impair proper protein folding. As further described herein, the cell extract can also be treated with a prokaryotic disulfide bond isomerase, such as, not limited to, E. coli DsbC and PDI. The cell extract can be treated with DsbC, FkpA and peptidyl peolyl isomerase. Glutathione disulfide (GSSG) and glutathione (GSH) can also be added to the extract at a ratio that promotes proper protein folding and prevents the formation of aberrant protein disulfides.

In some embodiments, the CFPS reaction includes inverted membrane vesicles to perform oxidative phosphorylation. These vesicles can be formed during the high pressure homogenization step of the preparation of cell extract process, as described herein, and remain in the extract used in the reaction mix.

The cell-free extract can be thawed to room temperature before use in the CFPS reaction. The extract can be incubated with 50 μM iodoacetamide for 30 minutes when synthesizing protein with disulfide bonds. In some embodiments, the CFPS reaction includes about 30% (v/v) iodoacetamide-treated extract with about 8 mM magnesium glutamate, about 10 mM ammonium glutamate, about 130 mM potassium glutamate, about 35 mM sodium pyruvate, about 1.2 mM AMP, about 0.86 mM each of GMP, UMP, and CMP, about 2 mM amino acids (about 1 mM for tyrosine), about 4 mM sodium oxalate, about 0.5 mM putrescine, about 1.5 mM spermidine, about 16.7 mM potassium phosphate, about 100 mM T7 RNA polymerase, about 2-10 μg/mL plasmid DNA template, about 1-10 μM E. coli DsbC, and a total concentration of about 2 mM oxidized (GSSG) glutathione. Optionally, the cell free extract can include 1 mM of reduced (GSH).

The cell free synthesis reaction conditions may be performed as batch, continuous flow, or semi-continuous flow, as known in the art. The reaction conditions are linearly scalable, for example, the 0.3 L scale in a 0.5 L stirred tank reactor, to the 4 L scale in a 10 L fermentor, and to the 100 L scale in a 200 L fermentor.

The development of a continuous flow in vitro protein synthesis system by Spirin et al. (1988) Science 242:1162-1164 proved that the reaction could be extended up to several hours. Since then, numerous groups have reproduced and improved this system (see, e.g., Kigawa et al. (1991) J. Biochem. 110:166-168; Endo et al. (1992) J. Biotechnol. 25:221-230). Kim and Choi (Biotechnol. Prog. 12: 645-649, 1996) have reported that the merits of batch and continuous flow systems can be combined by adopting a "semicontinuous operation" using a simple dialysis membrane reactor. They were able to reproduce the extended reaction period of the continuous flow system while maintaining the initial rate of a conventional batch system. However, both the continuous and semi-continuous approaches require quantities of expensive reagents, which must be increased by a significantly greater factor than the increase in product yield.

Several improvements have been made in the conventional batch system (Kim et al. (1996) Eur. J. Biochem. 239: 881-886; Kuldlicki et al. (1992) Anal. Biochem. 206:389-393; Kawarasaki et al. (1995) Anal. Biochem. 226: 320-324). Although the semicontinuous system maintains the initial rate of protein synthesis over extended periods, the conventional batch system still offers several advantages, e.g. convenience of operation, easy scale-up, lower reagent costs and excellent reproducibility. Also, the batch system can be readily conducted in multiplexed formats to express various genetic materials simultaneously. Patnaik and Swartz (Biotechniques 24:862-868, 1998) have reported that the initial specific rate of protein synthesis could be enhanced to a level similar to that of in vivo expression through extensive optimization of reaction conditions. It is notable that they achieved such a high rate of protein synthesis using the conventional cell extract prepared without any condensation steps (Nakano et al. (1996) J. Biotechnol. 46:275-282; Kim et al. (1996) Eur. J. Biochem. 239:881-886). Kigawa et al. (1999) FEBS Lett 442:15-19 report high levels of protein synthesis using condensed extracts and creatine phosphate as an energy source. These results imply that further improvement of the batch system, especially in terms of the longevity of the protein synthesis reaction, would substantially increase the productivity for batch in vitro protein synthesis. However, the reason for the early halt of protein synthesis in the conventional batch system has remained unclear.

The protein synthesis reactions described herein can utilize a large scale reactor, small scale, or may be multiplexed to perform a plurality of simultaneous syntheses. Continuous reactions can use a feed mechanism to introduce a flow of reagents, and may isolate the end-product as part of the process. Batch systems are also of interest, where additional reagents may be introduced to prolong the period of time for active synthesis. A reactor can be run in any mode such as batch, extended batch, semi-batch, semi-continuous, fed-batch and continuous, and which will be selected in accordance with the application purpose.

2. Generating a Lysate

The methods and systems described herein use a cell lysate for in vitro translation of a target protein of interest. For convenience, the organism used as a source for the lysate may be referred to as the source organism or host cell. Host cells may be bacteria, yeast, mammalian or plant cells, or any other type of cell capable of protein synthesis. A lysate comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2, and IF-3, elongation factors such as EF-Tu, EF-Ts, and EF-G, release factors such as RF-1, RF-2, and RF-3, and the like.

An embodiment uses a bacterial cell from which a lysate is derived. A bacterial lysate derived from any strain of bacteria can be used in the methods of the invention. The bacterial lysate can be obtained as follows. The bacteria of choice are grown to log phase in any of a number of growth media and under growth conditions that are well known in the art and easily optimized by a practitioner for growth of the particular bacteria. For example, a natural environment for synthesis utilizes cell lysates derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as E. coli, using both defined and undefined sources of nutrients. Cells that have been harvested overnight can be lysed by suspending the cell pellet in a suitable cell suspension buffer, and disrupting the suspended cells by sonication, breaking the suspended cells in a French press, continuous flow high pressure homogenization, or any other method known in the art useful for efficient cell lysis The cell lysate is then centrifuged or filtered to remove large DNA fragments and cell debris.

The bacterial strain used to make the cell lysate generally has reduced nuclease and/or phosphatase activity to increase cell free synthesis efficiency. For example, the bacterial strain used to make the cell free extract can have mutations in the genes encoding the nucleases RNase E and RNase A. The strain may also have mutations to stabilize components of the cell synthesis reaction such as deletions in genes such as tnaA, speA, sdaA or gshA, which prevent degradation of the amino acids tryptophan, arginine, serine and cysteine, respectively, in a cell-free synthesis reaction. Additionally, the strain may have mutations to stabilize the protein products of cell-free synthesis such as knockouts in the proteases ompT or lonP.

3. Proteins of Interest

The methods and systems described herein are useful for increasing the expression of properly folded, biologically active proteins of interest. The protein of interest can be any protein that is capable of being expressed in a bacterial cell free synthesis system. Non-limiting examples include proteins with disulfide bonds and proteins with at least two proline residues. The protein of interest can be, for example, an antibody or fragment thereof, therapeutic proteins, growth factors, receptors, cytokines, enzymes, ligands, etc. Additional examples of proteins of interest are described below.

A. Proteins with Disulfide Bonds

The methods provided herein can be used for any protein having at least one disulfide bond in its biologically active confirmation. Disulfide bonds can stabilize tertiary protein structure by locking folding units into stable conformations by linking residues in a covalent manner.

In prokaryotic cells, disulfide bonds are formed when DsbA protein donates its disulfide bond to a newly synthesized polypeptide that comprises a disulfide bond in its native structure. The integral membrane protein DsbB generates disulfide bonds within itself, which are then transferred to DsbA. In some eukaryotic cells, the major disulfide pathway is composed of the membrane-associated flavoprotein Ero1 and the soluble thioredoxin-like protein PDI. Ero1, using a flavin cofactor to mediate the reoxidation of its cysteine pair by oxygen, generates disulfide bonds within itself, and then transfers the bonds to PDI. In turn, PDI transfers the disulfide bonds directly to newly synthesized polypeptides that have not adopted their native structure.

Disulfide bonds are present in numerous proteins including, but not limited to secreted proteins, immune proteins, extracellular matrix proteins, glycoproteins, lysosomal proteins and membrane proteins. Detailed descriptions of disulfide bonds and proteins with disulfide bonds can be found in, e.g., Fass, D. *Annu. Rev. Biophys.*, 2012, 41:63-79, Sevier, C. S. and Kaiser, C. A. *Antioxidants & Redox Signaling*, 2006, 8(5):797-811 and de Marco, A., *Microbial Cell Factories*, 2009, 8:26.

B. Proteins with Prolines

The methods provided herein can be used for any protein that has at least two proline residues. Proline containing proteins typically favor secondary structure elements such as turns and polyproline helices. A polyproline helix can be an elongated, left-handed helix with torsion angles $\varphi=-78°$ and $\psi=+146°$ of the peptide backbone. A relatively high proportion of prolines can be found in proteins near the center of transmembrane helices. Proline residues can also be found in β-turns and α-helical capping motifs, e.g., at the end of an α-helix or even one or two residues from the end. Prolines can also undergo cis-trans isomerization which is important for proper protein folding.

Proline-rich proteins include proteins with repetitive short proline-rich sequences, with tandemly repeated proline-rich sequences, with non-repetitive proline-rich regions, and with hydroxyproline-rich proteins. Prolines residues can be found in various proteins including, but not limited to integral membrane proteins such as transporters, channels, and receptors, globular proteins, hormones, neuropeptides, mucins, immunoglobulins, and extracellular matrix proteins.

It has been shown that proline-rich peptides can enhance and/or sustain nitric oxide production in cells, potentiate argininosuccinate synthetase activity in cells, increase intracellular concentration of calcium ions, and serve as ligands for SH3, WW, EVH1 or BHB domain containing proteins. Detailed descriptions of proline-containing proteins can be found in, e.g., Williamson, M. *Biochem. J.* 1994, 297:249-260 and Kay et al. *FASEB J.*, 14:231-241.

4. Chaperones

To improve the expression of a biologically active protein of interest, the present methods and systems use a bacterial extract comprising an exogenous protein chaperone. Molecular chaperones are proteins that assist the non-covalent folding or unfolding and the assembly or disassembly of other macromolecular structures. One major function of chaperones is to prevent both newly synthesized polypeptide chains and assembled subunits from aggregating into non-functional structures. The first protein chaperone identified, nucleoplasmin, assists in nucleosome assembly from DNA and properly folded histones. Such assembly chaperones aid in the assembly of folded subunits into oligomeric structures. Chaperones are concerned with initial protein folding as they are extruded from ribosomes, intracellular trafficking of proteins, as well as protein degradation of misfolded or denatured proteins. Although most newly synthesized proteins can fold in absence of chaperones, a minority strictly requires them. Typically, inner portions of the chaperone are hydrophobic whereas surface structures are hydrophilic. The exact mechanism by which chaperones facilitate folding of substrate proteins is unknown, but it is thought that by lowering the activation barrier between the partially folded structure and the native form, chaperones accelerate the desired folding steps to ensure proper folding. Further, specific chaperones unfold misfolded or aggregated proteins and rescue the proteins by sequential unfolding and refolding back to native and biologically active forms.

A subset of chaperones that encapsulate their folding substrates are known as chaperonins (e.g., Group I chaperonin GroEL/GroES complex). Group II chaperonins, for example, the TRiC (TCP-1 Ring Complex, also called CCT for chaperonin containing TCP-1) are thought to fold cytoskeletal proteins actin and tubulin, among other substrates. Chaperonins are characterized by a stacked double-ring structure and are found in prokaryotes, in the cytosol of eukaryotes, and in mitochondria.

Other types of chaperones are involved in membrane transport in mitochondria and endoplasmic reticulum (ER) in eukaryotes. Bacterial translocation-specific chaperone maintains newly synthesized precursor polypeptide chains in a translocation-competent (generally unfolded) state and guides them to the translocon, commonly known as a translocator or translocation channel. A similar complex of proteins in prokaryotes and eukaryotes most commonly refers to the complex that transports nascent polypeptides with a targeting signal sequence into the interior (cisternal or lumenal) space of the endoplasmic reticulum (ER) from the cytosol, but is also used to integrate nascent proteins into the membrane itself (membrane proteins). In the endoplasmic reticulum (ER) there are general chaperones (BiP, GRP94, GRP170), lectin (calnexin and calreticulin) and non-classical molecular chaperones (HSP47 and ERp29) helping to fold proteins. Folding chaperone proteins include protein disulfide isomerases (PDI, DsbA, DsbC) and peptidyl prolyl cis-trans isomerases (PPI, FkpA, SlyD, TF).

Many chaperones are also classified as heat shock proteins (Hsp) because they are highly upregulated during cellular stress such as heat shock, and the tendency to aggregate increases as proteins are denatured by elevated temperatures or other cellular stresses. Ubiquitin, which marks proteins for degradation, also has features of a heat shock protein. Some highly specific 'steric chaperones' convey unique structural conformation (steric) information onto proteins, which cannot be folded spontaneously. Other functions for chaperones include assistance in protein degradation, bacterial adhesin activity, and response to prion diseases linked to protein aggregation.

Enzymes known as foldases catalyze covalent changes essential for the formation of the native and functional conformations of synthesized proteins. Examples of foldases include protein disulfide isomerase (PDI), which acts to catalyze the formation of native disulfide bonds, and peptidyl prolyl cis-trans isomerase (PPI), which acts to catalyze isomerization of stable trans peptidyl prolyl bonds to the cis configuration necessary for the functional fold of proteins. The formation of native disulfides and the cis-trans isomerization of prolyl imide bonds are both covalent reactions and are frequently rate-limiting steps in the protein folding process. Recently proposed to be chaperone proteins, in stoichiometric concentrations foldases increase the reactivation yield of some denatured proteins. Other examples of chaperone proteins include deaggregases such as Skp, and the redox proteins Trr1 and Glr1.

In some embodiments, the protein chaperone can be co-expressed with another protein(s) that functions to increase the activity of the desired protein chaperone. For example, the Dsb proteins DsbA and DsbC can be coexpressed with DsbB and DsbD, which oxidize and reduce DsbA and DsbC, respectively.

5. Transforming Bacteria with Genes Encoding the Chaperones

The bacterial extracts used in the methods and systems described herein contain an exogenous protein chaperone. The exogenous protein chaperones described herein can be added to the extract, or can be expressed by the bacteria used to prepare the cell free extract. In the latter embodiment, the exogenous protein chaperone can be expressed from a gene encoding the exogenous protein chaperone that is operably linked to a promoter that initiates transcription of the gene.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lac, T3, T7, lambda Pr'P1' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

In some embodiments, the promoter is a constitutive promoter. Examples of constitutive promoters in bacteria include the spc ribosomal protein operon promoter $P_{spc}$, the β-lactamase gene promotor $P_{bla}$ of plasmid pBR322, the $P_L$ promoter of phage λ, the replication control promoters $P_{RNAI}$ and $P_{RNAII}$ of plasmid pBR322, the P1 and P2 promoters of the rrnB ribosomal RNA operon, the tet promoter, and the pACYC promoter.

6. Quantitatively Measuring Protein of Interest and Chaperones

The quantity of the protein of interest produced by the methods and systems described herein can be determined using any method known in the art. For example, the expressed protein of interest can be purified and quantified using gel electrophoresis (e.g., PAGE), Western analysis or capillary electrophoresis (e.g., Caliper LabChip). Protein synthesis in cell-free translation reactions may be monitored by the incorporation of radiolabeled amino acids, typically, $^{35}$S-labeled methionine or $^{14}$C-labeled leucine. Radiolabeled proteins can be visualized for molecular size and quantitated by autoradiography after electrophoresis or isolated by immunoprecipitation. The incorporation of recombinant His tags affords another means of purification by $Ni^{2+}$ affinity column chromatography. Protein production from expression systems can be measured as soluble protein yield or by using an assay of enzymatic or binding activity.

The amount of chaperone protein that is added to the cell free synthesis system can be quantified by including a radioactive amino acid, such as $^{14}$C-Leucine, in the bacterial cell culture used to prepare the bacterial extract, and quantifying the amount of expressed protein chaperone by, for example, precipitating the radioactive protein using trichloroacetic acid (TCA), and measuring the total amount of radioactivity recovered. The amount of chaperone can also be measured immunologically, for example, by an ELISA in which monoclonal or polyclonal antibodies against the chaperone are used to detect and quantify chaperone protein immobilized in plates or on a Western blot.

7. Quantitatively Measuring Biological Activity and Proper Folding of Expressed Proteins The biological activity of a protein of interest produced by the methods described herein can be quantified using an in vitro or in vivo assay specific for the protein of interest. The biological activity of the protein of interest can be expressed as the biological activity per unit volume of the cell-free protein synthesis reaction mixture. The proper folding of an expressed protein of interest can be quantified by comparing the amount of total protein produced to the amount of soluble protein. For example, the total amount of protein and the soluble fraction of that protein produced can be determined by radioactively labeling the protein of interest with a radiolabeled amino acid such as $^{14}$C-leucine, and precipitating the labeled proteins with TCA. The amount of folded and assembled protein can be determined by gel electrophoresis (PAGE) under reducing and non-reducing conditions to measure the fraction of soluble proteins that are migrating at the correct molecular weight. Under non-reducing conditions, protein aggregates can be trapped above the gel matrix or can migrate as higher molecular weight smears that are difficult to characterize as discrete entities, whereas under reducing conditions and upon heating of the sample, proteins containing disulfide bonds are denatured, aggregates are dissociated, and expressed proteins migrate as single bands. Methods for determining the amount of properly folded and assembled antibody proteins are described in the Examples. Functional activity of antibody molecules can be determined using an immunoassay, for example, an ELISA.

EXAMPLES

Example 1

This example demonstrates that chaperone proteins expressed by a bacterial cell free protein synthesis system increase the amount of properly assembled IgG expressed by the cell free protein synthesis system, and that the combination of a bacterial PDI and a PPI acted synergistically to increase the amount of properly assembled IgG.

Engineering of a bacterial endoplasmic reticulum for the rapid expression of immunoglobulin proteins.

Materials and Methods:

Small-scale cell-free expression. 100 μl cell-free protein synthesis reactions were run at 30° C. for 12 hr in a 96-well microtiter plate at 650 rpm in a VWR Thermomixer in the presence of 10 μg/mL DNA (2.5 μg/mL trastuzumab light chain DNA, 7.5 μg/mL trastuzumab heavy chain DNA in the expression vector pYD317). Cell-free extracts were treated with 50 μM iodoacetamide for 30 min at RT (20° C.) and added to a premix of components. The final concentration in the protein synthesis reaction was 30% cell extract (v/v), 2 mM GSSG, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 1 mM for tyrosine and phenylalanine), 4 mM sodium oxalate, 1 mM putrescine, 1.5 mM spermidine, 15 mM potassium phosphate, 20 ug/mL T7 RNAP, unless otherwise indicated.

Interchangeability of PDI and DsbC. Cell-free protein synthesis reactions were run at varying concentrations of PDI and DsbC to understand the requirements for disulfide bond isomerases on IgG folding and assembly. 0-5 uM recombinant PDI was added to cell-free reactions in combination with 0-13 uM recombinant DsbC. 100 μl cell-free reactions were run with 30% control extract for 12 hr at 30° C. in a 96-well microtiter plate at 650 rpm in a VWR Thermomixer in the presence of 8 μg/mL HC-HIS6 DNA and 2 μg/mL LC DNA. The reactions were subsequently centrifuged at 5000×g for 10 minutes and supernatants were diluted 2-fold with PBS prior to purification on IMAC Phytips (200 μl tips, 5 μl resin bed) using a Biomek robotic system. Samples were eluted in 20 mM Tris pH8, 300 mM NaCl, 500 mM imidazole and the eluted IgG was quantified using capillary electrophoresis on a Caliper LapChip GXII.

Chaperone sequential expression screen. Candidate chaperones were cloned into the cell-free expression plasmid pYD317. From these plasmids, PCR fragments were generated that contained the chaperone gene sandwiched between T7 promoter and terminator sequences. Chaperones were subsequently expressed from these PCR fragments by cell-free protein synthesis under standard microtiter plate conditions for 16 hr at 30° C. To stabilize the PCR fragments against DNA degradation, 40 ug/mL GamS protein was added to the reactions. Chaperone-expressing extract was subsequently centrifuged at 5000×g for 10 minutes and chaperone-containing supernatants were added into new cell-free reactions at 20% (v/v) for the expression of IgG (8 μg/mL trastuzumab heavy chain DNA and 2 μg/mL trastuzumab light chain DNA) in the presence of $^{14}$C-leucine. IgG titers were calculated based on the rate of incorporation of $^{14}$C-leucine into the IgG molecule, as previously described (MAbs. 2012 Mar. 1; 4(2)). Chaperone-related improvements in IgG titer were expressed as a fold improvement over the addition of a GFP-expressing extract. To estimate the amount of chaperone being added to the IgG expression reactions, chaperone cell-free reactions were also run in the presence of $^{14}$C-leucine and the expressed protein was quantified.

2× DsbC and 2× FkpA extracts. Bicistronic plasmids of the bacterial genes DsbC (2× DsbC) and FkpA (2× FkpA) behind a constitutive promoter (pACYC) were generated and transformed into bacteria. These strains were grown to log phase and lysed for the production of cell-free extract, as described in Yang W. C. et al. *Biotechnol. Prog.* (2012), 28(2):413-20. FkpA protein was added to an IgG cell-free reaction using 2× DsbC extract to test if FkpA would further improve IgG folding and assembly. The reverse experiment was performed by the addition of 13 μM DsbC protein to a cell-free reaction with 2× FkpA extract.

Results:

Interchangeability of PDI and DsbC. To better understand the dependence of IgG folding and assembly on eukaryotic and bacterial disulfide bond isomerases, IgG cell-free protein synthesis reactions were run at varying concentrations of PDI and DsbC. IgG was expressed in cell-free reactions in the presence of 0-5 μM PDI in combination with 0-13 μM DsbC. Expressed IgG-His was purified by N$^{++}$ resin and quantified by capillary electrophoresis (FIG. 1). In the absence of DsbC, IgG was highly dependent on PDI for folding (FIG. 1, closed circles). However, as the concentration of DsbC in the reaction increased, the dependence on PDI fell such that at 6.4 μM DsbC, there was no additional benefit attributable to PDI in the reaction (FIG. 1, open triangles). Furthermore, by increasing the concentration of DsbC in the reaction, we saw marked improvements in IgG titers beyond what we had previously observed (FIG. 1, open circles). In effect, we observed the efficient substitution of a eukaryotic disulfide bond isomerase with a bacterial chaperone of a similar function in the folding of a eukaryotic protein.

Chaperone sequential expression screen. In vivo, eukaryotic chaperones are known to play an important role in the folding and assembly of IgG. Therefore, expression of IgG molecules in bacterial systems which lack these physiological foldases has been challenging (REFS). As such, we undertook a screening approach to identify chaperone proteins that would be positive effectors of IgG folding and/or assembly. Candidate chaperones were expressed in our cell-free system and expressed chaperones were subsequently added into new cell-free reactions for the expression of IgG. Any improvements in IgG folding were expressed as an improvement in titer over the addition of a GFP-expressing control extract, a protein unlikely to interact with IgG. In order to improve the throughput of the screen, chaperones were not purified from the extract before being added to IgG reactions. Because of this, we wanted to ensure that chaperone DNA was not being transcribed and expressed in subsequent IgG reactions. As such, chaperone proteins were expressed from PCR template which is significantly more labile than plasmid DNA. The addition of GamS protein helped preserve the PCR template, such that sufficient levels of chaperone protein could be synthesized.

Figure 2A:
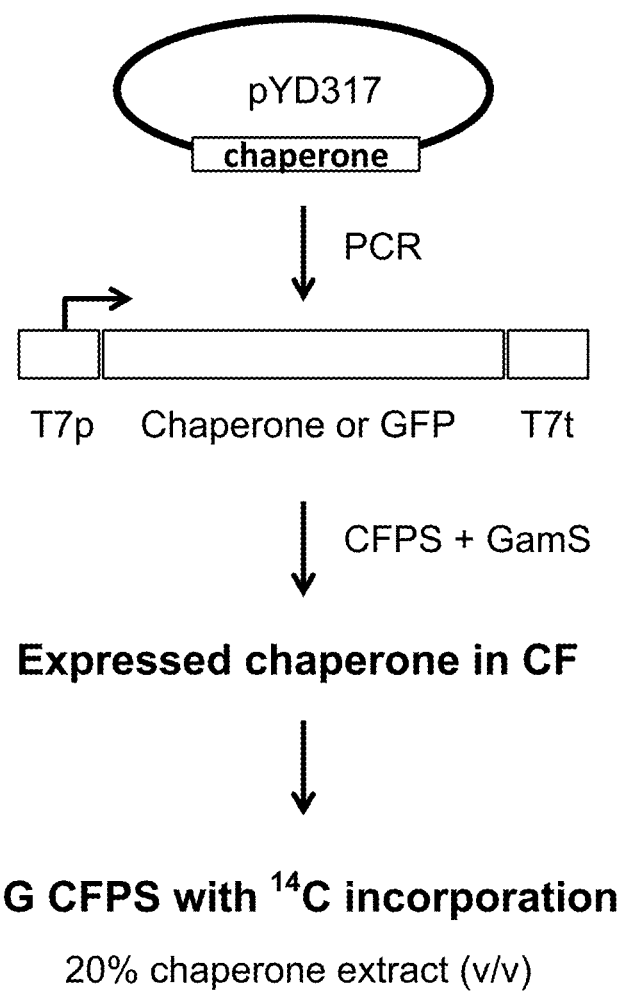
FIG. 2A shows a schematic illustration of the chaperone sequential expression screen described in the Examples.
Figure 2B:
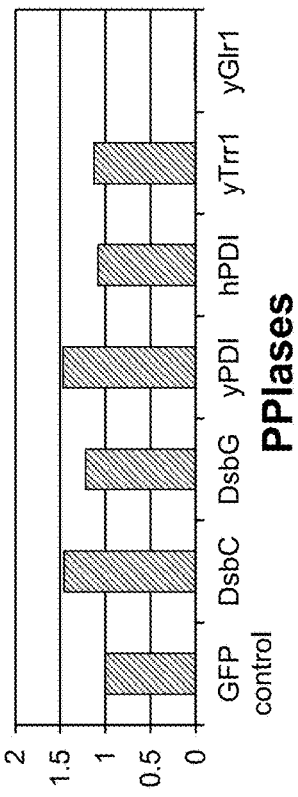
FIG. 2B shows that IgG titer can be improved by adding bacterial cell free system expressed protein chaperones to the bacterial cell free synthesis system.
Figure 2B:
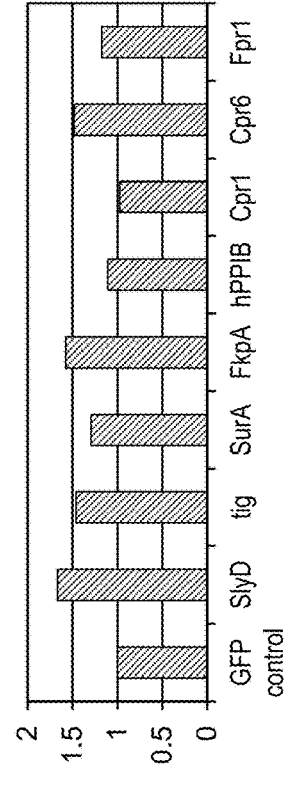
Figure 2B:
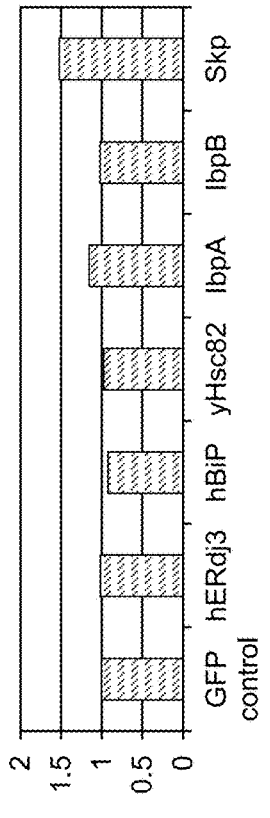

Several families of chaperones were of particular interest given their role in folding IgG in vivo. PPIases, foldases, deaggregases, and redox proteins from bacterial, yeast, and human species were tested. Among the redox chaperones, we found that PDI (yeast homologue) and DsbC significantly aided IgG formation, consistent with our previous findings (FIG. 2B). Interestingly, human PDI (hPDI) did not significantly impact IgG folding, probably due to its poor expression in cell extract which did not allow it to be added in sufficient quantities to aid IgG folding. By contrast, the bacterial protein DsbC expressed very well in the extract, allowing the addition of ~5 uM DsbC to the IgG reaction (DsbC was expressed at ~25 uM and it was added at 20% to an IgG reaction). Among the PPIases tested, several proved to be beneficial to IgG expression (FIG. 2B). From these, we decided to follow-up on Skp, SlyD, and FkpA.

Figure 3:
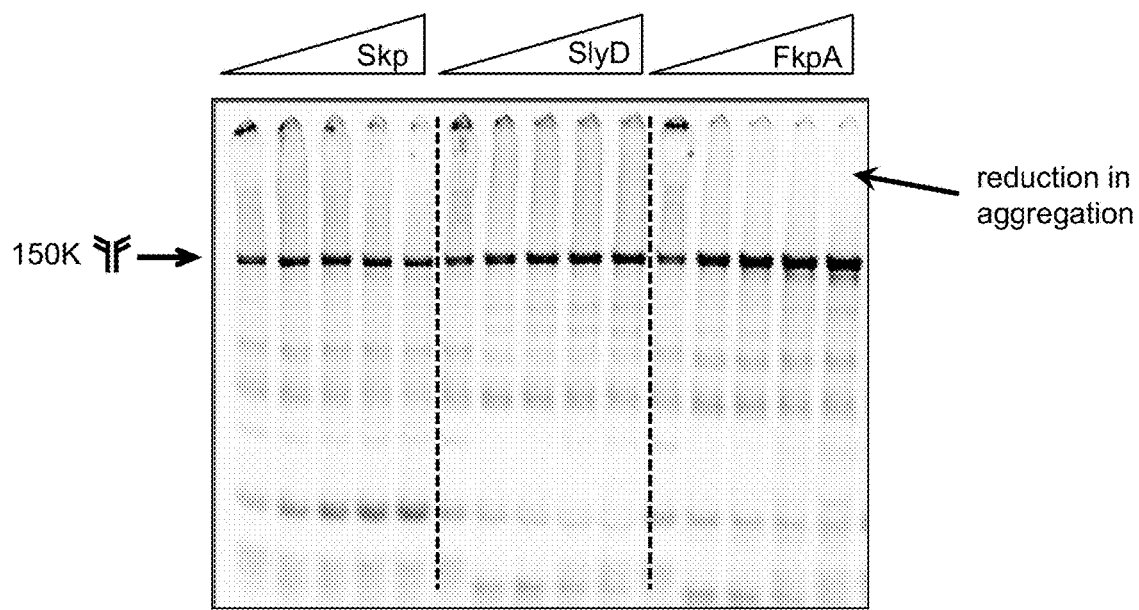
FIG. 3 shows that the protein chaperones Skp, SlyD and FkpA improve the solubility and/or amount of properly assembled IgG.
Figure 3:
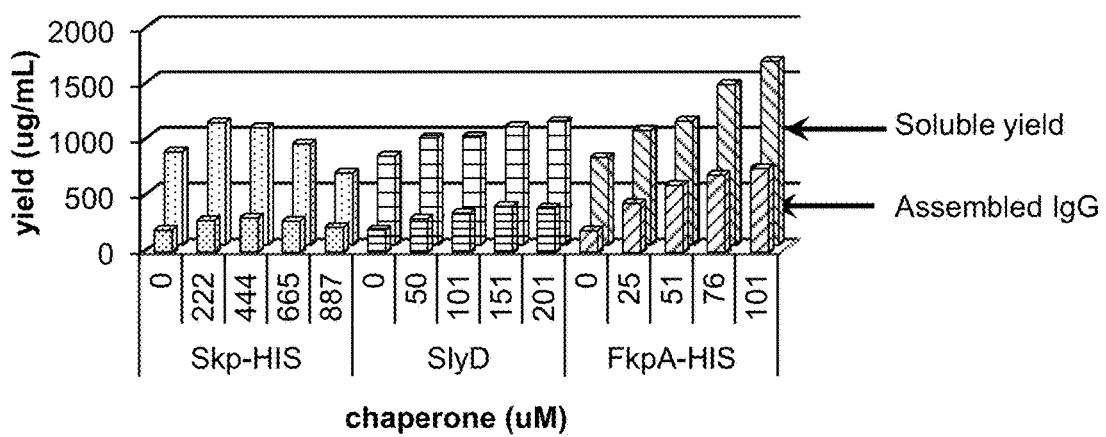

Purified Skp, SlyD, and FkpA can improve IgG titers. To confirm our hits from the chaperone screen, we expressed and purified Skp, SlyD, and FkpA and added them back into IgG cell-free protein synthesis reactions (FIG. 3). For the chaperone Skp, we saw that Skp aided the solubility of HC and LC, but did not increase the amount of assembled IgG significantly. However, for the prolyl isomerases, SlyD and FkpA, we observed that the more of these chaperones we added, the amount of soluble proteins and assembled IgG increased proportionately. We reasoned that prolyl isomerization was a function that was previously limiting for IgG formation in our cell-free protein synthesis system and the addition of these exogenous proteins improved IgG folding and assembly dramatically. Because of the vast improvements observed with DsbC and FkpA, we decided to further characterize their roles in IgG folding.

Figure 4:
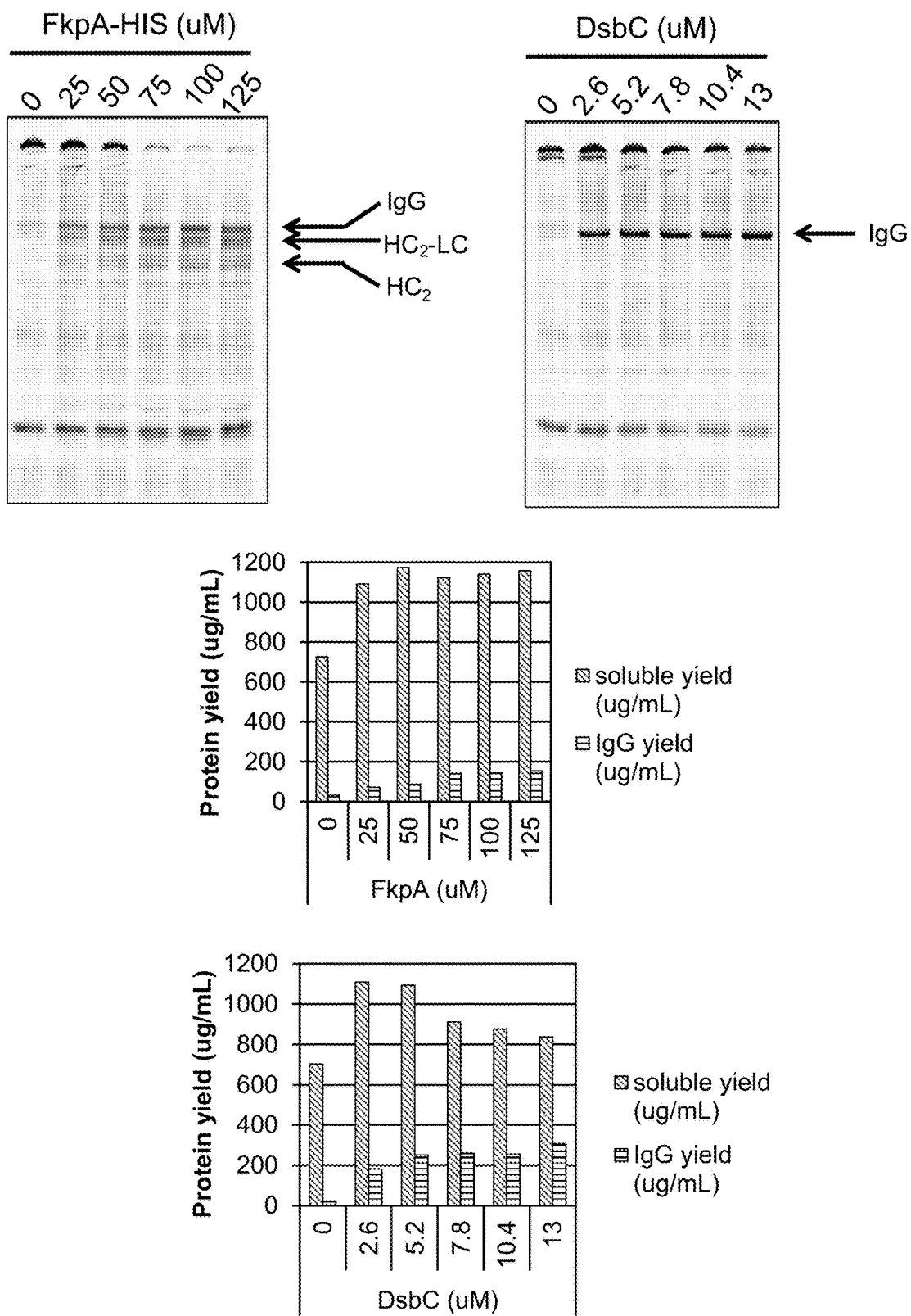
FIG. 4 shows that the protein chaperone FkpA improves the solubility and folding of IgG proteins.

FkpA and DsbC work synergistically to fold and assemble IgG. To better understand the roles that FkpA and DsbC play in IgG formation, we independently evaluated their contributions to IgG folding (FIG. 4). Interestingly, the addition of FkpA significantly reduced the degree of higher molecular weight aggregates formed during HC and LC synthesis. With increasing amounts of FkpA, we also observe the formation of IgG, as well as a number of partially assembled products. These proteins migrated as fuzzy bands, suggesting that they may represent mixed populations of cross-disulfide bonded proteins. The addition of DsbC, on the other hand, generated clear sharp bands of IgG. However, without FkpA, a significant proportion of the expressed proteins formed higher order aggregates that could not completely enter the SDS-PAGE gel.

Figure 5:
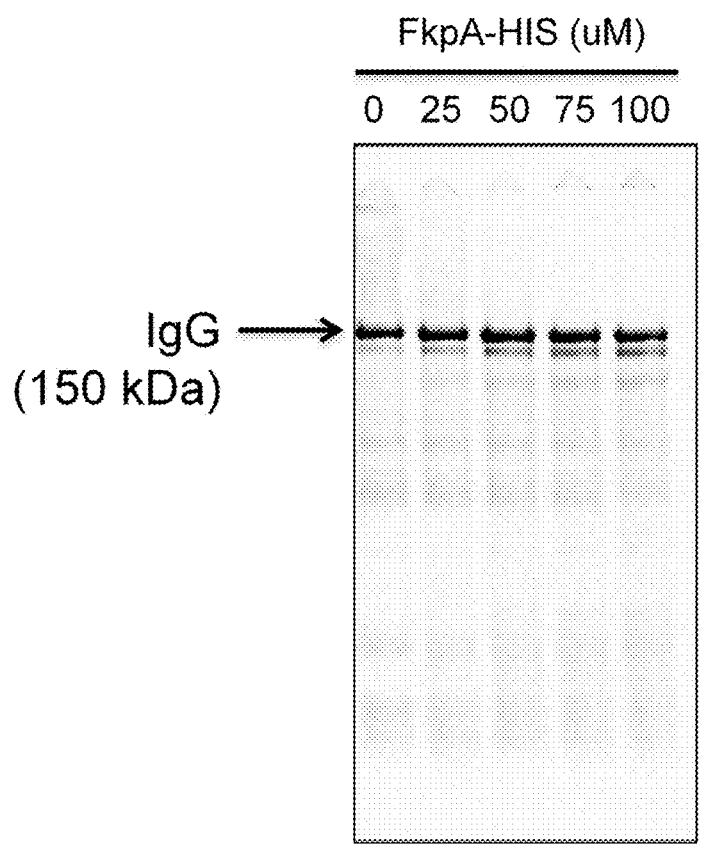
FIG. 5 shows that the addition of purified FkpA to an extract containing DsbC promotes IgG folding.
Figure 5:
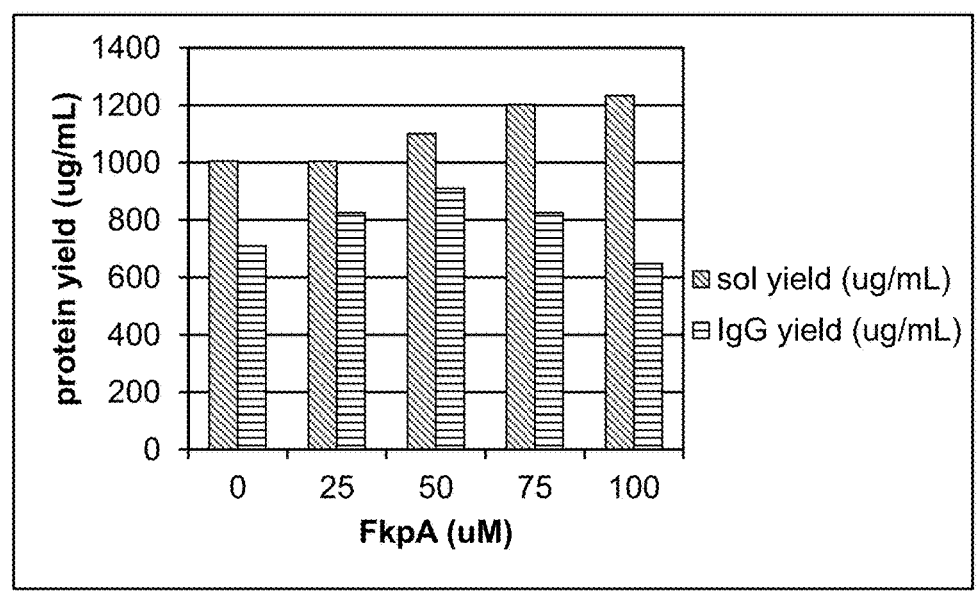
Figure 6:
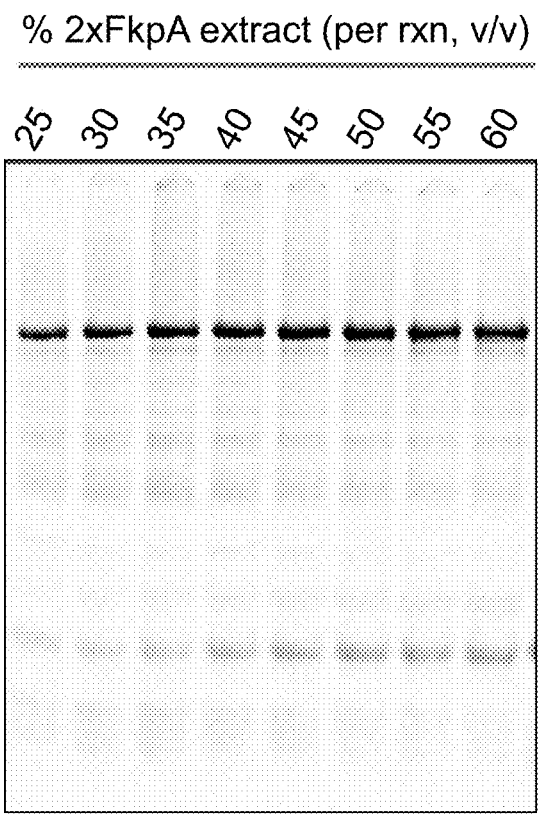
FIG. 6 shows that the addition of exogenous DsbC protein added to an extract containing FkpA increases the IgG titer.
Figure 6:
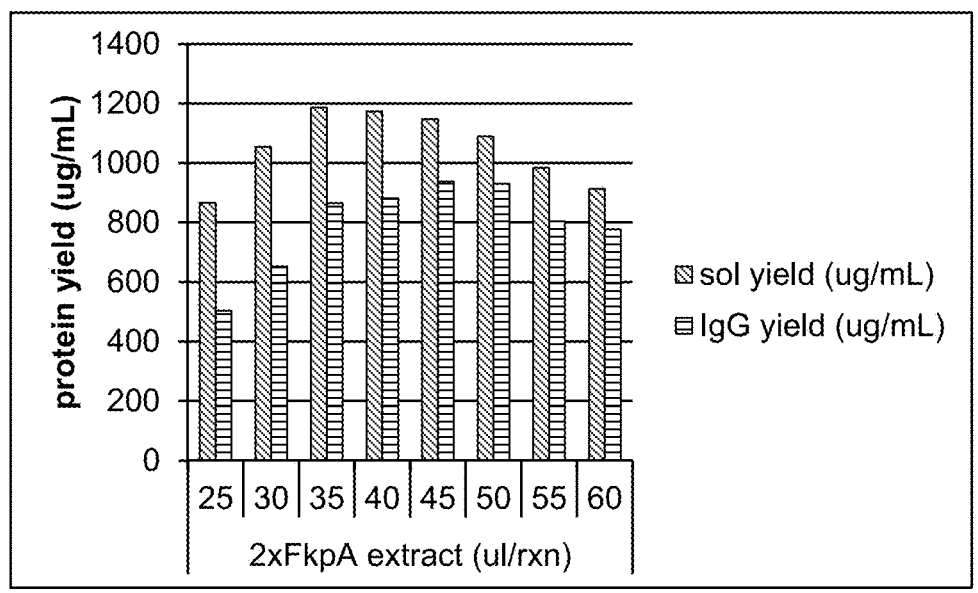

When the two chaperones were combined into the same IgG reaction, they acted synergistically to fold IgG (FIG. 5). HC and LC were expressed in a DsbC-containing extract (2× DsbC) and different amounts of exogenous FkpA protein were added. At 50 uM FkpA, on the order of 900 ug/mL of assembled IgG could be expressed. To follow-up on this, a bacterial strain overexpressing FkpA was engineered from which cell extract was generated. IgG was synthesized from FkpA extract with the addition of exogenous DsbC protein (FIG. 6). IgG was produced at ~600 ug/mL with reduced aggregation under our standard conditions of 30% extract (v/v). To further increase the concentration of FkpA in each reaction, we titrated up the FkpA-containing extract in the reaction which brought the IgG titers to >900 ug/mL (FIG. 6).

The above example demonstrates that the combination of two different classes of protein chaperones, a PDI and a PPI, provides a synergistic effect on proper protein folding and assembly in a cell free expression system.

Example 2

This example demonstrates that overexpression of exogenous protein chaperones in bacterial strains used to prepare cell extracts does not inhibit the production of a protein of interest such as GMCSF.

Strain Descriptions:

SBDG028: SBJY001+pACYC 2× DsbC+ΔRF1
SBDG031: SBJY001+pACYC 2× DsbC
SBDG044: SBJY001+pACYC 2× FkpA
SBDG049: SBJY001+pACYC 2× FkpA-6×His

Cell Extract Preparation:

Extracts from *E. coli* strains SBDG028, SBDG031, SBDG044 and SBDG049 were prepared essentially as described in Zawada et al., *Biotechnology and Bioengineering* Vol. 108, No. 7, July 2011.

GMCSF CFPS Reaction

The cell-free reaction procedure for GMCSF protein production was performed as described in Zawada et al. *Biotechnology and Bioengineering* Vol. 108, No. 7, July 2011, which is incorporated by reference herein in its entirety.

Figure 7:
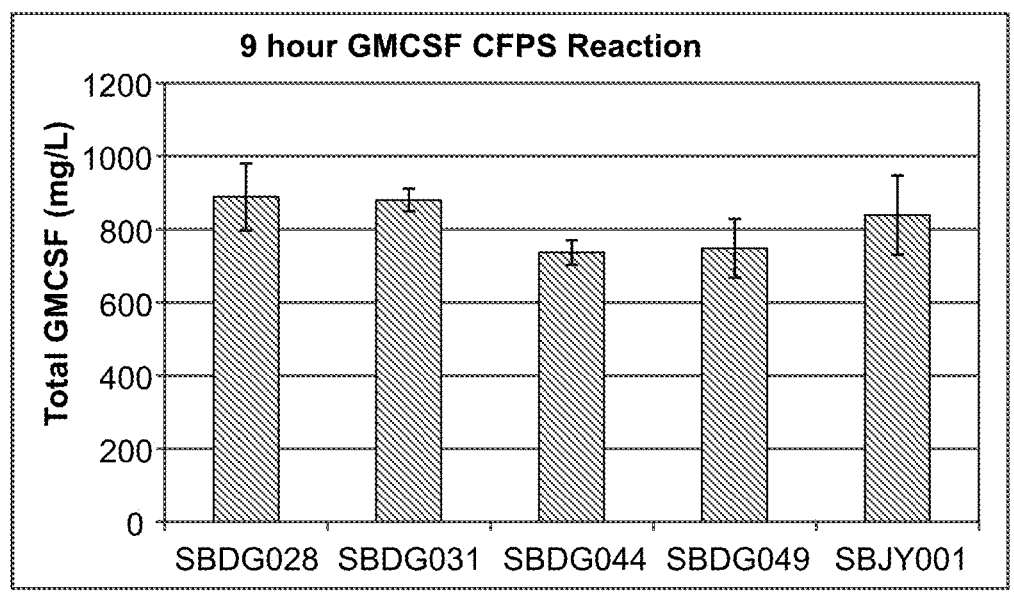
FIG. 7 shows the amount of GMCSF protein produced by the CFPS in extracts from the indicated bacterial strains that express the chaperones DsbC or FkpA.

FIG. 7 shows the amount of GMCSF protein produced by the CFPS in extracts from the indicated strains that overexpress DsbC or FkpA. In control extracts prepared from bacteria that do not express an exogenous DsbC or FkpA, very little GMCSF is produced (data not shown).

Example 3

This example demonstrates that bacterial cells overexpressing protein chaperones have similar growth rates as bacteria that do not overexpress protein chaperones.

Methods: Bacterial strains were transformed with recombinant plasmids that express one (1×) or two (2×) copies DsbC and FkpA, as described in Example 1. These strains were grown to log phase lysed for the production of cell-free extract. The growth rates (doubling times) for the strains were determined, and the amount of protein chaperone produced by the bacteria strains was quantified using Western analysis and/or ELISA.

To determine the intracellular concentration of the expressed protein chaperones, the periplasm of shake flask grown cells was lysed using osmotic shock. The periplasmic lysate was separated by gel electrophoresis with standards of known DsbC concentration. Densitometry was used to compare the intensity of the standard DsbC bands to the intensity of the bands in the periplasmic lysate. The intensity of the bands was used to determine the DsbC concentration in the lysate, which was used to back calculate the concentration of DsbC in the cells.

The amount of chaperone protein in the cell-free extracts was determined by ELISA. The ELISA to determine DsbC and FkpA titers in cell-free extract is the Direct ELISA format. The assay consists of coating an assay plate with standards and samples, then allowing an antibody that recognizes DsbC or FkpA to bind, washing away excess DsbC and FkpA antibody, introducing an HRP conjugated secondary antibody to rabbit IgG (the DsbC and FkpA antibodies were produced in rabbit), washing away excess conjugated secondary antibody, and then using an ABTS substrate to detect the HRP present on the conjugated secondary antibody. Purified DsbC and FkpA with known concentrations were used to create a 7 point standard curve to use in the determination of sample concentrations.

DsbC: MSD (Minimum Sample Dilution): 1/120,000; LLOQ (Lower Limit of Quantitation) at MSD: 187.5 ug/ml.

Figure 8:
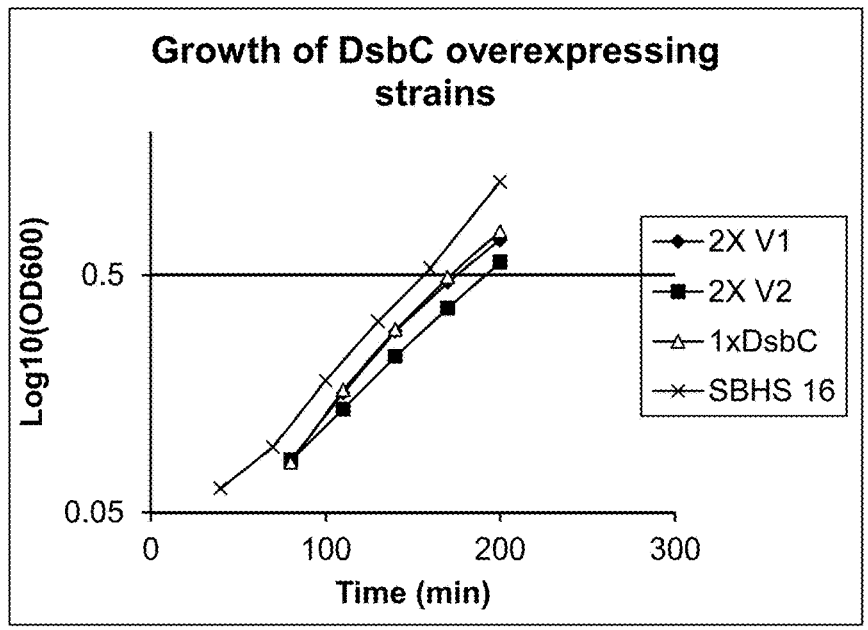
FIG. 8 shows the growth rate of bacterial strains transformed with plasmids that express 1× or 2× copies of DsbC under the control of a constitutive promoter (upper panel). The lower panel shows the amount of DsbC protein present in the periplasmic lysate.
Figure 8:
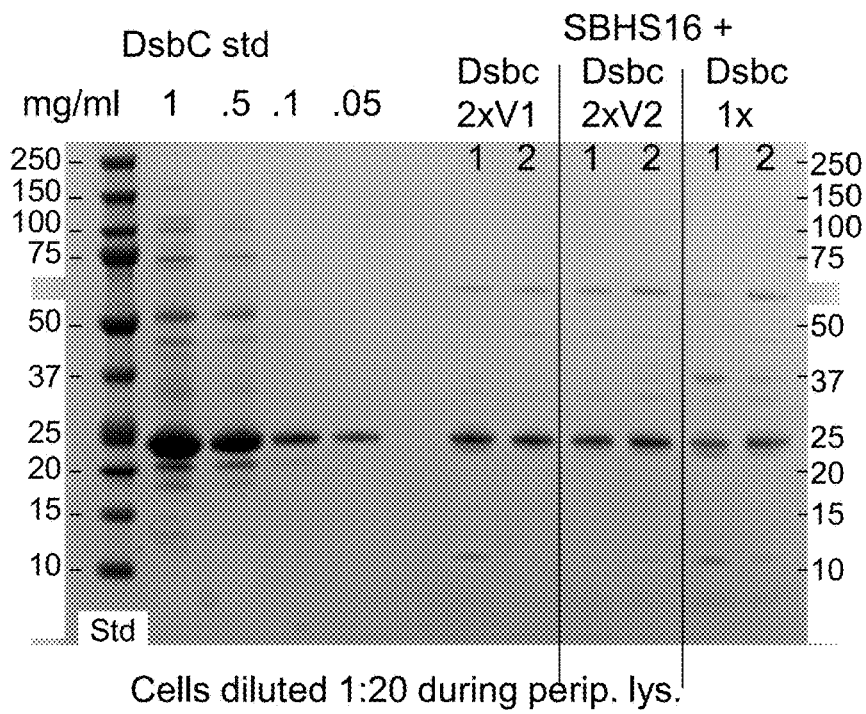

FkpA: MSD (Minimum Sample Dilution): 1/75,000; LLOQ (Lower Limit of Quantitation) at MSD: 390 ug/ml Results:

FIG. 8 shows the growth rate of bacterial strains transformed with plasmids that express 1× or 2× copies of DsbC under the control of a constitutive promoter. The growth rates of strains expressing 1× and 2× copies of DsbC were similar to a control strain that was not transformed with the expression plasmids. The lower panel of FIG. 8 shows the amount of DsbC protein present in the periplasmic lysate, as described above.

Figure 9:
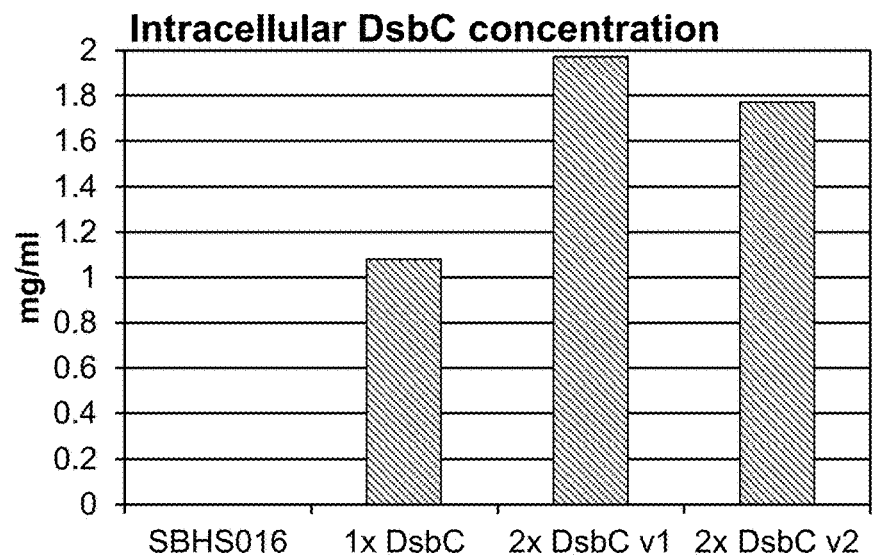
FIG. 9 shows the amount of DsbC protein produced by bacterial strains overexpressing 1× or 2× copies of DsbC. The upper panel shows the intracellular concentration. The lower panel shows the extract concentration.
Figure 9:
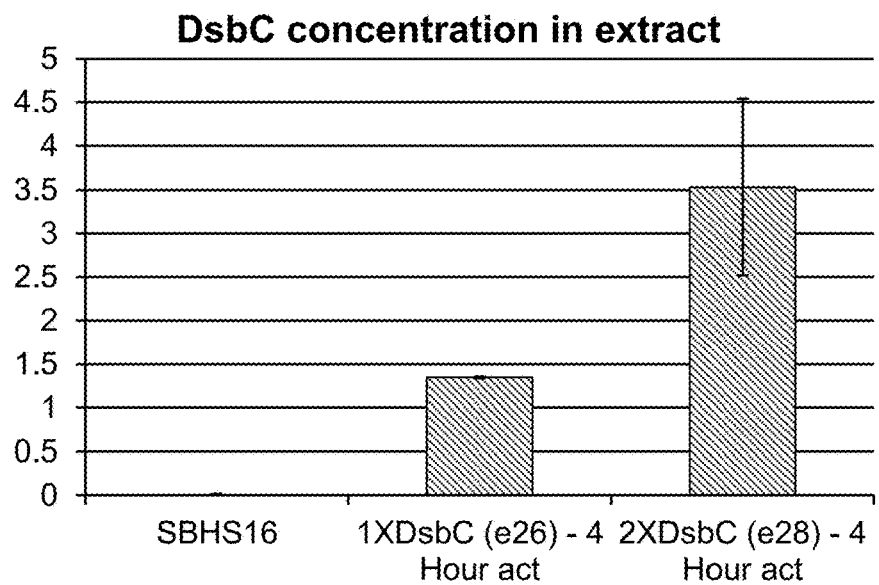

FIG. 9 shows the amount of DsbC protein produced by the bacterial strains overexpressing 1× or 2× copies of DsbC. The upper panel shows the intracellular concentration, determined as described above. The lower panel shows the extract concentration, determined by ELISA.

Figure 10:
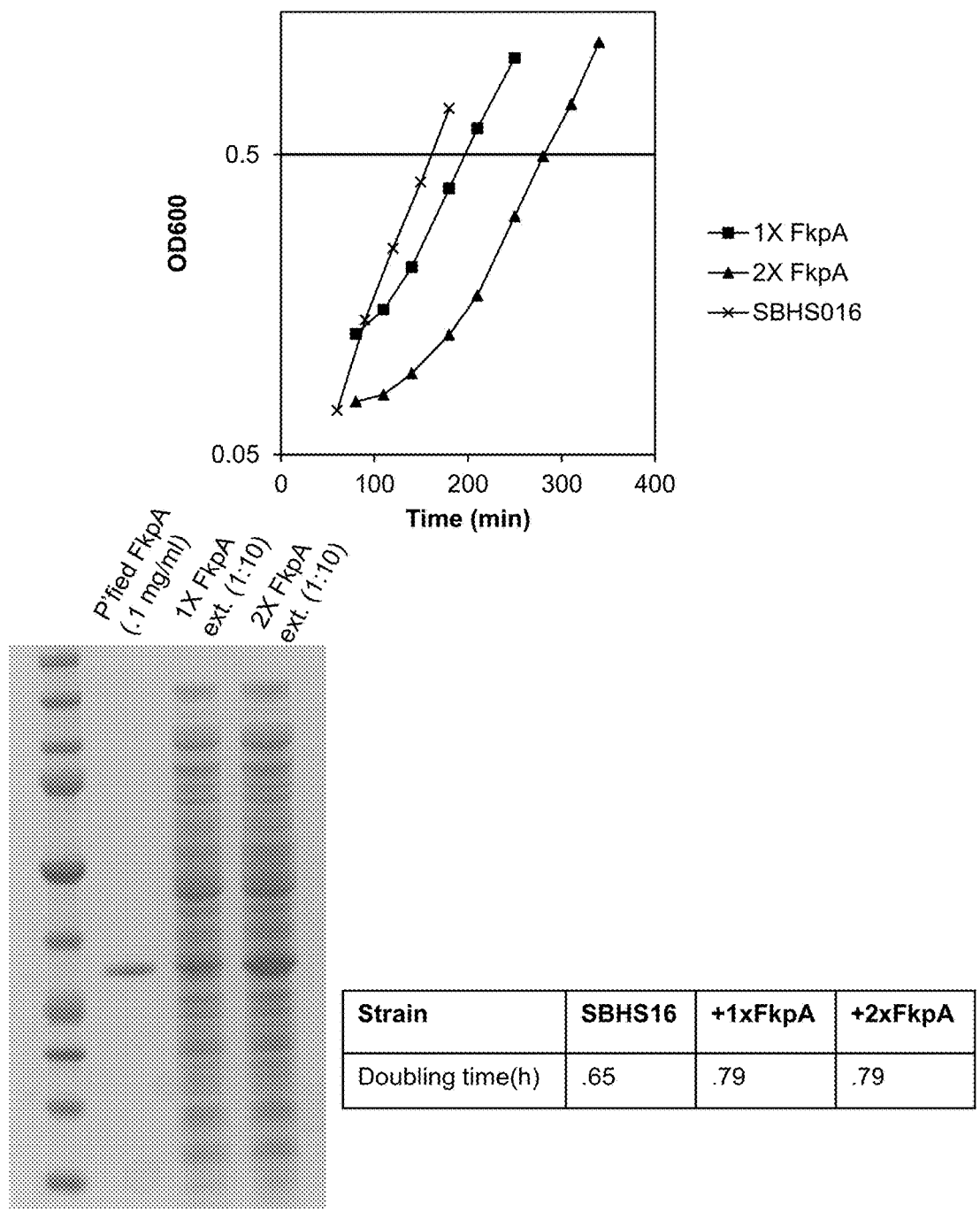
FIG. 10 shows the growth rate of bacterial strains transformed with plasmids that express 1× or 2× copies of FkpA under the control of a constitutive promoter (upper panel). The lower left panel shows the amount of FkpA protein present in total extracts prepared from the bacteria expressing 1× and 2× copies of FkpA. The lower right panel shows the doubling time of the bacterial strains.
Figure 11:
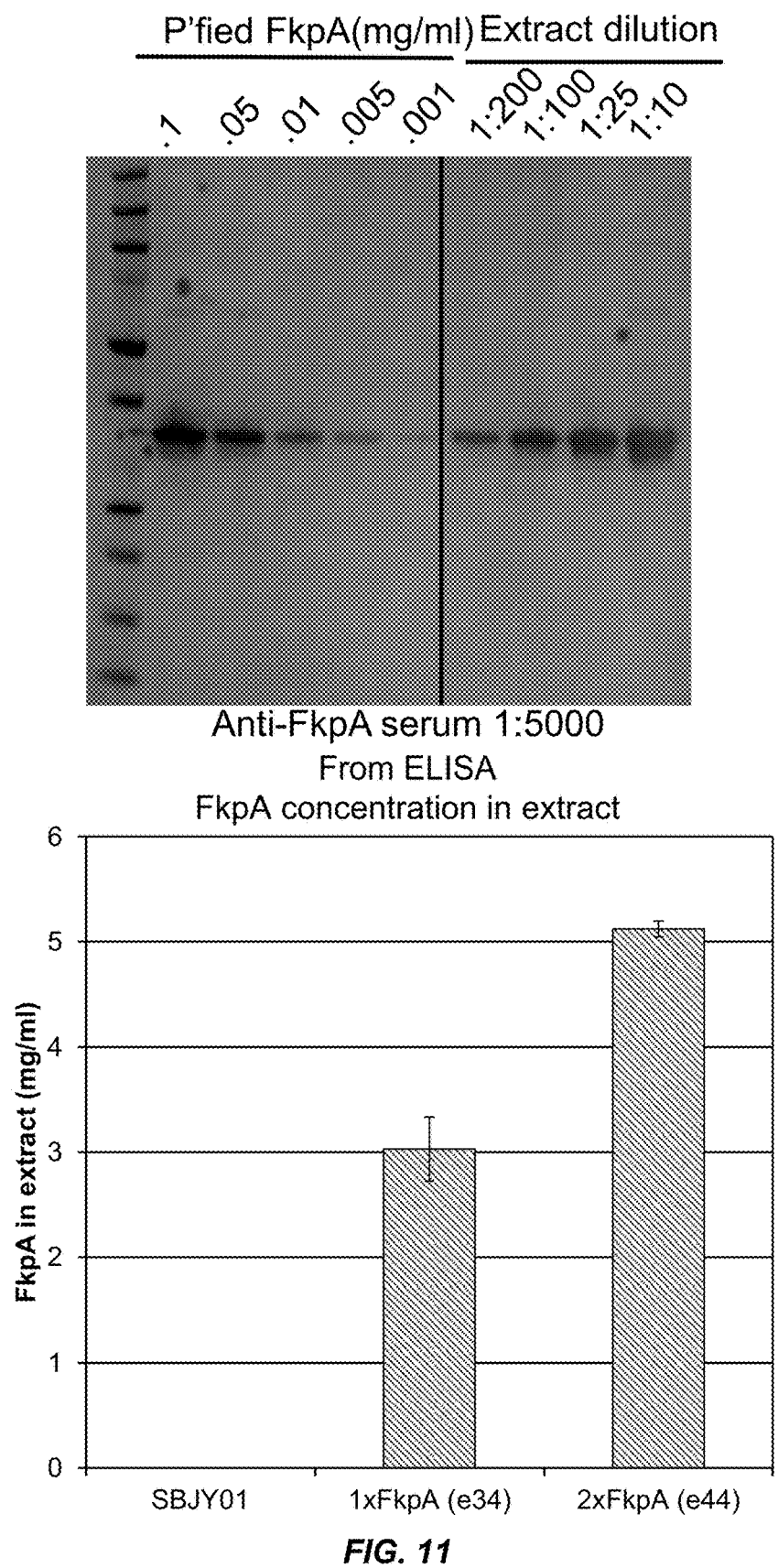
FIG. 11 shows the quantitation of FkpA concentration in extracts from bacteria expressing 1× and 2× copies of FkpA.

FIG. 10 shows growth rate of bacterial strains transformed with plasmids that express 1× or 2× copies of FkpA under the control of a constitutive promoter. The growth rates of strains expressing 1× and 2× copies of FkpA were similar to a control strain that was not transformed with the expression plasmids. The lower left panel of FIG. 10 shows the amount of FkpA protein present in total extracts prepared from the bacteria expressing 1× and 2× copies of FkpA. FIG. 11 shows the quantitation of FkpA concentration in extracts from bacteria expressing 1× and 2× copies of FkpA.

The results of representative ELISA experiments are shown in the Tables below. The ELISA data for FkpA is from a different extract preparation than that shown in FIG. 9, which accounts for the different DsbC concentrations.

TABLE 1

DsbC concentrations determined in extracts by ELISA.

| Strain | Description | DsbC Titer (mg/ml) | Standard Deviation (mg/ml) |
|---|---|---|---|
| SBJY-001 | WT Control Extract | <0.188 | N/A |
| SBDG-026 | 1x DsbC Extract | 1.084 | 0.016 |
| SBDG-028 | 2x DsbC Extract | 3.155 | 0.351 |
| SBDG-031 | 2x DsbC Extract (No RF1 Deletion) | 3.267 | 0.353 |
| SBDG-033 | 3x DsbC Extract | 2.854 | 0.272 |

TABLE 2

FkpA concentrations determined in extracts by ELISA.

| Strain | Description | FkpA Titer (mg/ml) | Standard Deviation (mg/ml) |
|---|---|---|---|
| SBJY-001 | WT Control Extract | <0.390 | N/A |
| SBDG-034 | 1x FkpA | 3.029 | 0.305 |
| SDDG-044 | 2x FkpA | 5.121 | 0.076 |
| SBDG-048 | 2x FkpA with leader sequences removed for cytoplasmic expression | 1.960 | 0.252 |
| SBDG-049 | 2x FkpA w/6xHis (SEQ ID NO: 24) tag | 5.415 | 0.147 |
| SBDG-052 | 1x FkpA Pc7 Promoter | 2.786 | 0.059 |

This example demonstrates that recombinant bacterial strains that overexpress chaperone proteins are capable of rapid growth and are useful for preparing high quality extracts for cell free protein synthesis.

Example 4

This example shows that including a poly-charged amino acid tag on the C-terminal of the chaperone FkpA increased the amount of FkpA in the extract, and increased the amount of total protein produced by the cell free protein synthesis system.

Figure 12:
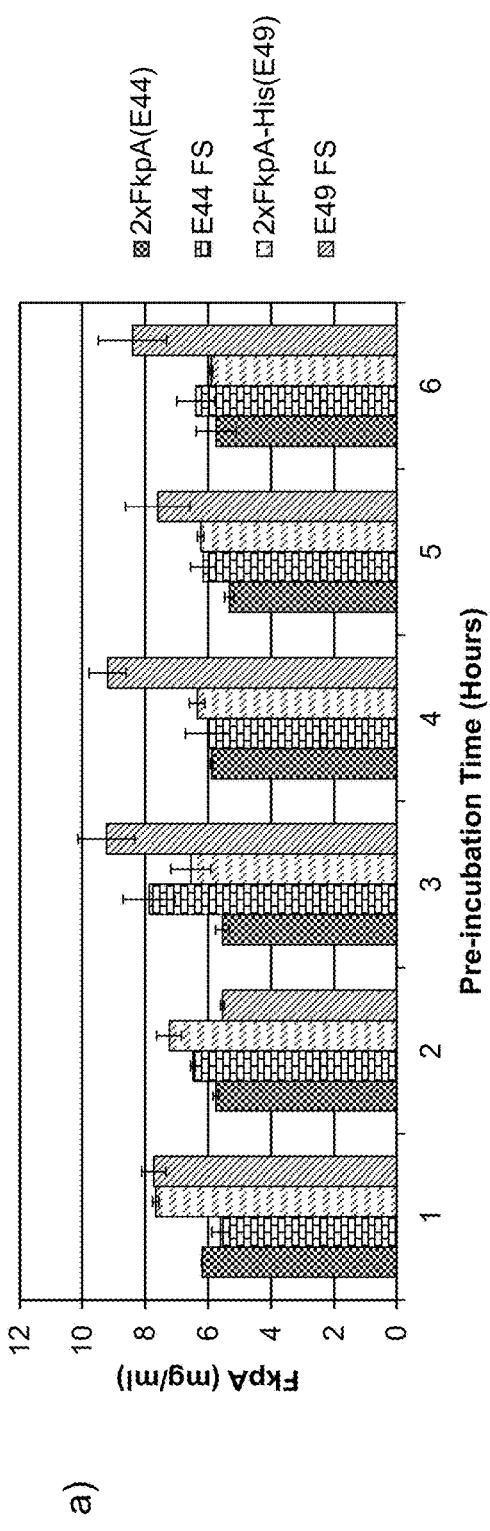
FIG. 12 shows the results of adding a C-terminal His tag to FkpA. (a) shows that extract levels of FkpA prepared from bacteria that overexpress FkpA-His (2× FkpA-His (e49)) were increased by a centrifugal spin after extract activation (pre-incubation) at 30° C. (b) shows that extracts containing FkpA-His produced more total IgG than extracts containing wild-type FkpA (compare 2× FkpA (e44) to 2× FkpA-His (e49)), and that the total amount of correctly assembled IgG was increased by centrifuging the extract after activation (compare 2× FkpA final spin to 2× FkpA-His final spin). Con 1 and Con 2 are control extracts prepared from bacteria that do not express FkpA.
Figure 12:
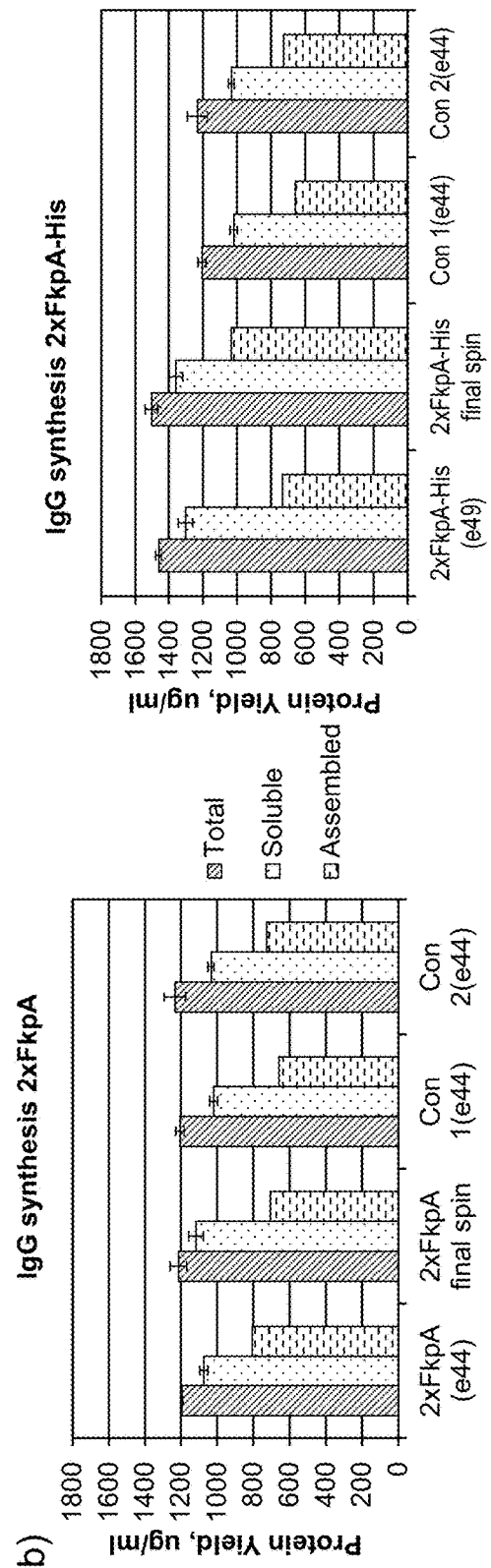

The gene encoding FkpA was cloned with either a $His_6$ (SEQ ID NO:24) or $(Ser-Arg)_4$ (SEQ ID NO:25) tag on the C-terminus in vector pACYC-Pc. These vectors were transformed into strain SBJY001 and extract was produced as described above. An FkpA ELISA showed that extract levels of the His-tagged FkpA variants were increased by a final centrifugal spin of the extract, post-activation (FIG. 12a). Compared to extract containing wt FkpA, extracts containing these solubility-tagged FkpA proteins produced more total protein. In addition, assembled IgG levels were enhanced by a final spin of the extract after activation (FIG. 12b).

This example demonstrates that adding a poly-charged amino acid tag on the C-terminus of FkpA increased the amount of FkpA expressed by bacteria used to make the extract and increased the amount of total protein produced. Further, for extracts containing the C-terminal His-tagged FkpA, spinning the extract down after activation resulted in an increase in the amount of correctly assembled IgG.

Example 5

This example demonstrates that genomic integration of the chaperones dsbC and FkpA in two independent bacterial strains resulted in cells with a high growth rate that produced high chaperone levels, and cell-free extracts derived from these strains contained high levels of both chaperones and supported cell-free synthesis of high levels recombinant IgG and GMC-SF.

Strain 108

Strain SBDG108 is a derivative of SBMT095. This strain has 2 copies of dsbC integrated onto the chromosome into the galK locus behind a medium strength constitutive promoter prepared using homologous recombination. SBMT095 was made competent and then transformed with pACYC-Pc0-2x FkpA, a medium copy plasmid with two copies of FkpA behind a constitutive promoter. Both copies coded for wild type E. coli FkpA, but one gene had been synthesized to reduce nucleotide homology to the WT gene, enabling each to be propagated stably in the same plasmid.

In a standard extract fermentation using DM80-80 in batch mode, strain SBDG108 was capable of achieving a high growth rate while still producing very high chaperone levels (See Table 3).

TABLE 3

Properties of 108 in extract fermentation.

| Intracellular DsbC titer | 4.1 mg/ml |
| Intracellular FkpA titer | 13.9 mg/ml |
| Specific Growth Rate | 0.49/h |

The extract made from strain 108 contained high levels of both chaperones and supported cell-free synthesis of very high levels of recombinant IgGs and other proteins (see Table 4).

TABLE 4

Cell-Free protein titers.

| GMC-SF | 0.44 mg/ml |
| Trastuzumab | 1.1 mg/ml |

Strain 150

Strain SBMT150 is a derivative of SBHS016, a KGK10 derivative with ompT sensitive RF1. To produce SBMT150, 2 copies of DsbC were integrated onto the chromosome into the xy1A locus. Two copies of FkpA were integrated into the galK locus. Both chromosomal integrations were introduced with homologous recombination.

In a standard extract fermentation using DM80-80 in batch mode, strain SBMT150 was capable of achieving a high growth rate while still producing high chaperone levels (see Table 5). Because the chaperones are overexpressed from the genome, no antibiotics are required during the fermentation of this strain.

TABLE 5

Properties of 150 in extract fermentation.

| Intracellular DsbC titer | 2.5 mg/ml |
| Intracellular FkpA titer | 3.4 mg/ml |
| Specific Growth Rate | .071/h |

The extract made from strain 108 contained high levels of both chaperones and supported cell-free synthesis of high levels of recombinant IgGs and other proteins, as shown in the Table 6 below.

TABLE 6

Cell Free Protein Titers.

| GMC-SF | 0.46 mg/ml |
| Trastuzumab | 0.49 mg/ml |

In summary, this example demonstrates that bacterial strains can be engineered to stably incorporate chaperone expression cassettes that express high levels of chaperone proteins without compromising growth rates, and that cell free extracts derived from these strains yield high levels of recombinant proteins of interest.

Example 6

This example shows that extracts derived from bacterial cells that overexpress the DsbC and FkpA chaperones can improve the expression and assembly of multiple different IgG's.

Methods:

2x DsbC and 2x FkpA Extracts.

The E. coli strain SBJY001 (Yin G, et al., Aglycosylated antibodies and antibody fragments produced in a scalable in vitro transcription-translation system. mAbs 2012; 4) was transformed with pACYC-based chaperone overexpression plasmids and harvested in log phase to make cellular extracts. Plasmids carrying one copy (1x DsbC) or two tandem copies (2x DsbC) of dsbC behind the E. coli promoter Mt-cons-10 (Thouvenot B. et al. The strong efficiency of the Escherichia coli gapA P1 promoter depends on a complex combination of functional determinants. Biochem J 2004; 383:371-82) were generated and transformed into bacteria, as were one copy (1x FkpA) or two copies (2x FkpA) of fkpA. These strains were grown to log phase and lysed for the production of cell-free extract, as described (Zawada J. F. et al. Microscale to manufacturing scale-up of cell-free cytokine production—a new approach for shortening protein production development timelines. Biotechnol Bioeng 2011; 108:1570-8). The IgG-producing activities of each of these extracts were tested, either alone or in combination with exogenously added purified protein. A bacterial strain SBHS016 (derived from bacterial strain SBJY001) optimized for OCFS extracts was further modified to enhance the production of DsbC protein. This strain has dual tandem copies of dsbC integrated into the bacterial galK locus, constitutively expressed using a modified MT-cons-10 promoter (Thouvenot B. et al. *Biochem J* 2004; 383:371-82). This is in addition to the wild type gene at the normal dsbC locus. The dual tandem gene cassette contains one copy of the parental dsbC gene, and one copy of a synthetic version of the dsbC gene designed to encode the wild type protein, but with altered codons to suppress unwanted sequence recombination with other versions of dsbC gene elsewhere in the genome. This DsbC overexpressing strain was transformed with the 2× FkpA plasmid to produce strain '2×D+2×F'.

Figure 13:
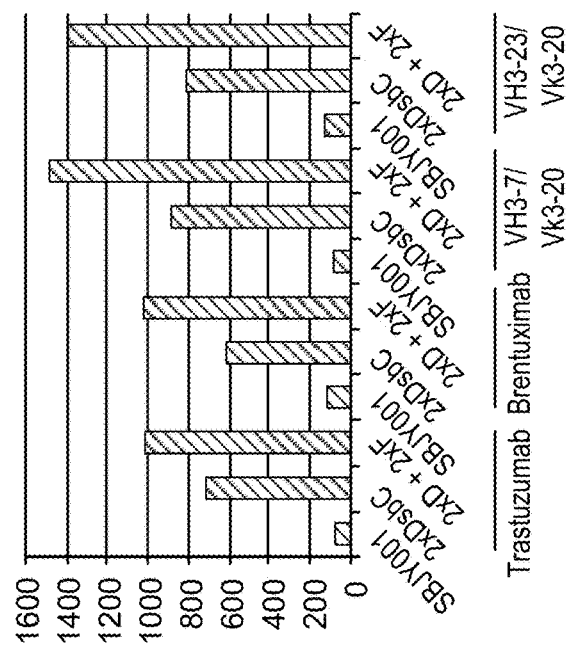
FIG. 13 shows that overexpression of chaperones improves the yield of multiple IgGs in an Open Cell Free Synthesis system. (A) Trastuzumab, the CD30 antigen binding brentuximab, and the germline Heavy Chains VH3-7 and VH3-23 in combination with the germline Light Chain Vk3-20 were expressed in SBJY001, 2× DsbC, and 2×D+ 2×F extracts in the presence of $^{14}$C-leucine and visualized by SDS-PAGE and autoradiography. (B) Assembled IgG expressed in the different extracts was quantified as described in the Examples.
Figure 13:
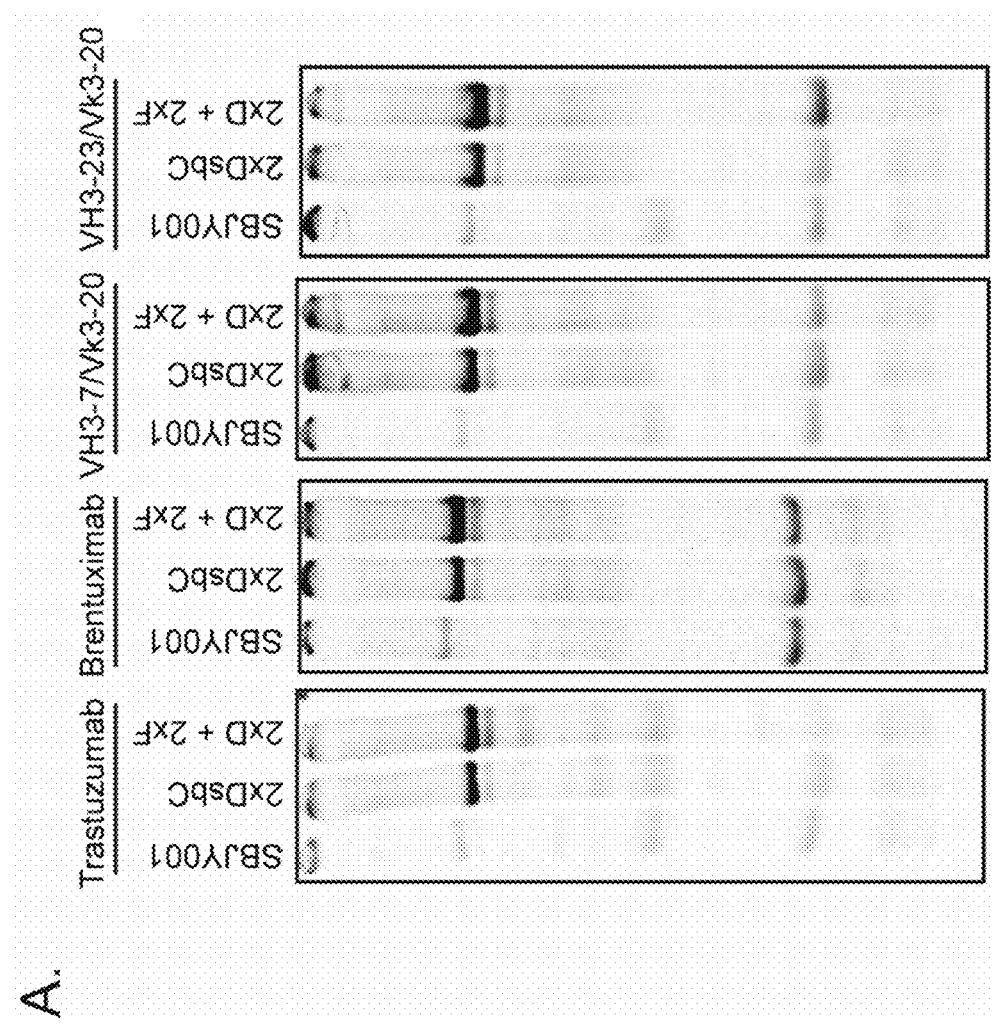

Results:

A panel of different IgG's were translated in a bacterial in vitro transcription/translation system described herein. The IgG's were translated in a control extract (SBJY001), a DsbC extract (2× DsbC extract), and a DsbC+FkpA extract (2×D+2×F). The panel included the therapeutic antibodies trastuzumab (an anti-Her2 IgG1) and brentuximab (an anti-CD30 IgG1), in addition to two germline Heavy Chains VH3-7 and VH3-23 in combination with the Light Chain Vk3-20. As shown in FIG. 13, expression of the IgG's in the 2× DsbC extract dramatically improved the yield of all four IgG's. Further improvements were observed in the DsbC+FkpA extract, bringing expression levels to 1 g/L for both trastuzumab and brentuximab and nearly 1.5 g/L for the germline IgGs.

This example demonstrates that extracts from engineered bacteria that overexpress the chaperones DsbC and FkpA can increase the expression of a wide-range of immunoglobulin proteins in a OCFS coupled transcription-translation system.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

```
Informal Sequence Listing:

SEQ ID NO: 1 NP_417369 protein disulfide isomerase II [Escherichia
coli str. K-12 substr. MG1655] (DsbC; xprA) (UniProt P0AEG6)
  1 MKKGFMLFTL LAAFSGFAQA DDAAIQQTLA KMGIKSSDIQ PAPVAGMKTV LTNSGVLYIT

61 DDGKHIIQGP MYDVSGTAPV NVTNKMLLKQ LNALEKEMIV YKAPQEKHVI TVFTDITCGY

121 CHKLHEQMAD YNALGITVRY LAFPRQGLDS DAEKEMKAIW CAKDKNKAFD DVMAGKSVAP

181 ASCDVDIADH YALGVQLGVS GTPAVVLSNG TLVPGYQPPK EMKEFLDEHQ KMTSGK

SEQ ID NO: 2 NP_418297 periplasmic protein disulfide isomerase I
[Escherichia coli str. K-12 substr. MG1655](DsbA; dsf; ppfA)
(UniProt P0AEG4)
  1 MKKIWLALAG LVLAFSASAA QYEDGKQYTT LEKPVAGAPQ VLEFFSFFCP HCYQFEEVLH

61 ISDNVKKKLP EGVKMTKYHV NFMGGDLGKD LTQAWAVAMA LGVEDKVTVP LFEGVQKTQT

121 IRSASDIRDV FINAGIKGEE YDAAWNSFVV KSLVAQQEKA AADVQLRGVP AMFVNGKYQL

181 NPQGMDTSNM DVFVQQYADT VKYLSEKK

SEQ ID NO: 3 NP_415703 oxidoreductase that catalyzes reoxidation of DsbA
protein disulfide isomerase I [Escherichia coli str. K-12 substr. MG1655]
(DsbB; roxB; ycgA) (UniProt P0A6M2)
  1 MLRFLNQCSQ GRGAWLLMAF TALALELTAL WFQHVMLLKP CVLCIYERCA LFGVLGAALI

61 GAIAPKTPLR YVAMVIWLYS AFRGVQLTYE HTMLQLYPSP FATCDFMVRF PEWLPLDKWV

121 PQVFVASGDC AERQWDFLGL EMPQWLLGIF IAYLIVAVLV VISQPFKAKK RDLFGR

SEQ ID NO: 4 NP_418559 fused thiol:disulfide interchange protein: activator
of DsbC/conserved protein [Escherichia coli str. K-12 substr. MG1655]
(DsbD; C-type cytochrome biogenesis protein CycZ; inner membrane copper
tolerance protein; protein-disulfide reductase) (UniProt P36655)
  1 MAQRIFTLIL LLCSTSVFAG LFDAPGRSQF VPADQAFAFD FQQNQHDLNL TWQIKDGYYL

61 YRKQIRITPE HAKIADVQLP QGVWHEDEFY GKSEIYRDRL TLPVTINQAS AGATLTVTYQ

121 GCADAGFCYP PETKTVPLSE VVANNAAPQP VSVPQQEQPT AQLPFSALWA LLIGIGIAFT

181 PCVLPMYPLI SGIVLGGKQR LSTARALLLT FIYVQGMALT YTALGLVVAA AGLQFQAALQ

241 HPYVLIGLAI VFTLLAMSMF GLFTLQLPSS LQTRLTLMSN RQQGGSPGGV FVMGAIAGLI

301 CSPCTTAPLS AILLYIAQSG NMWLGGGTLY LYALGMGLPL MLITVFGNRL LPKSGPWMEQ

361 VKTAFGFVIL ALPVFLLERV IGDVWGLRLW SALGVAFFGW AFITSLQAKR GWMRIVQIIL

421 LAAALVSVRP LQDWAFGATH TAQTQTHLNF TQIKTVDELN QALVEAKGKP VMLDLYADWC
```

Informal Sequence Listing:

481 VACKEFEKYT FSDPQVQKAL ADTVLLQANV TANDAQDVAL LKHLNVLGLP TILFFDGQGQ

541 EHPQARVTGF MDAETFSAHL RDRQP

SEQ ID NO: 5 NP_415137 thiol:disulfide interchange protein, periplasmic [*Escherichia coli* str. K-12 substr. MG1655] (DsbG; ybdP) (UniProt P77202)
  1 MLKKILLLAL LPAIAFAEEL PAPVKAIEKQ GITIIKTFDA PGGMKGYLGK YQDMGVTIYL

61 TPDGKHAISG YMYNEKGENL SNTLIEKEIY APAGREMWQR MEQSHWLLDG KKDAPVIVYV

121 FADPFCPYCK QFWQQARPWV DSGKVQLRTL LVGVIKPESP ATAAAILASK DPAKTWQQYE

181 ASGGKLKLNV PANVSTEQMK VLSDNEKLMD DLGANVTPAI YYMSKENTLQ QAVGLPDQKT

241 LNIIMGNK

SEQ ID NO: 6 NP_417806 FKBP-type peptidyl-prolyl cis-trans isomerase (rotamase) [*Escherichia coli* str. K-12 substr. MG1655] (FkpA; PPIase) (UniProt P45523)
  1 MKSLFKVTLL ATTMAVALHA PITFAAEAAK PATAADSKAA FKNDDQKSAY ALGASLGRYM

61 ENSLKEQEKL GIKLDKDQLI AGVQDAFADK SKLSDQEIEQ TLQAFEARVK SSAQAKMEKD

121 AADNEAKGKE YREKFAKEKG VKTSSTGLVY QVVEAGKGEA PKDSDTVVVN YKGTLIDGKE

181 FDNSYTRGEP LSFRLDGVIP GWTEGLKNIK KGGKIKLVIP PELAYGKAGV PGIPPNSTLV

241 FDVELLDVKP APKADAKPEA DAKAADSAKK

SEQ ID NO: 7 NP_417808 FKBP-type peptidyl prolyl cis-trans isomerase (rotamase) [*Escherichia coli* str. K-12 substr. MG1655] (SlyD; histidine-rich protein; metallochaperone SlyD; sensitivity to lysis protein D; WHP; PPIase) (UniProt P0A9K9)
  1 MKVAKDLVVS LAYQVRTEDG VLVDESPVSA PLDYLHGHGS LISGLETALE GHEVGDKFDV

61 AVGANDAYGQ YDENLVQRVP KDVFMGVDEL QVGMRFLAET DQGPVPVEIT AVEDDHVVVD

121 GNHMLAGQNL KFNVEVVAIR EATEEELAHG HVHGAHDHHH DHDHDGCCGG HGHDHGHEHG

181 GEGCCGGKGN GGCGCH

SEQ ID NO: 8 NP_414595 peptidyl-prolyl cis-trans isomerase (PPIase) [*Escherichia coli* str. K-12 substr. MG1655] (SurA; peptidyl-prolyl cis-trans isomerase SurA; rotamase SurA; survival protein A; PPIase SurA) (UniProt P0ABZ6)
  1 MKNWKTLLLG IAMIANTSFA APQVVDKVAA VVNNGVVLES DVDGLMQSVK LNAAQARQQL

61 PDDATLRHQI MERLIMDQII LQMGQKMGVK ISDEQLDQAI ANIAKQNNMT LDQMRSRLAY

121 DGLNYNTYRN QIRKEMIISE VRNNEVRRRI TILPQEVESL AQQVGNQNDA STELNLSHIL

181 IPLPENPTSD QVNEAESQAR AIVDQARNGA DFGKLAIAHS ADQQALNGGQ MGWRIQELP

241 GIFAQALSTA KKGDIVGPIR SGVGFHILKV NDLRGESKNI SVTEVHARHI LLKPSPIMTD

301 EQARVKLEQI AADIKSGKTT FAAAAKEFSQ DPGSANQGGD LGWATPDIFD PAFRDALTRL

361 NKGQMSAPVH SSFGWHLIEL LDTRNVDKTD AAQKDRAYRM LMNRKFSEEA ASWMQEQRAS

421 AYVKILSN

SEQ ID NO: 9 NP_414720 periplasmic chaperone [*Escherichia coli* str. K-12 substr. MG1655] (Skp; chaperone protein skp; DNA-binding 17 kDa protein; histone-like protein HLP-1; hlpA) (UniProt P0AEU7)
  1 MKKWLLAAGL GLALATSAQA ADKIAIVNMG SLFQQVAQKT GVSNTLENEF KGRASELQRM

61 ETDLQAKMKK LQSMKAGSDR TKLEKDVMAQ RQTFAQKAQA FEQDRARRSN EERGKLVTRI

121 QTAVKSVANS QDIDLVVDAN AVAYNSSDVK DITADVLKQV K

SEQ ID NO: 10 NP_009887 protein disulfide isomerase PDI1 [*Saccharomyces cerevisiae* S288c] (yPDI; thioredoxin-related glycoprotein 1;TRG1; MFP1) (UniProt P17967)
  1 MKFSAGAVLS WSSLLLASSV FAQQEAVAPE DSAVVKLATD SFNEYIQSHD LVLAEFFAPW

61 CGHCKNMAPE YVKAAETLVE KNITLAQIDC TENQDLCMEH NIPGFPSLKI FKNSDVNNSI

```
121 DYEGPRTAEA IVQFMIKQSQ PAVAVVADLP AYLANETFVT PVIVQSGKID ADFNATFYSM

181 ANKHFNDYDF VSAENADDDF KLSIYLPSAM DEPVVYNGKK ADIADADVFE KWLQVEALPY

241 FGEIDGSVFA QYVESGLPLG YLFYNDEEEL EEYKPLFTEL AKKNRGLMNF VSIDARKFGR

301 HAGNLNMKEQ FPLFAIHDMT EDLKYGLPQL SEEAFDELSD KIVLESKAIE SLVKDFLKGD

361 ASPIVKSQEI FENQDSSVFQ LVGKNHDEIV NDPKKDVLVL YYAPWCGHCK RLAPTYQELA

421 DTYANATSDV LIAKLDHTEN DVRGVVIEGY PTIVLYPGGK KSESVVYQGS RSLDSLFDFI

481 KENGHFDVDG KALYEEAQEK AAEEADADAE LADEEDAIHD EL

SEQ ID NO: 11 NP_000909 protein disulfide-isomerase precursor [Homo
sapiens] (hPDI; PDI; protein disulfide isomerase-associated 1; DSI;
protocollagen hydroxylase; collagen prolyl 4-hydroxylase beta,
procollagen-proline, 2-oxoglutarate 4-dioxygenase (proline 4-
hydroxylase), beta polypeptide; prolyl 4-hydroxylase subunit beta;
P4HB; PHDB; PO4DB; PO4HB; PROHB; P4Hbeta; protein disulfide
isomerase family A, member 1; PDIA1; protein disulfideisomerase/
oxidoreductase; thyroid hormone-binding protein p55; glutathione-
insulin transhydrogenase; protein disulfide-isomerase; prolyl 4-
hydroxylase subunit beta; cellular thyroid hormone-binding protein;
glutathione-insulin transhydrogenase; GIT; ERBA2L) (UniProt P07237)
  1 MLRRALLCLA VAALVRADAP EEEDHVLVLR KSNFAEALAA HKYLLVEFYA PWCGHCKALA

61 PEYAKAAGKL KAEGSEIRLA KVDATEESDL AQQYGVRGYP TIKFFRNGDT ASPKEYTAGR

121 EADDIVNWLK KRTGPAATTL PDGAAAESLV ESSEVAVIGF FKDVESDSAK QFLQAAEAID

181 DIPFGITSNS DVFSKYQLDK DGVVLFKKFD EGRNNFEGEV TKENLLDFIK HNQLPLVIEF

241 TEQTAPKIFG GEIKTHILLF LPKSVSDYDG KLSNFKTAAE SFKGKILFIF IDSDHTDNQR

301 ILEFFGLKKE ECPAVRLITL EEEMTKYKPE SEELTAERIT EFCHRFLEGK IKPHLMSQEL

361 PEDWDKQPVK VLVGKNFEDV AFDEKKNVFV EFYAPWCGHC KQLAPIWDKL GETYKDHENI

421 VIAKMDSTAN EVEAVKVHSF PTLKFFPASA DRTVIDYNGE RTLDGFKKFL ESGGQDGAGD

481 DDDLEDLEEA EEPDMEEDDD QKAVKDEL

SEQ ID NO: 12 NP_010640 thioredoxin-disulfide reductase TRR1 [Saccharomyces
cerevisiae S288c] (yTrr1; cytoplasmic thioredoxin reductase)
(UniProt P29509)
  1 MVHNKVTIIG SGPAAHTAAI YLARAEIKPI LYEGMMANGI AAGGQLTTTT EIENFPGFPD

61 GLTGSELMDR MREQSTKFGT EIITETVSKV DLSSKPFKLW TEFNEDAEPV TTDAIILATG

121 ASAKRMHLPG EETYWQKGIS ACAVCDGAVP IFRNKPLAVI GGGDSACEEA QFLTKYGSKV

181 FMLVRKDHLR ASTIMQKRAE KNEKIEILYN TVALEAKGDG KLLNALRIKN TKKNEETDLP

241 VSGLFYAIGH TPATKIVAGQ VDTDEAGYIK TVPGSSLTSV PGFFAAGDVQ DSKYRQAITS

301 AGSGCMAALD AEKYLTSLE

SEQ ID NO: 13 NP_015234 glutathione-disulfide reductase GLR1 [Saccharomyces
cerevisiae S288c] (yGlr1; glutathione reductase; GR; GRase; LPG17) (UniProt
P41921)
  1 MLSATKQTFR SLQIRTMSTN TKHYDYLVIG GGSGGVASAR RAASYGAKTL VEAKALGGT

61 CVNVGCVPKK VMWYASDLAT RVSHANEYGL YQNLPLDKEH LTFNWPEFKQ KRDAYVHRLN

121 GIYQKNLEKE KVDVVFGWAR FNKDGNVEVQ KRDNTTEVYS ANHILVATGG KAIFPENIPG

181 FELGTDSDGF FRLEEQPKKV VVGAGYIGI ELAGVFHGLG SETHLVIRGE TVLRKFDECI

241 QNTITDHYVK EGINVHKLSK IVKVEKNVET DKLKIHMNDS KSIDDVDELI WTIGRKSHLG
```

```
Informal Sequence Listing:

301 MGSENVGIKL NSHDQIIADE YQNTNVPNIY SLGDVVGKVE LTPVAIAAGR KLSNRLFGPE

361 KFRNDKLDYE NVPSVIFSHP EAGSIGISEK EAIEKYGKEN IKVYNSKFTA MYYAMLSEKS

421 PTRYKIVCAG PNEKVVGLHI VGDSSAEILQ GFGVAIKMGA TKADFDNCVA IHPTSAEELV

481 TMR

SEQ ID NO: 14 NP_414970 peptidyl-prolyl cis/trans isomerase
(trigger factor) [Escherichia coli str. K-12 substr. MG1655]
(tig; TF; ECK0430; JW0426; PPIase) (UniProt P0A850)
  1 MQVSVETTQG LGRRVTITIA ADSIETAVKS ELVNVAKKVR IDGFRKGKVP MNIVAQRYGA

61 SVRQDVLGDL MSRNFIDAII KEKINPAGAP TYVPGEYKLG EDFTYSVEFE VYPEVELQGL

121 EAIEVEKPIV EVTDADVDGM LDTLRKQQAT WKEKDGAVEA EDRVTIDFTG SVDGEEFEGG

181 KASDFVLAMG QGRMIPGFED GIKGHKAGEE FTIDVTFPEE YHAENLKGKA AKFAINLKKV

241 EERELPELTA EFIKRFGVED GSVEGLRAEV RKNMERELKS AIRNRVKSQA IEGLVKANDI

301 DVPAALIDSE IDVLRRQAAQ RFGGNEKQAL ELPRELFEEQ AKRRVVVGLL LGEVIRTNEL

361 KADEERVKGL IEEMASAYED PKEVIEFYSK NKELMDNMRN VALEEQAVEA VLAKAKVTEK

421 ETTFNELMNQ QA

SEQ ID NO: 15 NP_000933 peptidyl-prolyl cis-trans isomerase B precursor
[Homo sapiens] (hPPIB; PPIase B; PPIB; rotamase B; cyclophilin B;
cyclophilin-like protein; S-cyclophilin; SCYLP; CYP-S1; CYPB)
(UniProt P23284)
  1 MLRLSERNMK VLLAAALIAG SVFFLLLPGP SAADEKKKGP KVTVKVYFDL RIGDEDVGRV

61 IFGLFGKTVP KTVDNFVALA TGEKGFGYKN SKFHRVIKDF MIQGGDFTRG DGTGGKSIYG

121 ERFPDENFKL KHYGPGWVSM ANAGKDTNGS QFFITTVKTA WLDGKHVVFG KVLEGMEVVR

181 KVESTKTDSR DKPLKDVIIA DCGKIEVEKP FAIAKE

SEQ ID NO: 16 NP_010439 peptidylprolyl isomerase CPR1 [Saccharomyces
cerevisiae S288c] (Cpr1, peptidyl-prolyl cis-trans isomerase, cyclophilin,
CPH1, CYP1, cyclosporin A-binding protein, rotamase, PPIase, PPI-II)
(UniProt P14832)
  1 MSQVYFDVEA DGQPIGRVVF KLYNDIVPKT AENFRALCTG EKGFGYAGSP FHRVIPDFML

61 QGGDFTAGNG TGGKSIYGGK FPDENFKKHH DRPGLLSMAN AGPNTNGSQF FITTVPCPWL

121 DGKHVVFGEV VDGYDIVKKV ESLGSPSGAT KARIVVAKSG EL

SEQ ID NO: 17 NP_013317 peptidylprolyl isomerase CPR6 [Saccharomyces
cerevisiae S288c] (Cpr6, cyclophilin, CYP40, rotamase CPR6, PPIase CPR6)
(UniProt P53691)
  1 MTRPKTFFDI SIGGKPQGRI VFELYNDIVP KTAENFLKLC EGNAGMAKTK PDVPLSYKGS

61 IFHRVIKDFM CQFGDFTNFN GTGGESIYDE KFEDENFTVK HDKPFLLSMA NAGPNTNGSQ

121 AFITCVPTPH LDGKHVVFGE VIQGKRIVRL IENQQCDQEN NKPLRDVKID DCGVLPDDYQ

181 VPENAEATPT DEYGDNYEDV LKQDEKVDLK NFDTVLKAIE TVKNIGTEQF KKQNYSVALE

241 KYVKCDKFLK EYFPEDLEKE QIEKINQLKV SIPLNIAICA LKLKDYKQVL VASSEVLYAE

301 AADEKAKAKA LYRRGLAYYH VNDTDMALND LEMATTFQPN DAAILKAIHN TKLKRKQQNE

361 KAKKSLSKMF S

SEQ ID NO: 18 NP_014264 peptidylprolyl isomerase FPR1 [Saccharomyces
cerevisiae S288c] (Fpr1, FK506-binding protein 1, FKBP, FKB1, rapamycin-
binding protein, RBP1, PPIase) (UniProt P20081)
  1 MSEVIEGNVK IDRISPGDGA TFPKTGDLVT IHYTGTLENG QKFDSSVDRG SPFQCNIGVG

61 QVIKGWDVGI PKLSVGEKAR LTIPGPYAYG PRGFPGLIPP NSTLVFDVEL LKVN
```

```
Informal Sequence Listing:

SEQ ID NO: 19 NP_057390 dnaJ homolog subfamily B member 11 precursor [Homo
sapiens] (hERdj3; DnaJ (Hsp40) homolog, subfamily B, member 11; ER-
associated DNAJ; ER-associated Hsp40 co-chaperone; ER-associated dnaJ
protein 3; ERdj3; ERj3p; EDJ; ERJ3; ERj3; HEDJ; human DnaJ protein 9; DnaJ
protein homolog 9HDJ9; DJ9; Dj-9; hDj-9; PWP1-interacting protein 4;
APOBEC1-binding protein 2; ABBP-2; ABBP2; DNAJB11; PRO1080; UNQ537)
(UniProt Q9UBS4)
  1 MAPQNLSTFC LLLLYLIGAV IAGRDFYKIL GVPRSASIKD IKKAYRKLAL QLHPDRNPDD

61 PQAQEKFQDL GAAYEVLSDS EKRKQYDTYG EEGLKDGHQS SHGDIFSHFF GDFGFMFGGT

121 PRQQDRNIPR GSDIIVDLEV TLEEVYAGNF VEVVRNKPVA RQAPGKRKCN CRQEMRTTQL

181 GPGRFQMTQE VVCDECPNVK LVNEERTLEV EIEPGVRDGM EYPFIGEGEP HVDGEPGDLR

241 FRIKVVKHPI FERRGDDLYT NVTISLVESL VGFEMDITHL DGHKVHISRD KITRPGAKLW

301 KKGEGLPNFD NNNIKGSLII TFDVDFPKEQ LTEEAREGIK QLLKQGSVQK VYNGLQGY

SEQ ID NO: 20 NP_005338 78 kDa glucose-regulated protein precursor [Homo
sapiens] (BiP; endoplasmic reticulum lumenal Ca(2+)-binding protein grp78;
GRP-78; heat shock 70 kDa protein 5; HSPA5; immunoglobulin heavy chain-
binding protein; MIF2) (UniProt P11021)
  1 MKLSLVAAML LLLSAARAEE EDKKEDVGTV VGIDLGTTYS CVGVFKNGRV EIIANDQGNR

61 ITPSYVAFTP EGERLIGDAA KNQLTSNPEN TVFDAKRLIG RTWNDPSVQQ DIKFLPFKVV

121 EKKTKPYIQV DIGGGQTKTF APEEISAMVL TKMKETAEAY LGKKVTHAVV TVPAYFNDAQ

181 RQATKDAGTI AGLNVMRIIN EPTAAAIAYG LDKREGEKNI LVFDLGGGTF DVSLLTIDNG

241 VFEVVATNGD THLGGEDFDQ RVMEHFIKLY KKKTGKDVRK DNRAVQKLRR EVEKAKRALS

301 SQHQARIEIE SFYEGEDFSE TLTRAKFEEL NMDLFRSTMK PVQKVLEDSD LKKSDIDEIV

361 LVGGSTRIPK IQQLVKEFFN GKEPSRGINP DEAVAYGAAV QAGVLSGDQD TGDLVLLDVC

421 PLTLGIETVG GVMTKLIPRN TVVPTKKSQI FSTASDNQPT VTIKVYEGER PLTKDNHLLG

481 TFDLTGIPPA PRGVPQIEVT FEIDVNGILR VTAEDKGTGN KNKITITNDQ NRLTPEEIER

541 MVNDAEKFAE EDKKLKERID TRNELESYAY SLKNQIGDKE KLGGKLSSED KETMEKAVEE

601 KIEWLESHQD ADIEDFKAKK KELEEIVQPI ISKLYGSAGP PPTGEEDTAE KDEL

SEQ ID NO: 21 NP_013911 Hsp90 family chaperone HSC82 [Saccharomyces
cerevisiae S288c] (yHsc82; HSC82; ATP-dependent molecular chaperone HSC82;
82 kDa heat shock cognate protein; heat shock protein Hsp90 constitutive
isoform; HSP90; cytoplasmic chaperone of the Hsp90 family) (UniProt P15108)
  1 MAGETFEFQA EITQLMSLII NTVYSNKEIF LRELISNASD ALDKIRYQAL SDPKQLETEP

61 DLFIRITPKP EEKVLEIRDS GIGMTKAELI NNLGTIAKSG TKAFMEALSA GADVSMIGQF

121 GVGFYSLFLV ADRVQVISKN NEDEQYIWES NAGGSFTVTL DEVNERIGRG TVLRLFLKDD

181 QLEYLEEKRI KEVIKRHSEF VAYPIQLLVT KEVEKEVPIP EEEKKDEEKK DEDDKKPKLE

241 EVDEEEEEKK PKTKKVKEEV QELEELNKTK PLWTRNPSDI TQEEYNAFYK SISNDWEDPL

301 YVKHFSVEGQ LEFRAILFIP KRAPFDLFES KKKKNNIKLY VRRVFITDEA EDLIPEWLSF

361 VKGVVDSEDL PLNLSREMLQ QNKIMKVIRK NIVKKLIEAF NEIAEDSEQF DKFYSAFAKN

421 IKLGVHEDTQ NRAALAKLLR YNSTKSVDEL TSLTDYVTRM PEHQKNIYYI TGESLKAVEK

481 SPFLDALKAK NFEVLFLTDP IDEYAFTQLK EFEGKTLVDI TKDFELEETD EEKAEREKEI

541 KEYEPLTKAL KDILGDQVEK VVVSYKLLDA PAAIRTGQFG WSANMERIMK AQALRDSSMS

601 SYMSSKKTFE ISPKSPIIKE LKKRVDEGGA QDKTVKDLTN LLFETALLTS GFSLEEPTSF

661 ASRINRLISL GLNIDEDEET ETAPEASTEA PVEEVPADTE MEEVD
```

Informal Sequence Listing:

SEQ ID NO: 22 NP_418142 heat shock chaperone [*Escherichia coli* str. K-12 substr. MG1655] (IbpA; small heat shock protein IbpA; 16 kDa heat shock protein A; hslT; htpN; ECK3679; JW3664) (UniProt P00054)
1 MRNFDLSPLY RSAIGFDRLF NHLENNQSQS NGGYPPYNVE LVDENHYRIA IAVAGFAESE

61 LEITAQDNLL VVKGAHADEQ KERTYLYQGI AERNFERKFQ LAENIHVRGA NLVNGLLYID

121 LERVIPEAKK PRRIEIN

SEQ ID NO: 23 NP_418141 heat shock chaperone [*Escherichia coli* str. K-12 substr. MG1655] (IbpB; small heat shock protein IbpB; 16 kDa heat shock protein B; hslS; htpE; ECK3678; JW3663) (UniProt P00058)
1 MRNFDLSPLM RQWIGFDKLA NALQNAGESQ SFPPYNIEKS DDNHYRITLA LAGFRQEDLE

61 IQLEGTRLSV KGTPEQPKEE KKWLHQGLMN QPFSLSFTLA ENMEVSGATF VNGLLHIDLI

121 RNEPEPIAAQ RIAISERPAL NS

What is claimed is:

1. A bacterial cell free synthesis system for expressing biologically active proteins comprising:
   i) a cell free S30 extract of *E. coli* bacteria having an active oxidative phosphorylation system, containing biologically functioning tRNA, amino acids and ribosomes necessary for cell free protein synthesis and where the bacteria were transformed with genes encoding a disulfide isomerase and a prolyl isomerase wherein the two isomerases are expressed in the bacteria at a total concentration of at least 1 g/liter of extract; and
   ii) a nucleic acid encoding a protein of interest, wherein the protein of interest comprises a disulfide bond and a proline residue,
   and where a concentration of the protein of interest is increased compared to the sum of the concentration expressed by bacteria separately transformed with individual genes encoding the disulfide isomerase and the prolyl isomerase, and the incubation conditions are otherwise the same.

2. The system of claim 1, wherein the disulfide isomerase is DsbA, DsbB, DsbC, DsbD, or yeast PDI, and the prolyl isomerase is FkpA, SlyD, trigger factor (tig) or Skp.

3. The system of claim 1, wherein the bacteria from which the extract is prepared expresses at least one of the disulfide isomerase and the prolyl isomerase from a gene operably linked to a constitutive promoter.

4. The system of claim 1, wherein the protein of interest has at least two proline residues.

5. The system of claim 1, wherein the protein of interest is an antibody or antibody fragment.

6. The system of claim 1, wherein said protein of interest is expressed at a concentration of 100 mg/L to 1000 mg/L.

7. The system of claim 1, wherein said disulfide isomerase and prolyl isomerase are expressed in the bacteria at a concentration of 1 g/liter to 20 g/liter of extract.

8. The system of claim 1, wherein said disulfide isomerase is expressed in the bacteria at a concentration of 2.5 g/liter to 4.1 g/liter of extract, and the prolyl isomerase is expressed in the bacteria at a concentration of 3.4 g/liter to 13.9 g/liter of extract.

9. The system of claim 1, wherein said protein of interest is expressed at a concentration greater than 600 mg/L.

10. The system of claim 1, wherein the disulfide isomerase is a redox chaperone, and the prolyl isomerase is a FK506 binding protein (FKBP) or a parvulin.

11. The system of claim 2, wherein the disulfide isomerase is DsbC, and the prolyl isomerase is FkpA.

12. A method of improving the expression levels of biologically active proteins in a bacterial cell free synthesis system comprising the steps of:
   i) combining a bacterial S30 extract of *E. coli* with a nucleic acid encoding a protein of interest to yield a bacterial cell free synthesis system; and,
   ii) incubating the bacterial cell free synthesis system under conditions permitting the expression of the protein of interest to a concentration of at least about 100 mg/L, wherein the protein of interest comprises a disulfide bond and a proline residue,
   wherein the bacterial extract has an active oxidative phosphorylation system and comprises biologically functioning tRNA, amino acids and ribosomes necessary for cell free protein synthesis, and the extract is prepared from a bacteria that expresses an exogenous disulfide isomerase and an exogenous prolyl isomerase at a total concentration of at least about 1 g/liter of extract, and where the concentration of the protein of interest is increased compared to the sum of the concentration expressed by the bacterial cell free synthesis system when the extract is prepared from bacteria that express one but not both of the exogenous disulfide isomerase and the exogenous prolyl isomerase, and the incubation conditions are otherwise the same.

13. A bacterial cell free synthesis system for expressing biologically active proteins comprising:

i) a cell free S30 extract of *E. coli* bacteria having an active oxidative phosphorylation system, containing biologically functioning tRNA, amino acids and ribosomes necessary for cell free protein synthesis and further including a protein disulfide isomerase and a peptidyl-prolyl cis-trans isomerase, wherein the protein disulfide isomerase and the peptidyl-prolyl cis-trans isomerase are present at a concentration of at least 1 gm/liter of extract; and ii) a nucleic acid encoding a protein of interest comprising a disulfide bond and a proline residue;

wherein said bacterial cell free synthesis system expresses a protein of interest to a concentration of at least about 100 mg/L, and wherein the expression of the protein of interest is increased to a concentration above that concentration where one but not both of the protein disulfide isomerase and the peptidyl-prolyl cis-trans isomerase are present, and the incubation conditions are otherwise the same.

14. The system of claim 13, wherein the total concentration of the protein disulfide isomerase and the peptidyl-prolyl cis-trans is between 1 gm/liter and 14 gm/liter in the extract.

15. The system of claim 13, wherein the protein disulfide isomerase is selected from the group consisting of DsbA, DsbB, DsbC, DsbD, and yeast PDI, and the peptidyl-prolyl cis-trans isomerase is selected from the group consisting of FkpA, SlyD, trigger factor (tig) and Skp.

16. The system of claim 13, wherein the bacteria from which the extract is prepared expresses at least one of the protein disulfide isomerase and peptidyl-prolyl cis-trans isomerase from a gene operably linked to a constitutive promoter.

17. The system of claim 13, wherein the bacteria is *Escherichia coli*.

18. A method of expressing properly folded, biologically active proteins in a bacterial cell free synthesis system comprising the steps of:

i) combining a bacterial extract with a nucleic acid encoding a protein of interest comprising a disulfide bond and a proline residue; and ii) incubating the bacterial extract with the nucleic acid under conditions permitting the expression and proper folding of the protein of interest, wherein the bacterial extract is an S30 extract of *E. coli* bacteria comprising biologically functioning tRNA, amino acids, ribosomes necessary for cell free protein synthesis, a protein disulfide isomerase and a peptidyl-prolyl cis-trans isomerase, wherein the protein disulfide isomerase and the peptidyl-prolyl cis-trans isomerase are present at a concentration of at least 1 g/liter of extract, and where the expression of the protein of interest is increased to a concentration greater than the sum of the concentration expressed when the bacterial extract comprises one but not both of the protein disulfide isomerase and the peptidyl-prolyl cis-trans isomerase, and the incubation conditions are otherwise the same.

19. A bacterial cell free extract for expressing biologically active proteins comprising an active oxidative phosphorylation system containing biologically functioning tRNA, amino acids and ribosomes necessary for cell free protein synthesis, wherein the extract is an S30 extract of *E. coli*, and further including a protein disulfide isomerase and a peptidyl-prolyl cis-trans isomerase, wherein the protein disulfide isomerase and the peptidyl-prolyl cis-trans isomerase are present in a total concentration of at least about 1 g/liter in the extract.

20. A method for preparing a bacterial extract, comprising:

i) culturing an *E. coli* bacteria that expresses an exogenous protein disulfide isomerase and an exogenous peptidyl-prolyl cis-trans isomerase, and ii) preparing an S30 extract having an active oxidative phosphorylation system from the bacteria, the extract comprising biologically functioning tRNA, amino acids and ribosomes necessary for cell free protein synthesis, wherein the protein disulfide isomerase and the peptidyl-prolyl cis-trans isomerase are present in a total concentration of at least about 1 g/liter in the extract.

* * * * *